United States Patent  (10) Patent No.: US 8,585,607 B2
Klap et al.  (45) Date of Patent: Nov. 19, 2013

(54) MONITORING, PREDICTING AND TREATING CLINICAL EPISODES

(75) Inventors: Tal Klap, Netanya (IL); Shiraz Levkovich, Moshav Nehalim (IL); Zvika Shinar, Binyamina (IL); Guy Meger, Haifa (IL)

(73) Assignee: EarlySense Ltd., Ramat Gan (IL)

(*) Notice: Subject to any disclaimer, the term of this patent is extended or adjusted under 35 U.S.C. 154(b) by 381 days.

(21) Appl. No.: 12/938,421

(22) Filed: Nov. 3, 2010

(65) Prior Publication Data

US 2011/0046498 A1  Feb. 24, 2011

Related U.S. Application Data

(63) Continuation-in-part of application No. PCT/IL2009/000473, filed on May 10, 2009, which is a continuation-in-part of application No. 12/113,680, filed on May 1, 2008.

(60) Provisional application No. 61/052,395, filed on May 12, 2008, provisional application No. 61/054,754, filed on May 20, 2008, provisional application No. 61/082,510, filed on Jul. 22, 2008, provisional application No. 61/103,276, filed on Oct. 7, 2008, provisional application No. 61/141,677, filed on Dec. 31, 2008, provisional application No. 61/144,743, (Continued)

(51) Int. Cl.
*A61B 5/08* (2006.01)

(52) U.S. Cl.
USPC ............................................. 600/534

(58) Field of Classification Search
USPC ............................ 600/484, 529, 534, 535, 536
See application file for complete search history.

(56) References Cited

U.S. PATENT DOCUMENTS 3,890,958 A  6/1975  Fister
4,122,838 A  10/1978  Leonard
(Continued)

FOREIGN PATENT DOCUMENTS

EP  0860803  8/1998
EP  0853918 B1  2/2005
(Continued)

OTHER PUBLICATIONS

E. Campo, M. Chan, Detecting abnormal behaviour by real-time monitoring of patients, AAAI Technical Report WS-02-02 (2002).

(Continued)

*Primary Examiner* — Navin Natnithithadha
*Assistant Examiner* — Etsub Berhanu
(74) *Attorney, Agent, or Firm* — Rodney J. Fuller; Booth Udall Fuller, PLC

(57) ABSTRACT

Apparatus and methods are provided for use with a subject who is undergoing respiration. A motion sensor senses motion of a subject. A breathing pattern analysis unit analyzes components of the sensed motion that result from the subject's respiration. The breathing pattern analysis unit includes double-movement-respiration-cycle-pattern-identification functionality that designates respiration cycles as being double-movement-respiration-cycles (DMRC's) by determining that the cycles define two subcycles. Double-movement-respiration-cycle-event-identification functionality of the breathing pattern analysis unit identifies a DMRC event by detecting that the subject has undergone a plurality of DMRC's. An output is generated that is indicative of the subject having used accessory muscles in breathing, in response to identification of the double-movement-respiration-cycle event. Other embodiments are also described.

37 Claims, 26 Drawing Sheets

Related U.S. Application Data

(60) filed on Jan. 15, 2009, provisional application No. 60/924,181, filed on May 2, 2007, provisional application No. 60/924,459, filed on May 16, 2007, provisional application No. 60/935,194, filed on Jul. 31, 2007, provisional application No. 60/981,525, filed on Oct. 22, 2007, provisional application No. 60/983,945, filed on Oct. 31, 2007, provisional application No. 60/989,942, filed on Nov. 25, 2007, provisional application No. 61/028,551, filed on Feb. 14, 2008, provisional application No. 61/034,165, filed on Mar. 6, 2008, provisional application No. 61/257,473, filed on Nov. 3, 2009.

(56) References Cited

U.S. PATENT DOCUMENTS

| | | |
|---|---|---|
| 4,301,879 A | 11/1981 | Dubow |
| 4,338,950 A | 7/1982 | Barlow, Jr. |
| 4,494,553 A | 1/1985 | Sciarra |
| 4,657,025 A | 4/1987 | Orlando |
| 4,657,026 A | 4/1987 | Tagg |
| 4,686,999 A | 8/1987 | Snyder |
| 4,738,264 A | 4/1988 | Orlando |
| 4,757,825 A | 7/1988 | Diamond |
| 4,817,610 A | 4/1989 | Lee |
| 4,926,866 A | 5/1990 | Lee |
| 5,002,060 A | 3/1991 | Nedivi |
| 5,010,772 A | 4/1991 | Bourland |
| 5,025,791 A | 6/1991 | Niwa |
| 5,076,281 A | 12/1991 | Gavish |
| 5,107,845 A | 4/1992 | Guern |
| 5,111,826 A | 5/1992 | Nasiff |
| 5,137,033 A | 8/1992 | Norton |
| 5,235,989 A | 8/1993 | Zomer |
| 5,253,656 A | 10/1993 | Rincoe |
| 5,276,432 A | 1/1994 | Travis |
| 5,309,921 A | 5/1994 | Kisner |
| 5,309,922 A | 5/1994 | Schechter |
| 5,319,363 A | 6/1994 | Welch |
| 5,368,026 A | 11/1994 | Swedlow |
| 5,393,935 A | 2/1995 | Hasty |
| 5,448,996 A | 9/1995 | Bellin |
| 5,479,939 A | 1/1996 | Ogino |
| 5,515,865 A | 5/1996 | Scanlon |
| 5,520,176 A | 5/1996 | Cohen |
| 5,522,382 A | 6/1996 | Sullivan |
| 5,540,734 A | 7/1996 | Zabara |
| 5,590,650 A | 1/1997 | Genova |
| 5,620,003 A | 4/1997 | Sepponen |
| 5,684,460 A | 11/1997 | Scanlon |
| 5,687,734 A | 11/1997 | Dempsey |
| 5,699,038 A | 12/1997 | Ulrich |
| 5,730,140 A | 3/1998 | Fitch |
| 5,738,102 A | 4/1998 | Lemelson |
| 5,743,263 A | 4/1998 | Baker, Jr. |
| 5,797,852 A | 8/1998 | Karakasoglu |
| 5,800,337 A | 9/1998 | Gavish |
| 5,800,360 A | 9/1998 | Kisner |
| 5,853,005 A | 12/1998 | Scanlon |
| 5,879,313 A | 3/1999 | Raviv |
| 5,902,250 A | 5/1999 | Verrier |
| 5,944,680 A | 8/1999 | Christopherson |
| 5,957,861 A | 9/1999 | Combs |
| 5,964,720 A | 10/1999 | Pelz |
| 5,989,193 A | 11/1999 | Sullivan |
| 6,014,346 A | 1/2000 | Malone |
| 6,015,388 A | 1/2000 | Sackner |
| 6,033,370 A | 3/2000 | Reinbold |
| 6,036,660 A | 3/2000 | Toms |
| 6,047,203 A | 4/2000 | Sackner |
| 6,062,216 A | 5/2000 | Corn |
| 6,064,910 A | 5/2000 | Andersson |
| 6,080,106 A | 6/2000 | Lloyd |
| 6,090,037 A | 7/2000 | Gavish |
| 6,093,146 A | 7/2000 | Filangeri |
| 6,104,949 A | 8/2000 | Pitts Crick |
| 6,126,595 A | 10/2000 | Amano |
| 6,134,970 A | 10/2000 | Kumakawa |
| 6,135,970 A | 10/2000 | Kadhiresan |
| 6,157,850 A | 12/2000 | Diab |
| 6,168,568 B1 | 1/2001 | Gavriely |
| 6,198,394 B1 | 3/2001 | Jacobsen |
| 6,223,064 B1 | 4/2001 | Lynn |
| 6,239,706 B1 | 5/2001 | Yoshiike |
| 6,259,355 B1 | 7/2001 | Chaco |
| 6,261,238 B1 | 7/2001 | Gavriely |
| 6,290,654 B1 | 9/2001 | Karakasoglu |
| 6,325,761 B1 | 12/2001 | Jay |
| 6,352,517 B1 | 3/2002 | Flock |
| 6,368,287 B1 | 4/2002 | Hadas |
| 6,375,621 B1 | 4/2002 | Sullivan |
| 6,375,623 B1 | 4/2002 | Gavriely |
| 6,383,142 B1 | 5/2002 | Gavriely |
| 6,402,691 B1 | 6/2002 | Peddicord |
| 6,409,661 B1 | 6/2002 | Murphy |
| 6,436,057 B1 | 8/2002 | Goldsmith |
| 6,450,957 B1 | 9/2002 | Yoshimi |
| 6,454,719 B1 | 9/2002 | Greenhut |
| 6,468,234 B1 | 10/2002 | Van der Loos |
| 6,485,441 B2 | 11/2002 | Woodward |
| 6,498,652 B1 | 12/2002 | Varshneya |
| 6,512,949 B1 | 1/2003 | Combs |
| 6,517,497 B2 | 2/2003 | Rymut |
| 6,527,729 B1 | 3/2003 | Turcott |
| 6,544,173 B2 | 4/2003 | West |
| 6,544,174 B2 | 4/2003 | West |
| 6,547,743 B2 | 4/2003 | Brydon |
| 6,551,252 B2 | 4/2003 | Sackner |
| 6,561,978 B1 | 5/2003 | Conn |
| 6,579,232 B2 | 6/2003 | Sakamaki |
| 6,585,645 B2 | 7/2003 | Hutchinson |
| 6,589,188 B1 | 7/2003 | Street |
| 6,599,251 B2 | 7/2003 | Chen |
| 6,600,949 B1 | 7/2003 | Turcott |
| 6,616,606 B1 | 9/2003 | Petersen |
| 6,630,568 B1 | 10/2003 | Johnson |
| 6,631,281 B1 | 10/2003 | Kastle |
| 6,641,542 B2 | 11/2003 | Cho |
| 6,646,556 B1 | 11/2003 | Smith |
| 6,662,032 B1 | 12/2003 | Gavish |
| 6,666,830 B1 | 12/2003 | Lehrman |
| 6,719,708 B1 | 4/2004 | Jansen |
| 6,731,311 B2 | 5/2004 | Bufe |
| 6,745,060 B2 | 6/2004 | Diab |
| 6,751,498 B1 | 6/2004 | Greenberg |
| 6,752,766 B2 | 6/2004 | Kowallik |
| 6,754,516 B2 | 6/2004 | Mannheimer |
| 6,790,183 B2 | 9/2004 | Murphy |
| 6,821,258 B2 | 11/2004 | Reed |
| 6,822,564 B2 | 11/2004 | Al-Ali |
| 6,827,670 B1 | 12/2004 | Stark |
| 6,830,548 B2 | 12/2004 | Bonnet |
| 6,840,907 B1 | 1/2005 | Brydon |
| 6,856,141 B2 | 2/2005 | Ariav |
| 6,878,121 B2 | 4/2005 | Krausman |
| 6,893,404 B2 | 5/2005 | Ragnarsdottir |
| 6,955,647 B2 | 10/2005 | Rice |
| 6,980,679 B2 | 12/2005 | Jeung |
| 6,984,207 B1 | 1/2006 | Sullivan |
| 6,984,993 B2 | 1/2006 | Ariav |
| 6,988,989 B2 | 1/2006 | Weiner |
| 7,022,072 B2 | 4/2006 | Fox |
| 7,025,729 B2 | 4/2006 | de Chazal |
| 7,077,810 B2 | 7/2006 | Lange |
| 7,079,035 B2 | 7/2006 | Bock |
| 7,283,161 B2 | 10/2007 | Someya |
| 7,304,580 B2 | 12/2007 | Sullivan |
| 7,314,451 B2 | 1/2008 | Halperin |
| 7,390,299 B2 | 6/2008 | Weiner |
| 7,396,331 B2 | 7/2008 | Mack |
| 7,396,333 B2 | 7/2008 | Stahmann |
| 7,415,297 B2 | 8/2008 | Al-Ali |

(56) References Cited

U.S. PATENT DOCUMENTS

| | | |
|---|---|---|
| 7,428,468 B2 | 9/2008 | Takemura |
| 7,431,700 B2 | 10/2008 | Aoki |
| 7,433,827 B2 | 10/2008 | Rosenfeld |
| 7,439,856 B2 | 10/2008 | Weiner |
| 7,454,359 B2 | 11/2008 | Rosenfeld |
| 7,508,307 B2 | 3/2009 | Albert |
| 7,572,225 B2 | 8/2009 | Stahmann |
| 7,610,094 B2 | 10/2009 | Stahmann |
| 7,629,890 B2 | 12/2009 | Sullivan |
| 7,666,151 B2 | 2/2010 | Sullivan |
| 7,689,440 B2 | 3/2010 | Brown |
| 7,704,215 B2 | 4/2010 | Lewicke |
| 7,778,851 B2 | 8/2010 | Schoenberg |
| 7,860,583 B2 | 12/2010 | Condurso |
| 7,880,606 B2 | 2/2011 | Al-Ali |
| 7,896,813 B2 | 3/2011 | Sowelam |
| 7,938,782 B2 | 5/2011 | Stahmann |
| 7,952,475 B2 | 5/2011 | Ivanov |
| 7,959,574 B2 | 6/2011 | Bardy |
| 2002/0058155 A1 | 5/2002 | Guofang |
| 2002/0077554 A1 | 6/2002 | Schwartz |
| 2002/0082486 A1 | 6/2002 | Lavery |
| 2002/0086870 A1 | 7/2002 | Radulovacki |
| 2002/0097155 A1 | 7/2002 | Cassel |
| 2002/0099303 A1 | 7/2002 | Bardy |
| 2002/0106709 A1 | 8/2002 | Potts |
| 2002/0196148 A1 | 12/2002 | Nunome |
| 2003/0004403 A1 | 1/2003 | Drinan |
| 2003/0004423 A1 | 1/2003 | Lavie |
| 2003/0045806 A1 | 3/2003 | Brydon |
| 2003/0125612 A1 | 7/2003 | Fox |
| 2003/0135127 A1 | 7/2003 | Sackner |
| 2003/0139678 A1 | 7/2003 | Hoium |
| 2003/0144829 A1 | 7/2003 | Geatz |
| 2003/0153831 A1 | 8/2003 | Zumeris |
| 2003/0199945 A1 | 10/2003 | Ciulla |
| 2004/0010202 A1 | 1/2004 | Nakatani |
| 2004/0073098 A1 | 4/2004 | Geva |
| 2004/0082874 A1 | 4/2004 | Aoki |
| 2004/0111040 A1 | 6/2004 | Ni |
| 2004/0111045 A1 | 6/2004 | Sullivan |
| 2004/0116784 A1 | 6/2004 | Gavish |
| 2004/0133079 A1 | 7/2004 | Mazar |
| 2004/0210155 A1 | 10/2004 | Takemura |
| 2004/0225226 A1 | 11/2004 | Lehrman |
| 2004/0230105 A1 | 11/2004 | Geva |
| 2005/0043644 A1 | 2/2005 | Stahmann |
| 2005/0061315 A1 | 3/2005 | Lee |
| 2005/0074361 A1 | 4/2005 | Tanoshima |
| 2005/0080349 A1 | 4/2005 | Okada et al. |
| 2005/0085734 A1 | 4/2005 | Tehrani |
| 2005/0085866 A1 | 4/2005 | Tehrani |
| 2005/0096557 A1 | 5/2005 | Vosburgh |
| 2005/0119586 A1 | 6/2005 | Coyle |
| 2005/0124864 A1 | 6/2005 | Mack |
| 2005/0165284 A1 | 7/2005 | Gefen |
| 2005/0168341 A1 | 8/2005 | Reeder |
| 2005/0192508 A1 | 9/2005 | Lange |
| 2005/0201970 A1 | 9/2005 | Hu |
| 2005/0240091 A1 | 10/2005 | Lynn |
| 2006/0028350 A1 | 2/2006 | Bhai |
| 2006/0063982 A1 | 3/2006 | Sullivan |
| 2006/0084848 A1 | 4/2006 | Mitchnick |
| 2006/0089856 A1 | 4/2006 | Kadhiresan |
| 2006/0129047 A1 | 6/2006 | Ruotoistenmaki |
| 2006/0152378 A1 | 7/2006 | Lokhorst |
| 2006/0224076 A1 | 10/2006 | Lange |
| 2006/0241510 A1 | 10/2006 | Halperin |
| 2006/0258952 A1 | 11/2006 | Stahmann et al. |
| 2007/0024451 A1 | 2/2007 | Albert |
| 2007/0118054 A1 | 5/2007 | Pinhas |
| 2007/0139678 A1 | 6/2007 | Horita |
| 2007/0156031 A1 | 7/2007 | Sullivan |
| 2007/0177785 A1 | 8/2007 | Raffy |
| 2007/0249952 A1 | 10/2007 | Rubin |
| 2007/0257564 A1 | 11/2007 | Kitade |
| 2007/0276202 A1 | 11/2007 | Raisanen |
| 2008/0004904 A1 | 1/2008 | Tran |
| 2008/0005838 A1 | 1/2008 | Wan Fong |
| 2008/0114260 A1 | 5/2008 | Lange |
| 2008/0269625 A1 | 10/2008 | Halperin |
| 2008/0275349 A1 | 11/2008 | Halperin |
| 2009/0164239 A1 | 6/2009 | Hayter |
| 2009/0299229 A1 | 12/2009 | Johnson |
| 2010/0215074 A1 | 8/2010 | Lozinski |
| 2010/0217618 A1 | 8/2010 | Piccirillo |
| 2010/0234705 A1 | 9/2010 | Lynn |
| 2013/0174345 A1 | 7/2013 | Leu |

FOREIGN PATENT DOCUMENTS

| | | | |
|---|---|---|---|
| GB | 2329966 A1 | 4/1999 | |
| JP | 5323635 A2 | 12/1993 | |
| JP | 08-080285 A2 | 3/1996 | |
| JP | 08-225210 A2 | 9/1996 | |
| JP | 2001-037739 A2 | 2/2001 | |
| JP | 2001-145605 A1 | 5/2001 | |
| JP | 2001-327549 | 11/2001 | |
| JP | 2002-336207 A2 | 11/2002 | |
| JP | 2003-225210 A2 | 8/2003 | |
| JP | 2004-049388 A2 | 2/2004 | |
| JP | 2005-021450 A2 | 1/2005 | |
| JP | 2005-095307 A2 | 4/2005 | |
| JP | 2005-143661 A2 | 6/2005 | |
| JP | 2005-160876 A2 | 6/2005 | |
| JP | 2005-237479 | 9/2005 | |
| JP | 2005-279113 A2 | 10/2005 | |
| WO | 86/05965 A2 | 10/1986 | |
| WO | 96/08197 A2 | 3/1996 | |
| WO | 97/40748 A2 | 11/1997 | |
| WO | 99/04691 A2 | 2/1999 | |
| WO | 99/32537 A2 | 7/1999 | |
| WO | 01/80727 A2 | 1/2001 | |
| WO | 01/73718 A2 | 10/2001 | |
| WO | 03/013355 A2 | 2/2003 | |
| WO | 03/057025 A2 | 7/2003 | |
| WO | 2004006768 | 1/2004 | |
| WO | 2004/091378 A2 | 10/2004 | |
| WO | 2004/114193 A2 | 12/2004 | |
| WO | 2005/028029 A2 | 3/2005 | |
| WO | 2005/037077 A2 | 4/2005 | |
| WO | 2005/037366 A2 | 4/2005 | |
| WO | 2005/055824 A1 | 6/2005 | |
| WO | 2005/074361 A2 | 8/2005 | |
| WO | 2006/008743 A2 | 1/2006 | |
| WO | 2006/054306 A2 | 5/2006 | |
| WO | 2006/082589 A2 | 8/2006 | |
| WO | 2006/137067 A2 | 12/2006 | |
| WO | 2007/052108 A2 | 5/2007 | |
| WO | 2007081629 | 7/2007 | |
| WO | 2009/138976 A2 | 11/2009 | |
| WO | 2012/077113 A2 | 6/2012 | |

OTHER PUBLICATIONS

Chan, Marie et al., (2003) Prosafe, a multisensory remote monitoring system for the elderly or the handicapped, Independent Living for Persons with Disabilities and Elderly People: ICOST, 2003 1st International Conference on Smart Homes and Health Telematics.

Shinar, Z. et al., "Automatic detection of flow-wave-sleep using heart rate variability", Computers in cardiology, 28:593-596 (2001).

Shochat, Michael et al., "PedemaTOR: Innovative method for detecting pulmonary edema at the pre-clinical stage", http://www.isramed.info/rsmn_rabinovich/pedemator.htm (retrieved Aug. 22, 2005).

Sorjova, H. and Myllyla, R., "Noninvasive blood pressure measurement methods," Molecular and Quantum Acoustics. vol. 27, (2006).

Stegmaier-Stracca, Peter A. et al., Cough detection using fuzzy classification, Proceeding of the 1995 ACM Symposium on Applied Computing, Nashville, TN: 440-444.

Tamura T. et al., "A system for monitoring temperature distribution in bed and its application to the assessment of body movement", Physiological Measurement, Institute of Physics Publishing, Bristol, GB 1993; 14(1): 33-41.

(56) References Cited

OTHER PUBLICATIONS

Thorpe, C.W. et al., "Towards a quantitative description of asthmatic cough sounds", Eur Respir J, 5(6):685-692 (1992).
Van Der Loos, H.F. Michial et al., "Unobstrusive vital signs monitoring from a multisensory bed sheet", RESNA 2001, Reno, NV, Jun. 22-26, 2001, pp. 218-552.
Van Der Loos, H.F.M. et al., "Development of sensate and robotic bed technologies for vital signs monitoring and sleep quality improvement", Abstract, Autonomous Robots, 2003;15(1) http://www.ingenta.com/isi/searching/Expand/ingenta?pub=infobike://klu/auro/2003/00000015/00000001/05126829.
Van Hirtum, A. et al., "Autoregressive acoustical modeling of free field cough sound", Proc Int Conference on Acoustics, Speech and Signal Processing, vol. 1, pp. 493-496, Orlando, USA (2002).
Waris, M. et al., "A new method for automatic wheeze detection", Technology and Health Care,6:33-40 (1998).
Watanabe, et al., "Noncontact method for sleep stage estimation", IEEE transactions on Biomedical Engineering 10 (51):1735-1748 (2004).
Whitney, C.W., Gottlieb DJ, Redline S, Norman RG, Dodge RR, Shahar E, Surovec S and Nieto FJ, "Reliability of scoring respiratory disturbance indices and sleep staging," Sleep, 21(7):749-757 (Nov. 2, 1998).
Yongjoon et al., "Air matters sensor system with balancing tube for unconstrained measurement of respiration and heart beat movements", Physiol Meas, pp. 413-422 (2005).
Fitzpatrick, MF. et al., "Snoring, asthma and sleep distrurbances in Britain: a community based survey", ERS Journal Ltd., pp. 531-535 (1993).
Hark et al., "Spontaneous sigh rates during sedentary activity: watching television vs reading", Ann Allergy Asthma Immunol., 94(2):247-250 (2005).
Hogan, J., "Why don't nurses monitor the respiratory rates of patients?", Br J Nurs, 15(9):489-492 (2006).
Hori et al., "Proposed supplements and amendments to 'A Manual of Standardized Terminology, Techniques and Scoring System for Sleep Stages of Human Subjects', the Rechtschaffen & Kales (1968) standard", Psychiatry Clin Neurosci., 55(3):305-310 (2001).
Hsu, J.Y. et al., "Coughing frequency in patients with persistent cough; Assessment using a 24 hour ambulatory recorder", Eur Repir J, 7:1246-1253 (1994).
Hudgel et al., "Mechanics of the respiratory system and breathing pattern during sleep in normal humans", J Appl Physiol., 56(1): 133-137 (1984).
Jobanputra et al., "Management of acute asthma attacks in general practice", Br J Gen Pract., 41(351):410-413 (Oct. 1991).
Kandtelhardt, J.W., et al., "Breathing during REM and non-REM sleep: correlated versus uncorrelated behavior," 25 Physica. A., vol. 319, pp. 447-457, (2003).
Kap-Ho Seo et al., "Bed-type robotic system for the bedridden", advanced Intelligent Mechatronics, Proceedings, 2005 IEE/ASME International Conference on Monterey, CA Jul. 24-28, 2005. Piscataway, NK, USA pp. 1170-1175.
Kapsali et al., "Potent bronchoprotective effect of deep inspiration and its absence in asthma", J Appl Physiol., 89(2):711-720 (2000).
Katz et al., "Detection of preterm labor by ambulatory monitoring of uterine activity: a preliminary report", Obstet Gynecol., 68(6):773-778 (Dec. 1986).
Korpas, J. et al., "Analysis of the cough sound: an overview", Pulmonary Pharmacology, 9:261-268 (1996).
Li, Q., et al., "Mixture density estimation," Advances in neural information processing systems, vol. 12, pp. 279-285, MIT press, (2000).
Lim TO. et al., "Morbidity associated with asthma and audit of asthma treatment in out-patient clinics", Singapore Med J., 33(2):174-176 (1992).
Madge, PJ et al., "Home nebuliser use in children with asthma in two Scottish Health Board Areas", Scott Med J., 40(5):141-143 (1995).
Mintzer, Rich, "What the teacher should know about asthma attacks", http://www.familyeducation.com/article/print/0,1303,65-415,00.html?obj_gra (retrieved Feb. 22, 2007).

O'Connor, CJ et al, "Identification of endotracheal tube malpositions using computerized analysis of breath sounds via electronic stethoscopes," Anesth Analg, 101:735-739 (2005).
Pirrila, P. et al., "Objective assessment of cough", Eur respire J, 8:1949-1956 (1995).
Plaut, Thomas F., "Tracking and treating asthma in young children", J Respir Dis Pediatrician, 5(2): 67-72 (2003).
Poteet, Jackie, "Asthma". http://www.nku.edu/~rad350/asthmajp.html (retrieved Jun. 25, 2012).
Salmi et al., "Automatic analysis of sleep records with static charge sensitive bed", Electroencephalography and Clinical Neurophysiology, pp. 84-87 (1986).
Salmi, Tapani et al., "Long-term recording and automatic analysis of cough using filtered acoustic signals and movements on static charge sensitive bed", Chest, 94: 970-975 (1988).
Schwartz, "Estimating the dimension of a model", The Annals of Statistics, 6(2):461-464 (1978).
"British guidelines on management of asthma: a national clinical guidline", British Thoracic Society, Scottish Intercollegiate Guidelines Network, Revised edition, Apr. 2004, pp. 1-92.
"Does my child have asthma?" Solano Asthma Coalition, American Lung Association of the East Bay (http://www.alaebay.org/misc_pdf/solano_asthma_coalition_child_asthma.pdf) (2001).
"Managing asthma", http://kidshealth.org/pageManager.jsp?dn=KidsHealth&lic=1&ps=107&cat_id=143&article_set=2 (Aug. 2011).
"Medical Mutual clinical practice guidelines for asthma: 2004, "Medical Mutual (Cleveland, OH), (http://www.medmutual.com/provider/pdf/resources/asthma4.pdf).
"Non-invasive fiber-optic sensor technology for monitoring sleep apnea and SIDS", http://www.kidsource.com/products/fiber.optic.SIDS.html (Retrieved Apr. 18, 2005).
"Peak flow learning center", http://www.njc.org/disease-info/diseases/asthma/living/tools/peak/index/aspx (Retrieved Feb. 22, 2007).
"Signs and symptoms of asthma", http://www.indianchestsociety.org/symptomsofasthma.htm (Retrieved Feb. 22, 2007).
Alihanka, J. et al., "A new method for long-term monitoring ballistocardiogram, heart rate, and respiration", AM J Physiol Regul Integ Comp Physiol, 240: 384-392 (1981).
Alihanka, J. et al., "A static charge sensitive bed. A new method for recording body movement during sleep", Electroencephalography and Clinical Neurophysiology, 46(6):731-734 (1979).
Ancoli-Israel S. et al., "The role of actigraphy in the study of sleep and circadian rhythms", Sleep, 26(3):342-392 (2003).
Baren, Jill M. et al., "Current Concepts in the ED treatment of pediatric Asthma", Respiratory Medicine Consensus Reports (Thomson American Health Consultants, Dec. 28, 2003), pp. 1.12.
Bentur, L. et al., "Wheeze monitoring in children for assessment of nocturnal asthma and response to therapy", Eur respire J, 21:621-626 (2003).
Bilmes et al., "A gentle tutorial of the EM algorithm and its application to parameter estimation for caussian mixture and hidden markov models", Internation Computer Science Institut, pp. 1-13 (1998).
Brenner, Barry E. et al., "The clinical presentation of acute ashma in adults and children", In Brenner, BE, ed. Emergency Asthma (New York: Marcel Dekker 1994; pp. 201-232.
Butter CD. et al., "Fiber optics strain gauge",. Appl Opt., 17(18): 2867-2869 (1978).
Chaboyer, W. et al., "Predictors of adverse events in patients after discharge from the intensive care unit", Am J Crit Care, 17:255-263 (2008).
Chang, A.B. et al., "Cough, airway inflammation, and mild asthma exacerbation", Archives of disease in childhood, 86:207-215 (2002).
Delmore, G. et al., "The role of augmented breaths (sighs) in bronchial asthma attacks", Pflugers Arch., 372(1):1-6 (1977).
Dempster, AP. et al., "Maximum likelihood from incomplete data via the EM algorithm", Journal of the Royal Statistical Society, 39(1):1-38 (1977).
Fieselmann, JF et al., "Respiratory rate predicts cardiopulmonary arrest for internal medicine inpatients", J Gen Intern Med, 8(7):354-360 (1993).

(56) References Cited

OTHER PUBLICATIONS

Fitzpatrick, MF. et al., "Morbidity in nocturnal asthma: sleep quality and daytime cognitive performance", Thorax., 46(8):569-573 (1991).
International Search Report of PCT/IL2011/050045 dated Jul. 13, 2012.
Oppenheim, A., and Schafer, R., "Discrete-Time Signal Processing", Prentice5' Hall, 1989, pp. 311-312 (1989).
Staderini, Enrico M., "UWB Radars in Medicine", IEEE Aerospace and Electronic Systems Magazine, 17(1)13-18 (2002).
Yien, HW et al., "Spectral analysis of systemic arterial pressure and heart rate signals as a prognostic tool for the prediction of patient outcome in the intensive care unit", Crit Care Med., 25(2):258-266 (1997).
Corresponding European Patent Application No. 12168737 European Search Report Sep. 3, 2012.
European Search Report for European Patent No. 09746270.9 dated Apr. 8, 2013.
Mack et al "Non-Invasive Analysis of Physiological Signals (NAPS): A Low-Cost, Passive Monitor for Sleep Quality", University of Virginia Health System, pp. 1-9 (Oct. 2002).
"Breathing easier with asthma", pp. 1-46, Intermountain Health Care, (2003).
International Search Report for PCT/IL2013/050283 dated Aug. 28, 2013.

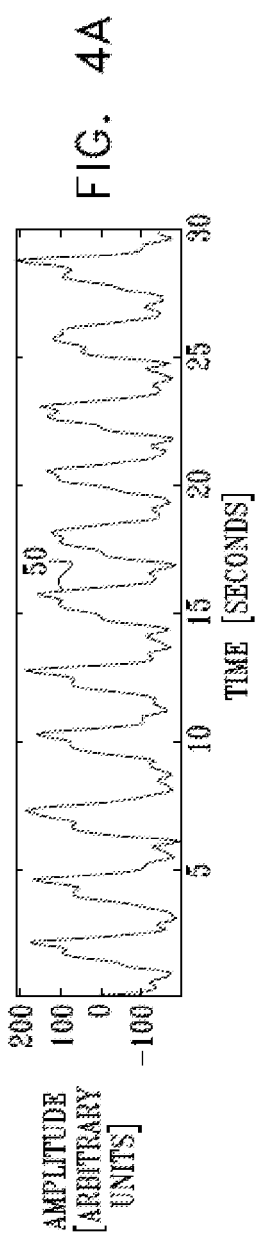
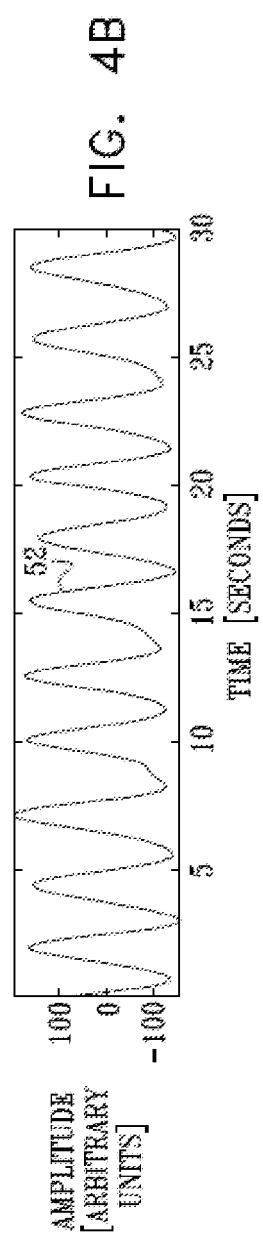
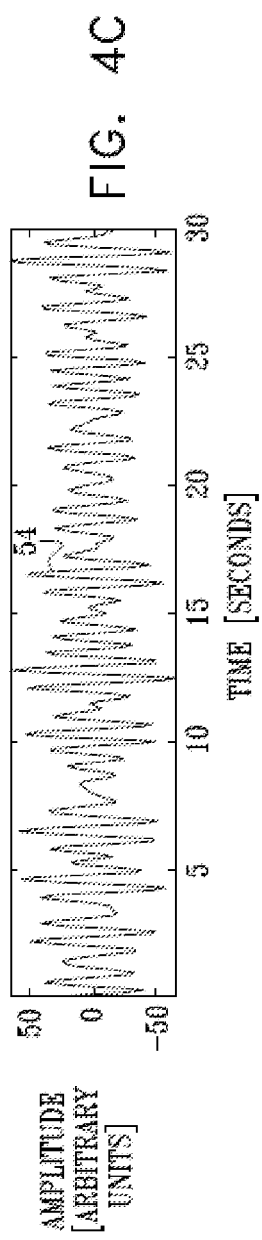

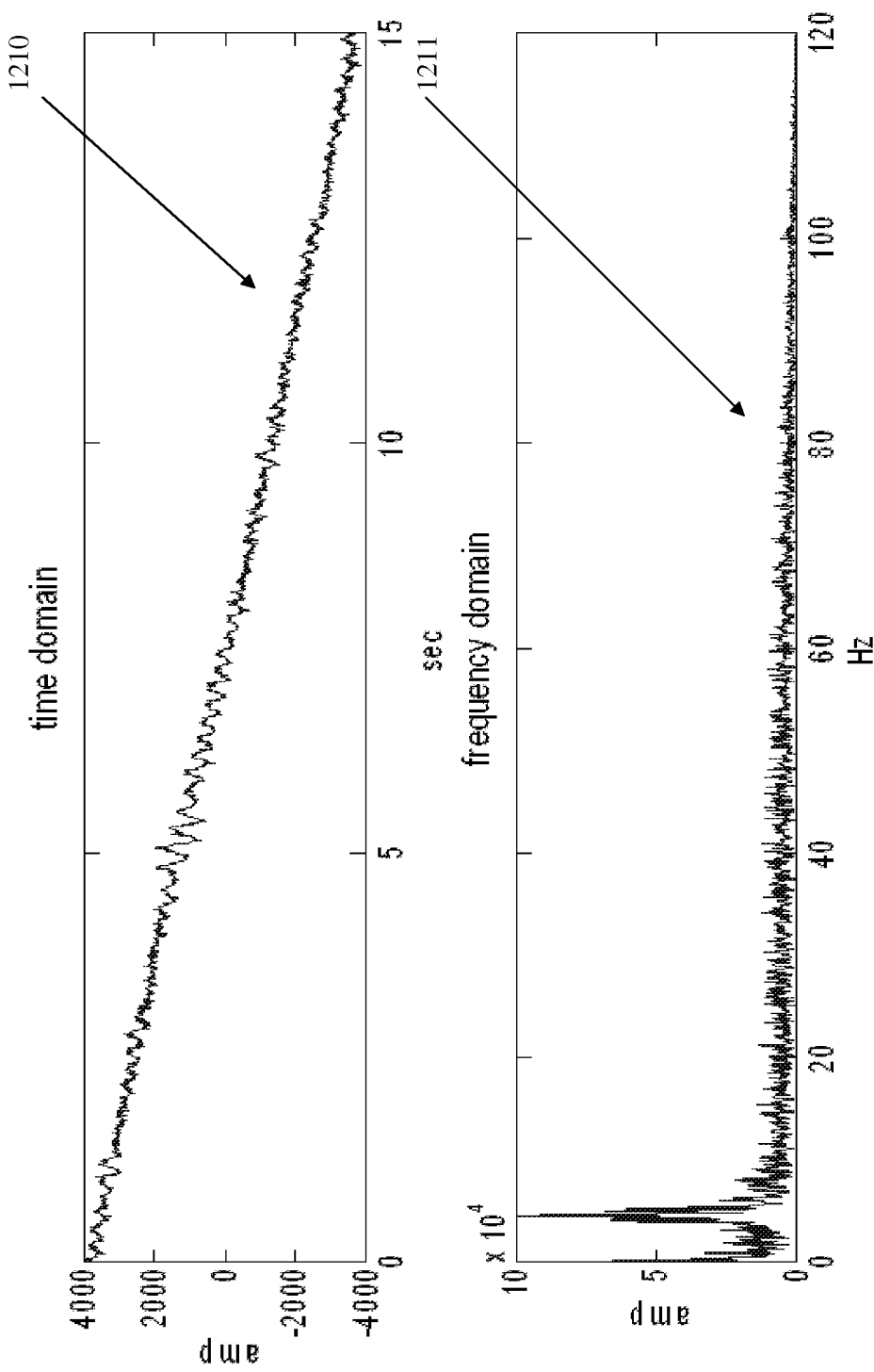

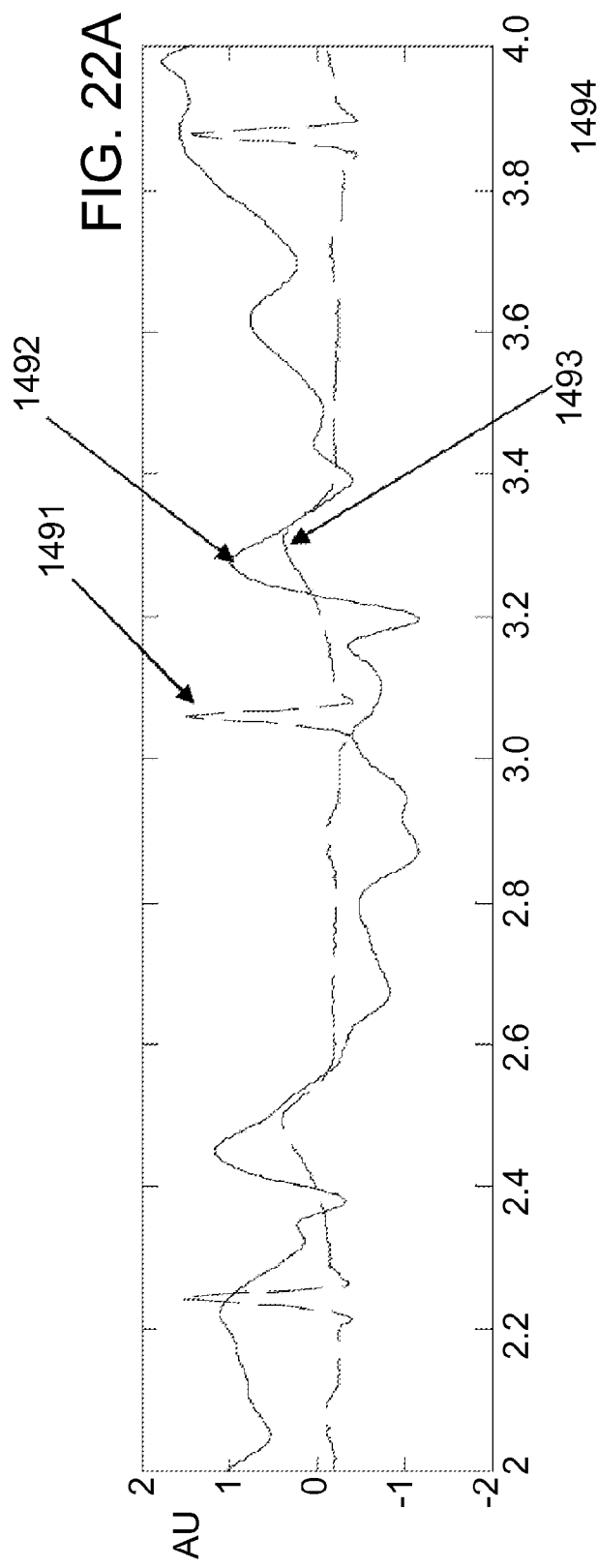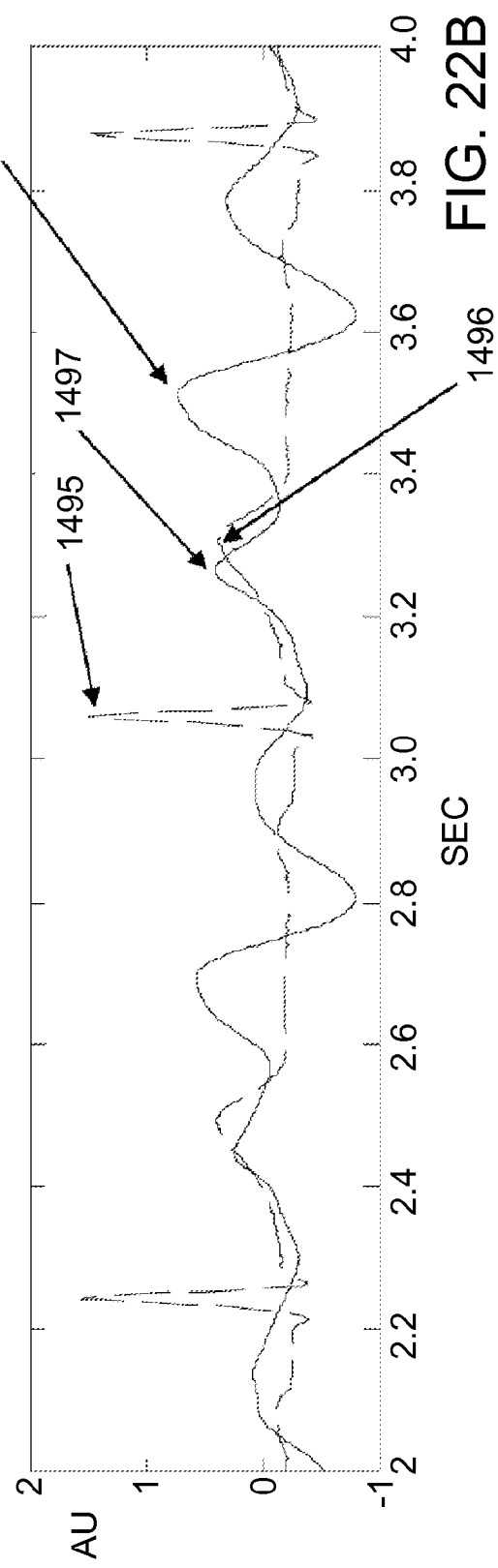

MONITORING, PREDICTING AND TREATING CLINICAL EPISODES

CROSS-REFERENCES TO RELATED APPLICATIONS

The present application is a continuation-in-part of PCT Application PCT/IL2009/000473, filed May 10, 2009, which:
(a) claims priority from:
U.S. Provisional Application 61/052,395, filed May 12, 2008,
U.S. Provisional Application 61/054,754, filed May 20, 2008,
U.S. Provisional Application 61/082,510, filed Jul. 22, 2008,
U.S. Provisional Application 61/103,276, filed Oct. 7, 2008,
U.S. Provisional Application 61/141,677, filed Dec. 31, 2008, and
U.S. Provisional Application 61/144,743 filed Jan. 15, 2009; and
(b) is a continuation-in-part of U.S. patent application Ser. No. 12/113,680, filed May 1, 2008, which claims the benefit of:
U.S. Provisional Application 60/924,181, filed May 2, 2007;
U.S. Provisional Application 60/924,459, filed May 16, 2007;
U.S. Provisional Application 60/935,194, filed Jul. 31, 2007;
U.S. Provisional Application 60/981,525, filed Oct. 22, 2007;
U.S. Provisional Application 60/983,945, filed Oct. 31, 2007;
U.S. Provisional Application 60/989,942, filed Nov. 25, 2007;
U.S. Provisional Application 61/028,551, filed Feb. 14, 2008; and
U.S. Provisional Application 61/034,165, filed Mar. 6, 2008.

The present application claims priority from U.S. Provisional Application 61/257,473, filed Nov. 3, 2009.

All of the above-referenced applications are incorporated herein by reference.

FIELD OF THE INVENTION

The present invention relates generally to monitoring patients and predicting and monitoring abnormal physiological conditions and treating those conditions, and specifically to methods and apparatus for predicting and monitoring abnormal physiological conditions by non-contact measurement and analysis of characteristics of physiological and/or physical parameters.

BACKGROUND OF THE INVENTION

Chronic diseases are often expressed by episodic worsening of clinical symptoms. Preventive treatment of chronic diseases reduces the overall dosage of required medication and associated side effects, and lowers mortality and morbidity. Generally, preventive treatment should be initiated or intensified as soon as the earliest clinical symptoms are detected, in order to prevent progression and worsening of the clinical episode and to stop and reverse the pathophysiological process. Therefore, the ability to accurately monitor pre-episodic indicators increases the effectiveness of preventive treatment of chronic diseases.

Many chronic diseases cause systemic changes in vital signs, such as breathing and heartbeat patterns, through a variety of physiological mechanisms. For example, common respiratory disorders, such as asthma, chronic obstructive pulmonary disease (COPD), sleep apnea and cystic fibrosis (CF), are direct modifiers of breathing and/or heartbeat patterns. Other chronic diseases, such as diabetes, epilepsy, and certain heart conditions (e.g., congestive heart failure (CHF)), are also known to modify cardiac and breathing activity. In the case of certain heart conditions, such modifications typically occur because of pathophysiologies related to fluid retention and general cardiovascular insufficiency. Other signs such as coughing and sleep restlessness are also known to be of importance in some clinical situations.

Many chronic diseases induce systemic effects on vital signs. For example, some chronic diseases interfere with normal breathing and cardiac processes during wakefulness and sleep, causing abnormal breathing and heartbeat patterns.

Breathing and heartbeat patterns may be modified via various direct and indirect physiological mechanisms, resulting in abnormal patterns related to the cause of modification. Some respiratory diseases, such as asthma, and some heart conditions, such as CHF, are direct breathing modifiers. Other metabolic abnormalities, such as hypoglycemia and other neurological pathologies affecting autonomic nervous system activity, are indirect breathing modifiers.

The following patents and patent application publications, all of which are incorporated herein by reference, may also be of interest:
U.S. Pat. No. 4,657,026 to Tagg;
U.S. Pat. No. 5,235,989 to Zomer;
U.S. Pat. No. 5,540,734 to Zabara;
U.S. Pat. No. 5,743,263 to Baker;
U.S. Pat. No. 5,957,861 to Combs;
U.S. Pat. No. 5,964,720 to Pelz;
U.S. Pat. No. 6,134,970 to Kumakawa;
U.S. Pat. No. 6,375,621 to Sullivan;
U.S. Pat. No. 6,383,142 to Gavriely;
U.S. Pat. No. 6,436,057 to Goldsmith et al.;
U.S. Pat. No. 6,856,141 to Ariav;
U.S. Pat. No. 6,980,679 to Jeung;
U.S. Pat. No. 6,984,207 to Sullivan;
U.S. Pat. No. 6,984,993 to Ariav;
U.S. Pat. No. 7,025,729 to de Chazal;
US Patent Application 2003/0045806 to Brydon;
US Patent Application 2005/0119586 to Coyle et al.;
US Patent Application 2006/0084848 to Mitchnick;
US Patent Application 2007/0156031 to Sullivan;
US Patent Application Publication 2007/0249952 to Rubin et al.; and
US Patent Application Publication 2008/0005838 to Wan Fong et al.

The following articles, which are incorporated herein by reference, may also be of interest:
Alihanka J., et al., "A new method for long-term monitoring of the ballistocardiogram, heart rate, and respiration," Am J Physiol Regul Integr Comp Physiol 240:384-392 (1981).
Bentur, L. et al., "Wheeze monitoring in children for assessment of nocturnal asthma and response to therapy," Eur Respir J 21(4):621-626 (2003).
Bilmes, J., "A gentle tutorial on the EM algorithm and its application to parameter estimation for Gaussian mixture and hidden Markov models," Technical report, University of Berkeley, ICSI-TR-97-021, 1997.

Chang, A. B. et al., "Cough, airway inflammation, and mild asthma exacerbation," Archives of Disease in Childhood 86:270-275 (2002).

Dempster, A. P., N. M. Laird, and D. B. Rubin, "Maximum likelihood from incomplete data via the EM algorithm," Journal of the royal statistical society, vol. 39 B, pp. 1-38, 1977.

Hirtum, A.; Berckmans, D.; Demuynck, K.; and Compernolle, D., "Autoregressive Acoustical Modelling of Free Field Cough Sound," Proc. International Conference on Acoustics, Speech and Signal Processing, volume I, pages 493-496, Orlando, U.S.A., May 2002.

Hsu, J. Y., et al., "Coughing frequency in patients with persistent cough: assessment using a 24 hour ambulatory recorder," Eur Respir J 7:1246-1253 (1994).

Hudgel, D. W., R. J. Martin, B. Johnson, and P. Hill, "Mechanics of the respiratory system during sleep in normal humans," J. Appl. Physiol., vol. 5, pp. 133-137, 1984.

Kandtelhardt, J. W., T. Penzel, S. Rostig, H. F. Becker, S. Halvin, and A. Bunde, Breathing during REM and non-REM sleep: correlated versus uncorrelated behavior," Physica. A., vol. 319, pp. 447-457, 2003.

Li, Q. and A. Barron, "Mixture density estimation," *Advances in neural information processing systems*, vol. 12, pp. 279-285, MIT press, 2000.

Mack, D., et al., "Non-invasive analysis of physiological signals: NAPS: A low cost, passive monitor for sleep quality and related applications," University of Virginia Health System (undated).

O'Connor CJ et al, "Identification of endotracheal tube malpositions using computerized analysis of breath sounds via electronic stethoscopes," Anesth Analg 2005; 101:735-9.

Oppenheim, A. V., and R. W. Schafer, *Discrete-Time Signal Processing*, Prentice-Hall, 1989, pp. 311-312.

Rechtschaffen A., Kales A. *Manual of standardized terminology, techniques and scoring system for sleep for sleep stages of human subjects*. Los Angeles: UCLA brain information services/brain research institute, 1968.

Salmi, T., et al., "Automatic analysis of sleep records with static charge sensitive bed," Electroencephalography and Clinical Neurophysiology 64:84-87 (1986).

Schwarz, G., "Estimating the dimension of a model," *Annals of statistics*, vol. 6, pp. 461-464, 1978.

Sorvoja, H. and Myllylä, R., "Noninvasive blood pressure measurement methods," Molecular and Quantum Acoustics. vol. 27, 2006.

Van der Loos, H. F. M., et al., "Unobtrusive vital signs monitoring from a multisensor bed sheet," RESNA'2001, Reno, Nev., Jun. 22-26, 2001.

Waris, M., et al., "A new method for automatic wheeze detection," Technol Health Care 6(1):33-40 (1998).

Watanabe, T., et al., "Noncontact Method for Sleep Stage Estimation," IEEE Transactions on Biomedical Engineering, No 10, Vol. 51, October 2004.

Whitney, C. W., Gottlieb D J, Redline S, Norman R G, Dodge R R, Shahar E, Surovec S and Nieto F J, "Reliability of scoring respiratory disturbance indices and sleep staging," Sleep, 1998, Nov. 2; 21(7): 749-757.

Yongjoon, C., et al., "Air mattress sensor system with balancing tube for unconstrained measurement of respiration and heart beat movements", 2005 Physiol. Meas. 26 413-422.

U.S. Pat. No. 7,077,810 to Lange et al., which is assigned to the assignee of the present application and is incorporated herein by reference, describes a method for predicting an onset of a clinical episode, the method including sensing breathing of a subject, determining at least one breathing pattern of the subject responsively to the sensed breathing, comparing the breathing pattern with a baseline breathing pattern, and predicting the onset of the episode at least in part responsively to the comparison.

U.S. Provisional Patent Applications 60/541,779, 60/674,382 and 60/692,105, PCT Publication WO 05/074361 to Lange et al., US Patent Application Publication 2006/0241510 to Halperin et al., US Patent Application 2008/0275349 submitted by Halperin et al. on May 1, 2008 assigned to the assignee of the present invention and US Patent Application Publication 2007/0118054 to Pinhas et al., all of which are assigned to the assignee of the present application and incorporated herein by reference, describe various methods and systems for clinical episode prediction and monitoring.

The inclusion of the foregoing references in this Background section does not imply that they constitute prior art or analogous art with respect to the invention disclosed herein.

SUMMARY OF THE INVENTION

Embodiments of the present invention provide methods and systems for monitoring patients for the occurrence or recurrence of a physiological event, for example, a chronic illness or ailment. This monitoring assists the patient or healthcare provider in treating the ailment or mitigating the effects of the ailment. Embodiments of the present invention provide techniques for monitoring vital and non-vital signs using automated sensors and electronic signal processing, in order to detect and characterize the onset of a physiological event, and, for some applications, to treat the event, such as with therapy or medication.

There is therefore provided, in accordance with some applications of the present invention, apparatus for use with a subject who is undergoing respiration, the apparatus including:

a motion sensor configured to sense motion of a subject;
a control unit including:
    a breathing pattern analysis unit that is configured to analyze components of the sensed motion that result from the subject's respiration, the breathing pattern analysis unit including:
        double-movement-respiration-cycle-pattern-identification functionality that is configured to designate respiration cycles as being double-movement-respiration-cycles by determining that the cycles define two subcycles;
        double-movement-respiration-cycle-event-identification functionality configured to identify a double-movement-respiration-cycle event by detecting that the subject has undergone a plurality of double-movement-respiration-cycles; and
    output-generation functionality configured to generate an output that is indicative of the subject having used accessory muscles in breathing, in response to identification of the double-movement-respiration-cycle event; and
a user interface configured to display the output.

For some applications, the sensor is configured to sense motion of the subject without contacting the subject or clothes the subject is wearing.

For some applications, the sensor is configured to sense motion of the subject without contacting or viewing the subject or clothes the subject is wearing.

For some applications, the double-movement-respiration-cycle-pattern-identification functionality is configured to distinguish between a first cycle that defines two subcycles, and a second cycle that does not define two subcycles, even if the first and second cycles have substantially similar amplitudes to one another.

For some applications, the double-movement-respiration-cycle-pattern-identification functionality is configured to distinguish between a first cycle that defines two subcycles, and a second cycle that does not define two subcycles, even if the first and second cycles have substantially similar frequencies to one another.

For some applications, the double-movement-respiration-cycle-pattern-identification functionality is configured to determine that a cycle defines two subcycles at least partially in response to an amplitude of the cycle.

For some applications, the double-movement-respiration-cycle-pattern-identification functionality is configured to determine that a cycle defines two subcycles at least partially in response to a frequency of the cycle.

For some applications, the double-movement-respiration-cycle-pattern-identification functionality is configured to determine that a cycle defines two subcycles by identifying two adjacent peak and trough sets of a respiration motion signal of the subject, the sets being substantially asymmetrical with respect to one another, and, in response thereto, designating the adjacent peak and trough sets as being two subcycles of a single respiration cycle.

For some applications, the double-movement-respiration-cycle-pattern-identification functionality is configured to determine that a cycle defines two subcycles at least partially in response to a slope of a respiration motion signal of the subject.

For some applications, the double-movement-respiration-cycle-event-identification functionality is configured to identify the double-movement-respiration-cycle event by detecting that at least 30% of respiration cycles of the subject over a period of time of at least one minute define two subcycles.

For some applications, the double-movement-respiration-cycle-event-identification functionality is configured to identify the double-movement-respiration-cycle event by detecting that at least 60% of respiration cycles of the subject over the period of time of at least one minute define two subcycles.

For some applications, the double-movement-respiration-cycle-event-identification functionality is configured to identify the double-movement-respiration-cycle event by detecting that at least 30% of respiration cycles of the subject over the period of time of at least ten minutes define two subcycles.

For some applications, the double-movement-respiration-cycle-event-identification functionality is configured to identify the double-movement-respiration-cycle event by detecting that at least 30% of respiration cycles of the subject over the period of time of at least 30 minutes define two subcycles.

For some applications, the double-movement-respiration-cycle-event-identification functionality is configured to identify the double-movement-respiration-cycle event by detecting that at least 30% of respiration cycles of the subject over the period of time of at least 60 minutes define two subcycles.

For some applications, the control unit is configured to predict an onset of a clinical condition of the subject in response to the double-movement-respiration-cycle-event-identification functionality identifying the double-movement-respiration-cycle event.

For some applications, the control unit is configured to predict the onset of the clinical condition by predicting the onset of a clinical condition selected from the group consisting of: elevated heart rate and elevated respiration rate.

For some applications, the control unit is configured to predict the onset of the clinical condition at least 30 minutes before the onset of the clinical condition.

There is further provided, in accordance with some applications of the present invention, apparatus for use with a subject who is undergoing respiration, the apparatus including:
a motion sensor configured to sense motion of a subject;
a control unit including:
a breathing pattern analysis unit that is configured to analyze components of the sensed motion that result from the subject's respiration, the breathing pattern analysis unit including:
double-movement-respiration-cycle-pattern-identification functionality that is configured to designate respiration cycles as being double-movement-respiration-cycles by determining that the cycles define two subcycles; and
double-movement-respiration-cycle-event-identification functionality configured to identify a double-movement-respiration-cycle event by detecting that the subject has undergone a plurality of double-movement-respiration-cycles; and
output-generation functionality configured to generate an output that is indicative of an onset of an episode of respiratory distress, in response to the double-movement-respiration-cycle event; and
a user interface configured to display the output.

For some applications, the output-generation functionality is configured to generate the output by generating an output that is indicative of the onset of an elevated respiration rate.

For some applications, the double-movement-respiration-cycle-event-identification functionality is configured to predict the onset of the respiratory distress at least 30 minutes before the onset of the respiratory distress, in response to the double-movement-respiration-cycle event, and the output-generation functionality is configured to generate the output, in response thereto.

For some applications, the output-generation functionality is further configured to generate an output that is indicative of the onset of an elevated heart rate of the subject, in response to the double-movement-respiration-cycle event.

For some applications, the sensor is configured to sense motion of the subject without contacting the subject or clothes the subject is wearing.

For some applications, the sensor is configured to sense motion of the subject without contacting or viewing the subject or clothes the subject is wearing.

For some applications, the double-movement-respiration-cycle-pattern-identification functionality is configured to distinguish between a first cycle that defines two subcycles, and a second cycle that does not define two subcycles, even if the first and second cycles have substantially similar amplitudes to one another.

For some applications, the double-movement-respiration-cycle-pattern-identification functionality is configured to distinguish between a first cycle that defines two subcycles, and a second cycle that does not define two subcycles, even if the first and second cycles have substantially similar frequencies to one another.

For some applications, the double-movement-respiration-cycle-pattern-identification functionality is configured to determine that a cycle defines two subcycles at least partially in response to an amplitude of the cycle.

For some applications, double-movement-respiration-cycle-pattern-identification functionality is configured to determine that a cycle defines two subcycles at least partially in response to a frequency of the cycle.

For some applications, the double-movement-respiration-cycle-pattern-identification functionality is configured to determine that a cycle defines two subcycles by identifying two adjacent peak and trough sets of a respiration motion signal of the subject that are substantially asymmetrical with respect to one another, and, in response thereto, designating the adjacent peak and trough sets as being two subcycles of a single respiration cycle.

For some applications, the double-movement-respiration-cycle-pattern-identification functionality is configured to determine that a cycle defines two subcycles at least partially in response to a slope of a respiration motion signal of the subject.

For some applications, the double-movement-respiration-cycle-event-identification functionality is configured to identify the double-movement-respiration-cycle event by detecting that at least 30% of respiration cycles of the subject over a period of time of at least one minute define two subcycles.

For some applications, the double-movement-respiration-cycle-event-identification functionality is configured to identify the double-movement-respiration-cycle event by detecting that at least 60% of respiration cycles of the subject over the period of time of at least one minute define two subcycles.

For some applications, the double-movement-respiration-cycle-event-identification functionality is configured to identify the double-movement-respiration-cycle event by detecting that at least 30% of respiration cycles of the subject over the period of time of at least ten minutes define two subcycles.

For some applications, the double-movement-respiration-cycle-event-identification functionality is configured to identify the double-movement-respiration-cycle event by detecting that at least 30% of respiration cycles of the subject over the period of time of at least 30 minutes define two subcycles.

For some applications, the double-movement-respiration-cycle-event-identification functionality is configured to identify the double-movement-respiration-cycle event by detecting that at least 30% of respiration cycles of the subject over the period of time of at least 60 minutes define two subcycles.

There is additionally provided, in accordance with some applications of the present invention, a method for use with a subject who is undergoing respiration, the method including:
  sensing motion of a subject;
  analyzing components of the sensed motion that result from the subject's respiration, by:
    designating respiration cycles as being double-movement-respiration-cycles, by determining that the cycles define two subcycles;
    identifying a double-movement-respiration-cycle event by detecting that the subject has undergone a plurality of double-movement-respiration-cycles; and
    in response to identification of the double-movement-respiration-cycle event, generating an output that is indicative of the subject having used accessory muscles in breathing.

There is further provided, in accordance with some applications of the present invention, a method for use with a subject who is undergoing respiration, the method including:
  sensing motion of a subject;
  analyzing components of the sensed motion that result from the subject's respiration, by:
    designating respiration cycles as being double-movement-respiration-cycles by determining that the cycles define two subcycles;
    identifying a double-movement-respiration-cycle event by detecting that the subject has undergone a plurality of double-movement-respiration-cycles; and
    in response to identifying the double-movement-respiration-cycle event, generating an output that is indicative of an onset of an episode of respiratory distress.

BRIEF DESCRIPTION OF THE DRAWINGS

FIGS. 4A-C are graphs illustrating motion signals, measured in accordance with an embodiment of the present invention;

FIG. 5 is a schematic illustration of an exemplary mechanical signal, measured in accordance with an embodiment of the present invention;

FIGS. 22A-B are schematic illustrations of the ECG signal (dashed line) and corresponding signal from a contactless motion sensor placed under the area of the chest (22A), and the same ECG signal and the corresponding signal from contactless motion sensor placed under the area of the legs (20B), measured in accordance with an embodiment of the present invention measured on a subject;

DETAILED DESCRIPTION OF EMBODIMENTS

Figure 1:
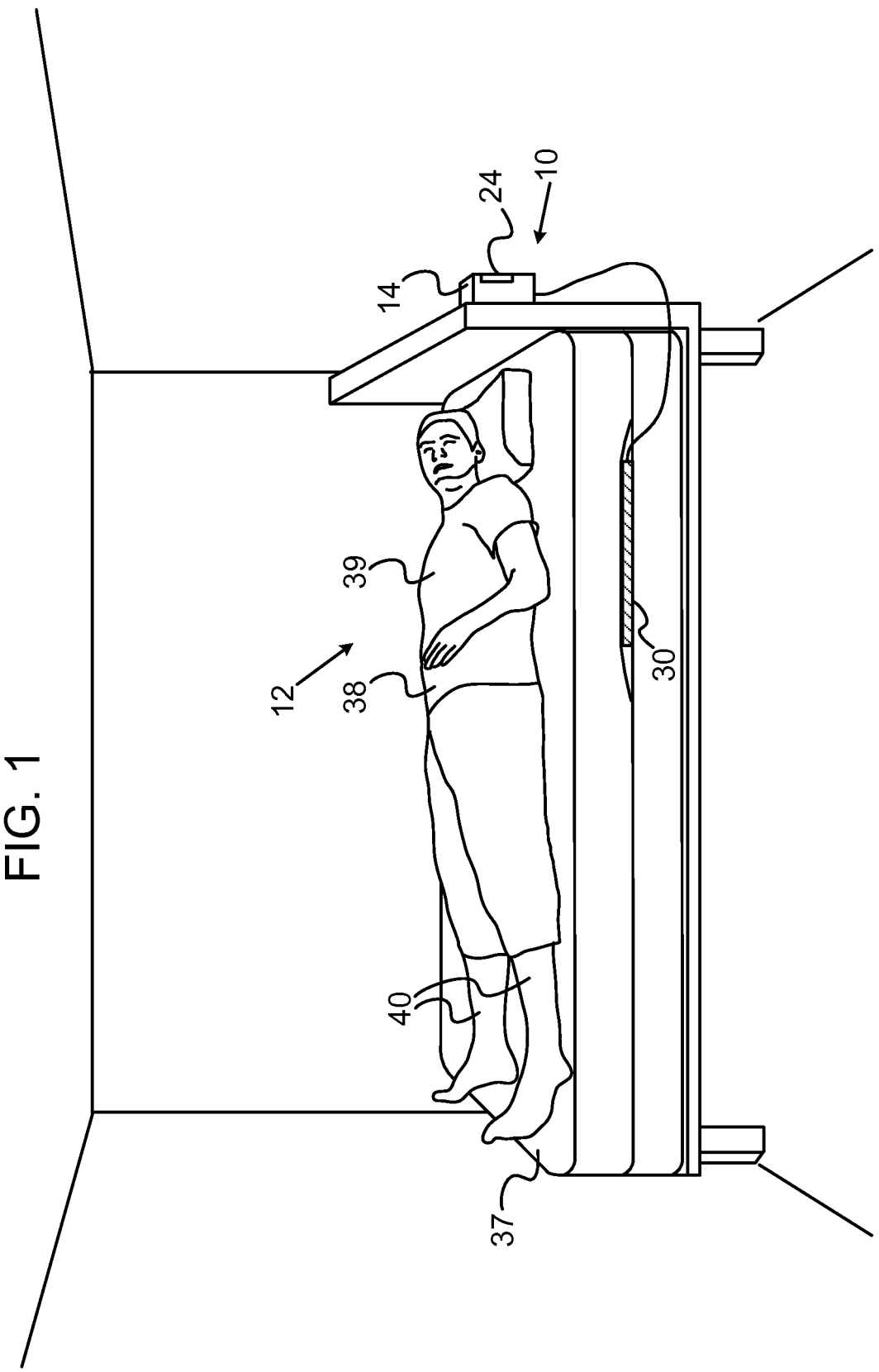
FIG. 1 is a schematic illustration of a system for monitoring a chronic medical condition of a subject, in accordance with an embodiment of the present invention.

FIG. 1 is a schematic illustration of a system 10 for monitoring a chronic medical condition of a subject 12, in accordance with an embodiment of the present invention. System 10 typically comprises a motion sensor 30, a control unit 14, and a user interface (U/I) 24. For some applications, user interface 24 is integrated into control unit 14, as shown in the figure, while for other applications, the user interface and the control unit are separate units. For some applications, motion sensor 30 is integrated into control unit 14, in which case user interface 24 is either also integrated into control unit 14 or remote from control unit 14.

In some embodiments of the present invention, motion sensor 30 is a "non-contact sensor," that is, a sensor that does not contact the body of subject 12 or clothes subject 12 is wearing. In other embodiments, motion sensor 30 does contact the body of subject 12 or clothes subject 12 is wearing. In the former embodiments, because motion sensor 30 does not come in contact with subject 12, motion sensor 30 detects motion of subject 12 without discomforting or inconveniencing subject 12. For some applications, motion sensor 30 performs sensing without the knowledge of subject 12, and even, for some applications, without the consent of subject 12. For some applications, motion sensor 30 does not have a direct line of sight with subject 12 or the clothes subject 12 is wearing.

Motion sensor 30 may comprise a ceramic piezoelectric sensor, vibration sensor, pressure sensor, or strain sensor, for example, a strain gauge, configured to be installed under a reclining surface 37, and to sense motion of subject 12. The motion of subject 12 sensed by sensor 30, during sleep, for example, may include regular breathing movement, heartbeat-related movement, and other, unrelated body movements, as discussed below, or combinations thereof. For some applications, sensor 30 comprises a standard communication interface (e.g. USB), which enables connection to standard monitoring equipment.

All experimental results presented in the present application were measured using one or more piezoelectric sensors. Nevertheless, the scope of the present invention includes performing measurements with other motion sensors 30, such as other pressure gauges or accelerometers.

Figure 2:
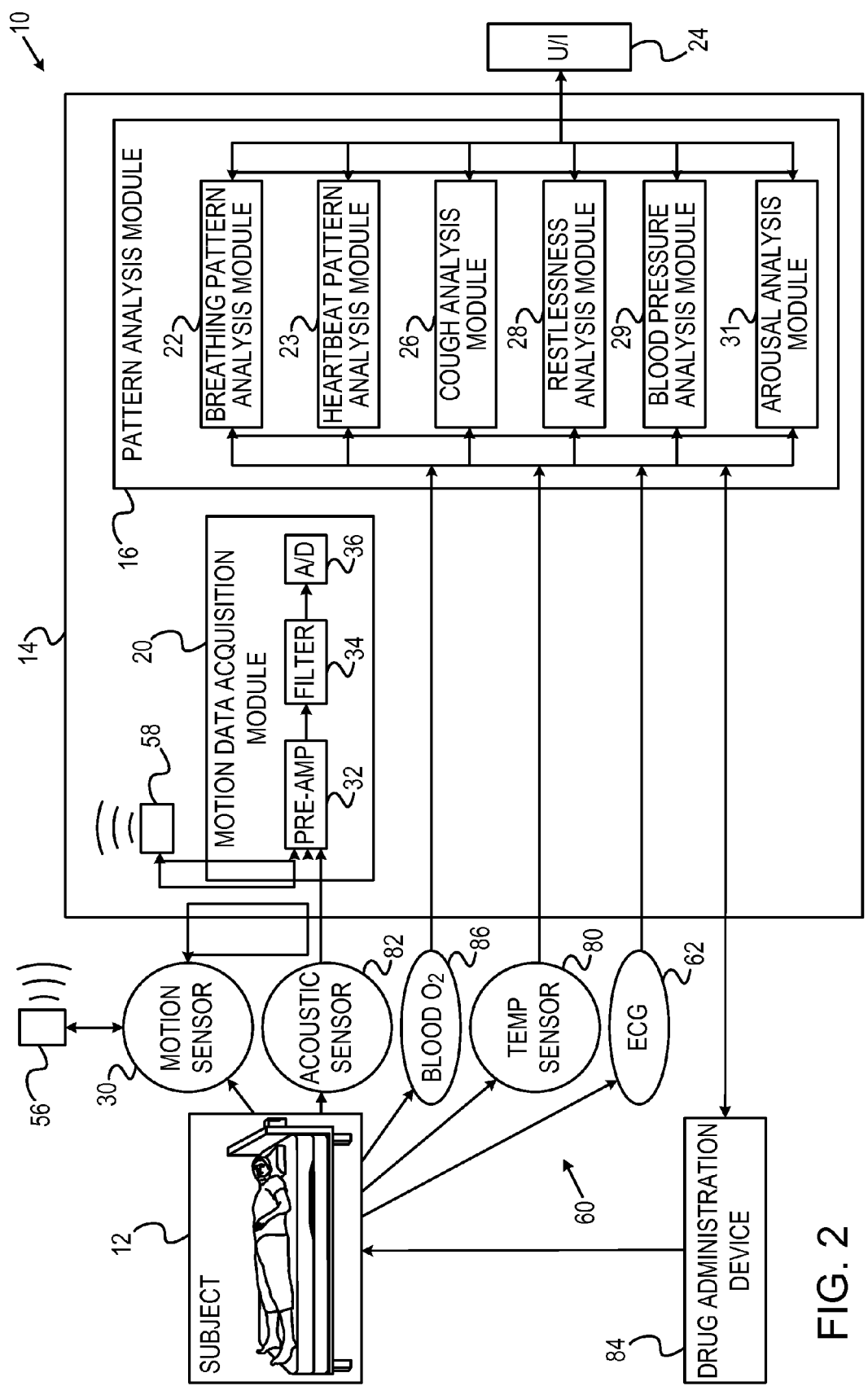
FIG. 2 is a schematic block diagram illustrating components of a control unit of the system of FIG. 1, in accordance with an embodiment of the present invention.

FIG. 2 is a schematic block diagram illustrating components of control unit 14 in accordance with an embodiment of the present invention. Control unit 14 typically comprises a motion data acquisition module 20 and a pattern analysis module 16. Pattern analysis module 16 typically comprises one or more of the following modules: a breathing pattern analysis module 22, a heartbeat pattern analysis module 23, a cough analysis module 26, a restlessness analysis module 28, a blood pressure analysis module 29, and an arousal analysis module 31. For some applications, two or more of analysis modules 20, 22, 23, 26, 28, 29, and 31 are packaged in a single housing. For other applications, the modules are packaged separately (for example, so as to enable remote analysis, by one or more of the pattern analysis modules, of breathing signals acquired locally by data acquisition module 20).

User interface 24 typically comprises a dedicated display unit, such as an LCD or CRT monitor. Alternatively or additionally, the user interface 24 comprises a wireless or wired communication port for relaying the acquired raw data and/or processed data to a remote site for further analysis, interpretation, expert review, and/or clinical follow-up. For example, the data may be transferred over a telephone line, and/or over the Internet or another wide-area network, either wirelessly or via wires.

Breathing pattern analysis module 22 is configured to extract breathing patterns from the motion data, as described hereinbelow with reference to FIG. 3, and heartbeat pattern analysis module 23 is configured to extract heartbeat patterns from the motion data. Alternatively or additionally, system 10 comprises another type of sensor, such as an acoustic or air-flow sensor attached or directed at the subject's face, neck, chest, and/or back, or placed under the mattress.

In an embodiment of the present invention, system 10 comprises a temperature sensor 80 for measurement of body temperature. For some applications, temperature sensor 80 comprises an integrated infrared sensor for measurement of body temperature. Body temperature is a vital sign indicative of general status of systemic infection and inflammation. Global rise in body temperature is used as a first screening tool in medical diagnostics.

Figure 3:
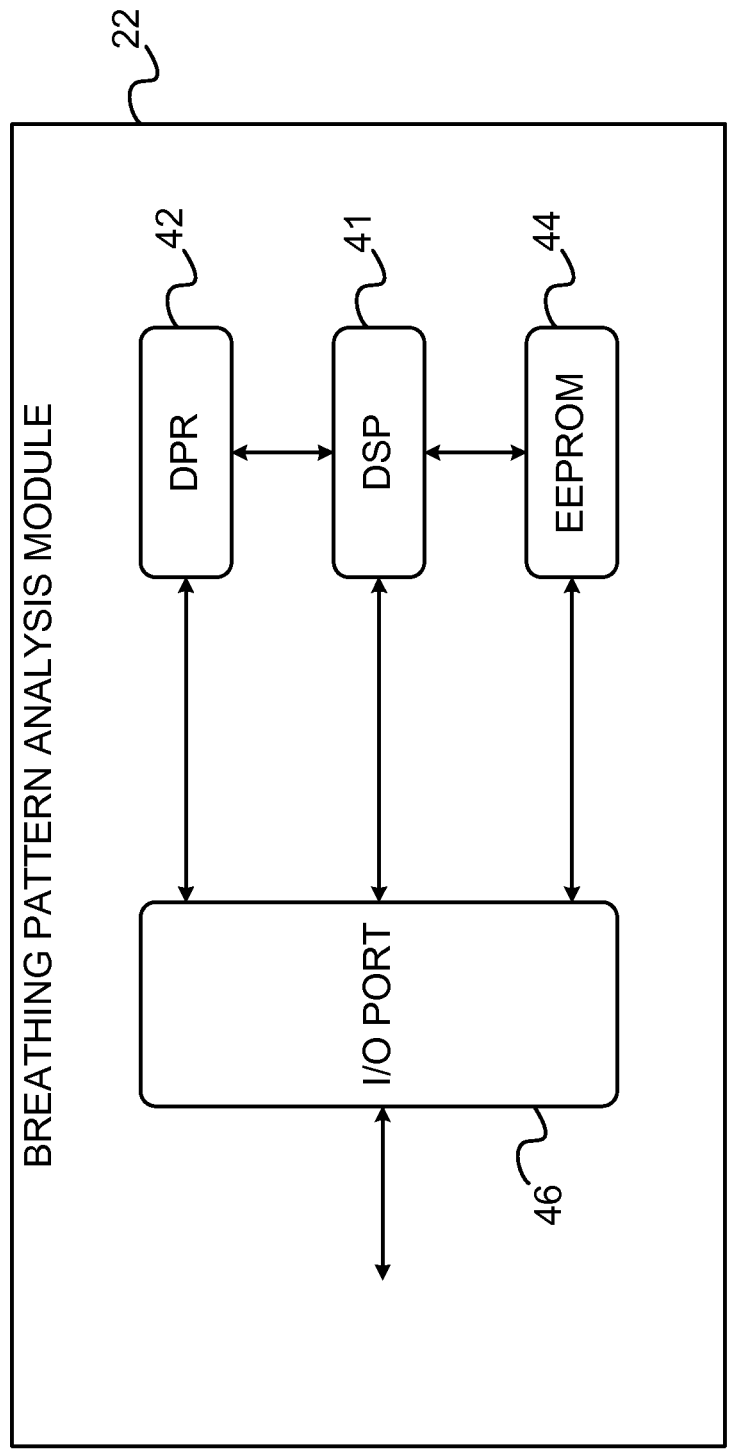
FIG. 3 is a schematic block diagram illustrating a breathing pattern analysis module of the control unit of FIG. 2, in accordance with an embodiment of the present invention.

FIG. 3 is a schematic block diagram illustrating components of breathing pattern analysis module 22, in accordance with an embodiment of the present invention. Breathing pattern analysis module 22 analyzes changes in breathing patterns, typically during sleep. Breathing pattern analysis module 22 typically comprises a digital signal processor (DSP) 41, a dual port RAM (DPR) 42, an EEPROM 44, and an I/O port 46. Modules 23, 26, 28, 29, and 31 may be similar to module 22 shown in FIG. 3. For example, modules 23, 26, 28, 29, and 31 may include a digital signal processor, a dual port RAM, an EEPROM, and an I/O port similar to digital signal processor 41, dual port RAM 42, EEPROM 44, and I/O port 46.

Reference is made to FIGS. 4A, 4B, and 4C, which are graphs illustrating the analysis of motion signals measured in accordance with an embodiment of the present invention. FIG. 4A shows a raw mechanical signal 50 as measured by the piezoelectric sensor under a mattress, including the combined contributions of breathing- and heartbeat-related signals and general body motion not related to breathing or heartbeat. Signal 50 was decomposed into a breathing-related component 52, shown in FIG. 4B, and a heartbeat-related component 54, shown in FIG. 4C, using techniques described hereinbelow.

In an embodiment of the present invention, data acquisition module 20 is configured to non-invasively monitor breathing and heartbeat patterns of subject 12. Breathing pattern analysis module 22 and heartbeat pattern analysis module 23 are configured to extract breathing patterns and heartbeat patterns respectively from the raw data generated by data acquisition module 20, and to perform processing and classification of the breathing patterns and the heartbeat patterns, respectively. Breathing pattern analysis module 22 and heartbeat pattern analysis module 23 are configured to analyze the respective patterns in order to (a) predict an approaching clinical episode, such as an asthma attack, heart condition-related lung fluid buildup, sepsis, cardiac arrest, or respiratory depression, and/or (b) monitor the severity and progression of a clinical episode as it occurs. User interface 24 is configured to notify subject 12 and/or a healthcare worker of the predicted or occurring episode. Prediction of an approaching clinical episode facilitates early preventive treatment, which generally improves outcomes, e.g., by lowering required dosages of medication, and/or lowering mortality and morbidity. When treating a hospitalized patient in a general care ward, for example, an earlier identification of patient deterioration may prevent the need to admit the patient to the ICU, shorten his length of stay, and increase the likelihood for successful recovery to discharge.

Normal breathing patterns in sleep are likely to be subject to slow changes over days, weeks, months and years. Some changes are periodic due to periodic environmental changes, such as a change in seasons, or to a periodic schedule such as a weekly schedule (for example outdoor play every Saturday), or biological cycles such as the menstrual cycle. Other changes are monotonically progressive, for example, changes that occur as children grow or adults age. In some embodiments of the present invention, system 10 tracks these slow changes dynamically.

In an embodiment of the present invention, two thin piezoelectric sensors are attached one on top of the other onto the semi-rigid plate. Both sensors experience practically the same deformation and therefore generate a highly correlated signal, effectively doubling the sensor capacitance and accordingly improving the signal to noise ratio without increasing the sensing surface area required.

In an embodiment of the present invention, system 10 is configured to monitor clinical parameters of the subject including, but not limited to, breathing rate; heart rate; coughing counts; expiration/inspiration ratios; amplitude, number, or frequency of augmented breaths; amplitude, number, or frequency of deep inspirations; amplitude, duration, or frequency of tremors, duration or frequency of sleep cycles, and amplitude, number, or frequency of restlessness patterns. These parameters are examples of "clinical parameters," as used in the specification and in the claims. In general, a clinical parameter is a numerical parameter that can be measured in a clinical setting and that has clinical value.

In an embodiment of the present invention, pattern analysis module 16 combines clinical parameter data generated from one or more of analysis modules 20, 22, 23, 26, 28, 29, and 31, and analyzes the data in order to predict and/or monitor a clinical event. For some applications, pattern analysis module 16 derives a score for each parameter based on the parameter's deviation from baseline values (either for the specific patient or based on population averages). Pattern analysis module 16 optionally combines the scores, such as by computing an average, maximum, standard deviation, or other function of the scores. The combined score is compared to one or more threshold values (which may or may not be predetermined) to determine whether an episode is predicted, currently occurring, or neither predicted nor occurring, and/or to monitor the severity and progression of an occurring episode. For some applications, pattern analysis module 16 learns the criteria and/or functions for combining the individual parameter scores for the specific patient or patient group based on personal or group history. For example, pattern analysis module 16 may perform such learning by analyzing parameters measured prior to previous clinical events.

For some applications, pattern analysis module 16 is configured to analyze the respective patterns, for example, the patterns of slow changes mentioned above, in order to identify a change in baseline characteristic of the clinical parameters. For example, in order to identify the slow change in average respiration rate in sleep for a child caused by growth, the system calculates a monthly average of the respiration rate during sleep. System 10 then calculates the rate of change in average respiration rate from one month to the next month, and displays this rate of change to the subject, subject's parent, or healthcare professional. Alternatively or additionally, system 10 identifies that the average respiration rate in sleep during weekends is higher than on weekdays, and thus uses a different baseline on weekends for comparing and making a decision whether a clinical episodes is present or approaching.

In an embodiment of the present invention, system 10 monitors and logs the clinical condition of a subject over an extended period of time, such as over at least two months. During this period of time, the system also monitors and logs behavioral patterns, treatment practices and external parameters that may affect the subject's condition. System 10 calculates a score for the clinical condition of the subject based on the measured clinical parameters. The system outputs this score for use by the subject or a caregiver.

Although system 10 may monitor breathing and heartbeat patterns at any time, for some conditions it is generally most effective to monitor such patterns during sleep at night. When the subject is awake, physical and mental activities unrelated to the monitored condition often affect breathing and heartbeat patterns. Such unrelated activities generally have less influence during most nighttime sleep. For some applications, system 10 monitors and records patterns throughout all or a large portion of a night. The resulting data set generally encompasses typical long-term respiratory and heartbeat patterns, and facilitates comprehensive analysis. Additionally, such a large data set enables rejection of segments contaminated with movement or other artifacts, while retaining sufficient data for a statistically significant analysis.

Reference is again made to FIG. 2. Data acquisition module 20 typically comprises circuitry for processing the raw motion signal generated by motion sensor 30, such as at least one pre-amplifier 32, at least one filter 34, and an analog-todigital (A/D) converter 36. Filter 34 typically comprises a band-pass filter or a low-pass filter, serving as an anti-aliasing filter with a cut-off frequency of less than one half of the sampling rate. The low-passed data is typically digitized at a sampling rate of at least 10 Hz and stored in memory. For example, the anti-aliasing filter cut-off may be set to 10 Hz and the sampling rate set to 40 Hz. For some applications, filter 34 comprises a band-pass filter having a low cutoff frequency between about 0.03 Hz and about 0.2 Hz, e.g., about 0.05 Hz, and a high cutoff frequency between about 1 Hz and about 10 Hz, e.g., about 5 Hz. Data acquisition module 20 typically digitizes the motion data at a sampling rate of at least 10 Hz, although lower frequencies are suitable for some applications.

Alternatively or additionally, the output of motion sensor 30 is channeled through several signal-conditioning channels, each with its own gain and filtering settings tuned according to the desired signal. For example, for breathing signals, a relatively low gain and a frequency passband of up to about 5 Hz may be used, while for heartbeat signals, a moderate gain and a slightly higher frequency cutoff of about 10 Hz may be used. For some applications, motion sensor 30 is additionally used for registration of acoustic signals, for which a frequency passband of about 100 Hz to about 8 kHz is useful.

In an embodiment of the present invention, system 10 is configured to monitor multiple clinical parameters of subject 12, such as respiration rate, heart rate, cough occurrence, body movement, deep inspirations, and/or expiration/inspiration ratio. Pattern analysis module 16 is configured to analyze the respective patterns in order to identify a change in the baseline pattern of the clinical parameters. In some cases, this change in the baseline pattern, which creates a new baseline substantially different from the previous baseline, is caused by a change in medication or other long-term change in the subject's condition, and provides the caregiver or healthcare professional with valuable feedback on the efficacy of treatment.

In an embodiment of the present invention, system 10 is configured to monitor clinical parameters, as defined hereinabove. Pattern analysis module 16 is configured to analyze the respective patterns in order to identify changes caused by medication and to provide feedback useful for optimizing the dosage of medication. For example, the medication may comprise a beta-blocker, which is used to treat high blood pressure (hypertension), congestive heart failure (CHF), abnormal heart rhythms (arrhythmias), and chest pain (angina), and sometimes to prevent recurrence of myocardial infarction (MI) in patients who have suffered a first MI. By measuring the heart rate patterns during sleep on a nightly basis, for example, the system may identify the effect of the medication, which may assist in adjusting the dosage until the optimal heart rate pattern is achieved. The system either reports the data to the patient or to the healthcare professional for use in adjusting the dosage, or transmits the data to an automatic drug dispensing device, which adapts the dosage accordingly.

Reference is again made to FIG. 1. In an embodiment of the present invention, motion sensor 30 comprises a pressure/vibration sensor (for example, a piezoelectric sensor) or an accelerometer, which is typically configured to be installed in, on, or under surface 37 upon which the subject lies, e.g., sleeps, and to sense breathing- and heartbeat-related motion of the subject. Typically, surface 37 comprises a mattress, a mattress covering, a sheet, a mattress pad, and/or a mattress cover. For some applications, motion sensor 30 is integrated into surface 37, e.g., into a mattress, and the motion sensor and reclining surface are provided together as an integrated unit. For some applications, motion sensor 30 is configured to be installed in, on, or under surface 37 in a vicinity of an abdomen 38 or chest 39 of subject 12. Alternatively or additionally, motion sensor 30 is installed in, on, or under surface 37 in a vicinity of a portion of subject 12 anatomically below a waist of the subject, such as in a vicinity of legs 40 of the subject. For some applications, such positioning provides a clearer pulse signal than positioning the sensor in a vicinity of abdomen 38 or chest 39 of the subject.

Reference is again made to FIG. 2. In an embodiment of the present invention, motion sensor 30 communicates wirelessly with control unit 14. In this embodiment, motion sensor 30 comprises or is coupled to a sensor wireless communication module 56, which wirelessly transmits and/or receives data to/from a control unit wireless communication module 58 that is coupled to control unit 14. The communications modules communicate using a signal that is analog (e.g., using standard AM or FM), or digital (e.g., using the Bluetooth® protocol). For example, in a hospital setting, a subject site such as a bed is typically occupied by each subject for only a few days. In some cases, it may be useful to replace sensor 30 whenever a new subject is assigned to the bed. In some cases, time spent by a nurse can be reduced by placing under a mattress a pad comprising sensor 30 and wireless communication module 56. The use of such a wirelessly-enabled sensor pad eliminates the need to connect and disconnect cables from control unit 14. Such use also makes the nurse's, physician's and subject's approach and/or entry into the bed more convenient. In embodiments in which sensor 30 operates wirelessly, the sensor, or a sensor assembly that comprises the sensor and the wireless communication module, typically comprises an internal power source, such as a battery. In order to preserve battery life, sensor 30 typically initiates communication upon detection of a relevant motion signal or other input.

In some settings, for example in hospitals, a plurality of systems 10 may be used in relatively close proximity. In such scenarios, each control unit 14 typically communicates only with the correct motion sensor 30 and not erroneously with another motion sensor 30 positioned at a different bed and associated with a different system 10. Bluetooth protocols, for example, allow for such pairing processes. In an embodiment, the system performs such pairing without initiating a conventional Bluetooth-type pairing process on both the sensor side and the control unit side. In addition to wirelessly-enabled motion sensor 30, control unit 14 is coupled to one or more contact sensors 60 applied to subject 12, such as a blood oxygen monitor 86 (e.g., a pulse oximeter), an ECG monitor 62, or a temperature sensor 80. Control unit 14 extracts pulse information from contact sensors 60. In order to identify the paired motion sensor 30 among several such transmitting motion sensors 30 within wireless range of the control unit, the control unit calculates the pulse data from each wireless signal received from a motion sensor 30 and identifies a signal that has pulse data that correlates with information received from contact sensors 60. Upon identifying such a match, the control unit records identifying features of the wireless communication module 56 coupled to the identified motion sensor 30 (e.g., a transmitter unique ID), such that from that point onward the identified sensor 30 is paired to control unit 14. For some applications, upon performing such pairing, control unit 14 notifies a healthcare worker that contact sensors 60 are no longer required and that the subject can be monitored with contactless sensor 30 only, or with fewer contact sensors 60.

For some wireless applications, upon activation of sensor 30, the nurse presses a connect button on control unit 14 and taps one or more times on sensor 30. Control unit 14 then connects to the one of a plurality of sensors 30 in the vicinity which transmits the taps at that exact point in time. Alternatively, user interface 24 provides a visual or audio indication of the taps, and the healthcare worker verifies that his or her taps are correctly displayed before approving the pairing of the sensor to the control unit. For some applications, the sensor, including the sensor plate, as described hereinbelow, does not comprise any buttons or other user controls. (These applications do not exclude the use of an on/off switch on wirelessly-enabled motion sensor 30.) For some applications, wirelessly-enabled motion sensor 30 is activated and paired with control unit 14 without requiring the pressing of any buttons or controls on the sensor. Instead the sensor is activated and paired either by tapping on the sensor or by temporarily connecting the sensor to the control unit with a wire. For some applications, a temporary cable is used to initiate the pairing of sensor 30 and control unit 14. After the sensor and control have been paired, the temporary cable is disconnected and the system operates using wireless communication. Alternatively or additionally, a motion sensor (e.g., a pressure sensor) coupled to control unit 14 by a wire is briefly placed on the reclining surface and pressed down against the mattress. The simultaneous readings from the wired motion sensor and from wirelessly-enabled motion sensor 30 enable control unit 14 to identify the particular wirelessly-enabled motion sensor 30 that is under the mattress that was pressed.

In an embodiment of the present invention, control unit 14 uses the pulse information provided by the contact sensor(s) to verify the accuracy of the respiration data monitored using motion sensor 30. Control unit 14 uses the information from sensor 30 to calculate respiration rate and heart rate and uses the information from the contact sensor to calculate heart rate. A correlation between the heart rate measured using the contact sensors and the heart rate measured using the sensor 30 indicates that the respiration calculated from sensor 30 is accurate as well.

In some implementations, it is useful to limit the time a sensor is used before being replaced (by way of illustration and not limitation, in order to prevent aging of the sensor which in some sensor production technologies may have a significant impact on the level of sensitivity of the sensor). Therefore, in an embodiment of the present invention, sensor 30 is configured to operate during a limited period of time. For some applications, sensor 30 comprises an internal timer configured to measure the amount of time the sensor is both in use and communicating with control unit 14. After a predetermined period of active use, sensor 30 is configured to no longer communicate with any control unit 14. For some applications, each sensor 30 has a unique ID. A global database of used and non-used sensors is maintained. Upon connection to a new sensor unit 30, control unit 14 checks in the global sensor database whether the sensor has been used elsewhere. This global database, in some embodiments, also maintains general calibration and other useful data for the operation of control unit 14.

In an embodiment of the present invention, sensor 30 comprises a single piezoelectric ceramic sensor. The sensor is attached to a plate, e.g., a semi-rigid plate comprising flexible plastic (e.g. Perspex (PMMA), polycarbonate, or acrylonitrile butadiene styrene (ABS)) or non-plastics (e.g., cardboard), for example having dimensions of 20 cm×28 cm×1.5 mm. The sensor is able to detect a signal when the subject assumes most common bed postures, even when the subject's body is not directly above the sensor. In one embodiment, sensor 30 is implemented using two or more thin piezoelectric sensors (e.g. radius of 13 mm and thickness of 100 um), wherein the two or more sensors are stacked on top of the semi-rigid plate so that the first sensor is attached to the plate and the second (and potentially third, etc.) is attached to the first sensor. The signals from both sensors are added to each other by amplification and/or digitizing electronics, in order to increase the signal to noise ratio of the system.

Figure 8:
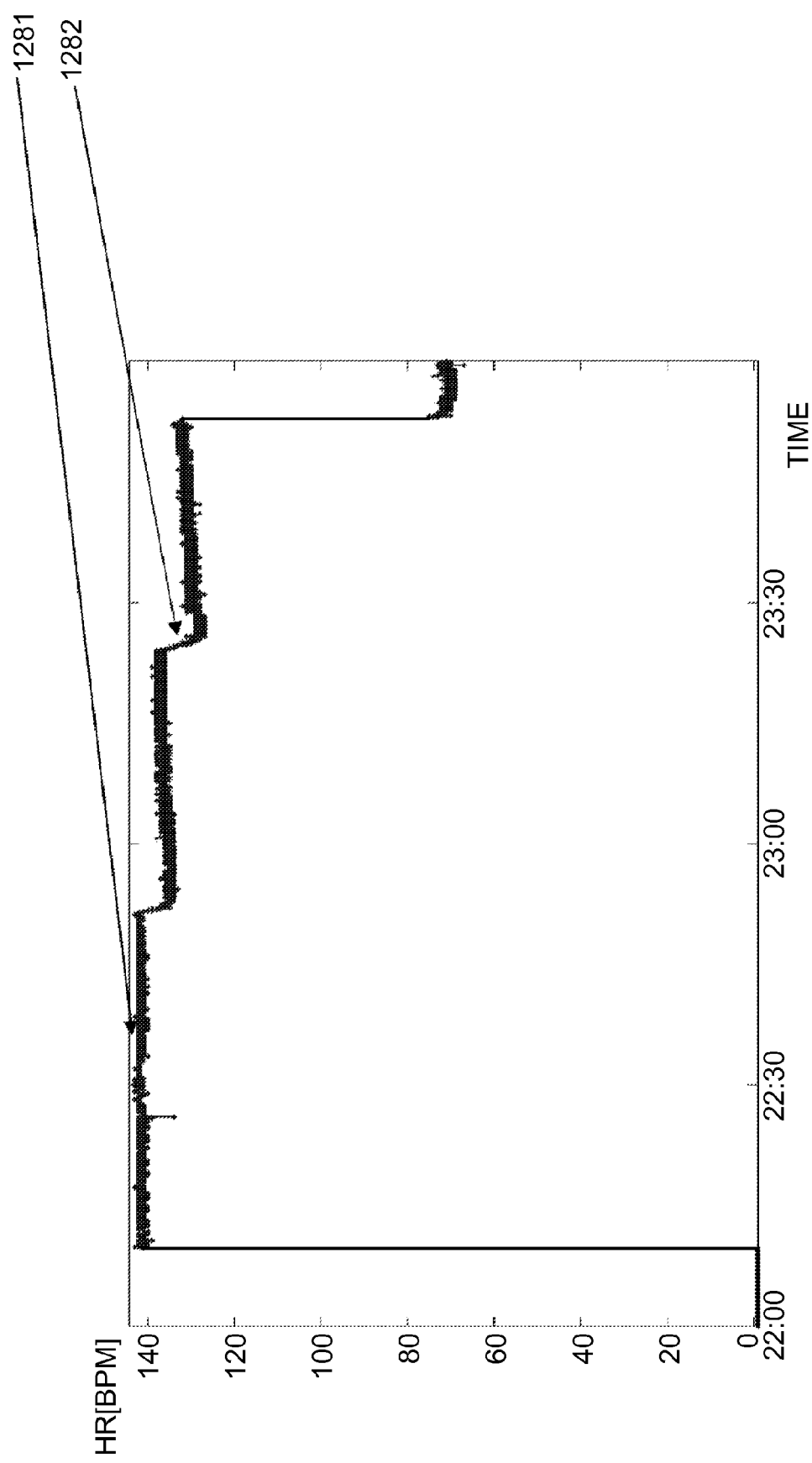
FIG. 8 is a schematic illustration of an exemplary heart rate signal output, measured in accordance with an embodiment of the present invention.

In an embodiment of the present invention, system 10 is configured to monitor heart rate continuously for subject 12. System 10 creates a heart rate reading every brief period of time, e.g. 1 second. System 10 also calculates the standard deviation of the HR reading every minute, e.g., the standard deviation of all of the heart rate readings in the past minute. In one embodiment, system 10 also continuously monitors the level of body motion of subject 12. For many subjects who are at rest, that standard deviation is in the range of 1 to 5 beats per minute (bpm). In some cases, subjects who are at rest display a sudden (an example of sudden is under 60 seconds, typically under 15 seconds) change in HR which is 5 to 10 times the above mentioned standard deviation, for example a standard deviation of 2 bpm and a drop in HR of 10 bpm within 30 seconds. In one embodiment, system 10 comprises an output unit which alerts clinicians of such events. In a clinical trial conducted using an embodiment of system 10, such alerts correlated highly with subjects' death within 72 hours of the alert and therefore such an alert has a significant potential benefit for clinicians. FIG. 8 shows a graph of the continuous heart rate output signal of a subject who was monitored with an embodiment of the present invention. In the area of 1281 of the graph, the subject's heart rate is highly stable with a standard deviation of under 2 bpm. In area 1282 of the graph, for example, a sudden change in heart rate is identified by system 10 during a time when the patient was identified by the system to be at rest. Therefore, there is significant clinical value in providing such an alert to a clinician in order to enable the appropriate intervention.

In one embodiment, system 10 has an option for the clinician to input information through user interface 24 regarding whether the subject is treated with beta blocker medication or other medication that may affect heart rate. Such drugs are generally expected to reduce the variability of the heart rate, and so system 10 increases the level of sensitivity to alerts upon changes in heart rate. For example if the baseline HR for a subject is 60 bpm and the standard alert criterion is a change of 33%, the criterion for a beta blocker patient may automatically be changed to 15%. Or for example, if the system is normally set up to drive the output unit to alert upon a change in HR vs. baseline that is higher than 20% in under 1 hour, then if the subject is using beta blocker medication which reduces HR variability, the system will alert upon a change of 5% in HR vs. baseline within an hour. In one embodiment, system 10 alerts on a change in HR vs. baseline for a beta blocker patient by combining the information about the HR and the motion information. For example, system 10 will alert upon a change of 10% in heart rate that is not correlated with a significant increase in the patient's overall body movements. In general, for patients who are treated by drugs that reduce heart rate variability, system 10 is configured to reduce by at least 30% the threshold amount of change for generating an alert upon detecting a change in heart rate, in response to receiving an indication that the patient is taking such a drug, compared to the threshold used for patients who are not taking such a drug.

For some applications, motion sensor 30 (for example, comprising a piezoelectric sensor) is encapsulated in a rigid compartment, which typically has a surface area of at least 10 $cm^2$, and a thickness of less than 5 mm. The sensor output is channeled to an electronic amplifier, such as a charge amplifier typically used with piezoelectric sensors, and capacitive transducers to condition the extremely high output impedance of the amplifier to a low impedance voltage suitable for transmission over long cables. The sensor and electronic amplifier translate the mechanical vibrations into electrical signals.

In an embodiment of the present invention, motion sensor 30 comprises a grid of multiple sensors, configured to be installed in, on, or under reclining surface 37. The use of such a grid, rather than a single unit, may improve breathing and heartbeat signal reception.

In an embodiment of the present invention, breathing pattern analysis module 22 extracts breathing-related signals by performing spectral filtering in the range of about 0.05 to about 0.8 Hz, and heartbeat pattern analysis module 23 extracts heartbeat-related signals by performing spectral filtering in the range of about 0.8 to about 5.0 Hz. For some applications, motion data acquisition module 20 adapts the spectral filtering based on the age of subject 12. For example, small children typically have higher breathing and heart rates, and therefore spectral filtering is typically set more tightly to the higher end of the frequency ranges, such as between about 0.1 and about 0.8 Hz for breathing, and between about 1.2 and about 5 Hz for heartbeat. For adults, spectral filtering is typically set more tightly to the lower end of the frequency ranges, such as between about 0.05 and about 0.5 Hz for breathing, and between about 0.5 and about 2.5 Hz for heartbeat.

In an embodiment of the present invention, pattern analysis module 16 derives a heartbeat signal from a breathing-related signal. This approach may be useful, for example, if the breathing-related signal is clearer than the directly monitored heartbeat signal. This sometimes occurs because the breathing-related signal is generated by more significant mechanical body movement than is the heartbeat-related signal.

In an embodiment of the present invention, the measured breathing-related signal is used to demodulate the heartbeat-related signal and thus enable improved detection of the heartbeat-related signal. Heartbeat pattern analysis module 23 demodulates the heartbeat-related signal using the breathing-related signal, such as by multiplying the heartbeat-related signal by the breathing-related signal. This demodulation creates a clearer demodulated signal of the heartbeat-related signal, thereby enabling its improved detection. In some cases, the power spectrum of the demodulated signal shows a clear peak corresponding to the demodulated heart rate. For some applications, the breathing-related signal used in the demodulation is filtered with a reduced top cut-off frequency (for example about 0.5 Hz, instead of the about 0.8 Hz mentioned above). Such a reduction generally ensures that only the basic sine wave shape of the breathing-related signal is used in the demodulation calculation.

In an embodiment of the present invention, for each of the filtered signals, a power spectrum is calculated and a largest peak is identified. A ratio of the heart rate-related peak to the respiration-related peak is calculated. The ratio is plotted for the duration of the night. This ratio is generally expected to remain constant for as long as the subject is lying in the same position. For each two consecutive time epochs (an epoch typically being between 30-300 seconds, for example 60 seconds), data acquisition module 20 calculates the percentage change of this ratio between the two epochs. The system determines that a change in body posture has occurred when the percentage change of the ratio is more than a threshold (typically between about 10% and about 50%, for example, about 25%). The frequency and timing of these changes is measured as an indication for restlessness in sleep.

In an embodiment, the change in the frequency distribution of the cardio-ballistic signal is used as an indication of a posture change.

In one embodiment, system 10 includes a posture change identification algorithm that identifies whether a patient has changed his position on a bed or other reclining surface or chair. The objective is to identify whether the patient moved between 1 of the 4 positions: supine, on stomach, on left side, or on right side, since such a change every 2-4 hours is generally required in order to prevent pressure ulcer formation in high risk patients. Alternatively, the system may identify a major body movement that includes a repositioning of the torso and/or the sacrum area that is most prone to pressure ulcer development. The system identifies events of large body motion and evaluates whether they involved a posture change of the main body.

Figure 9:
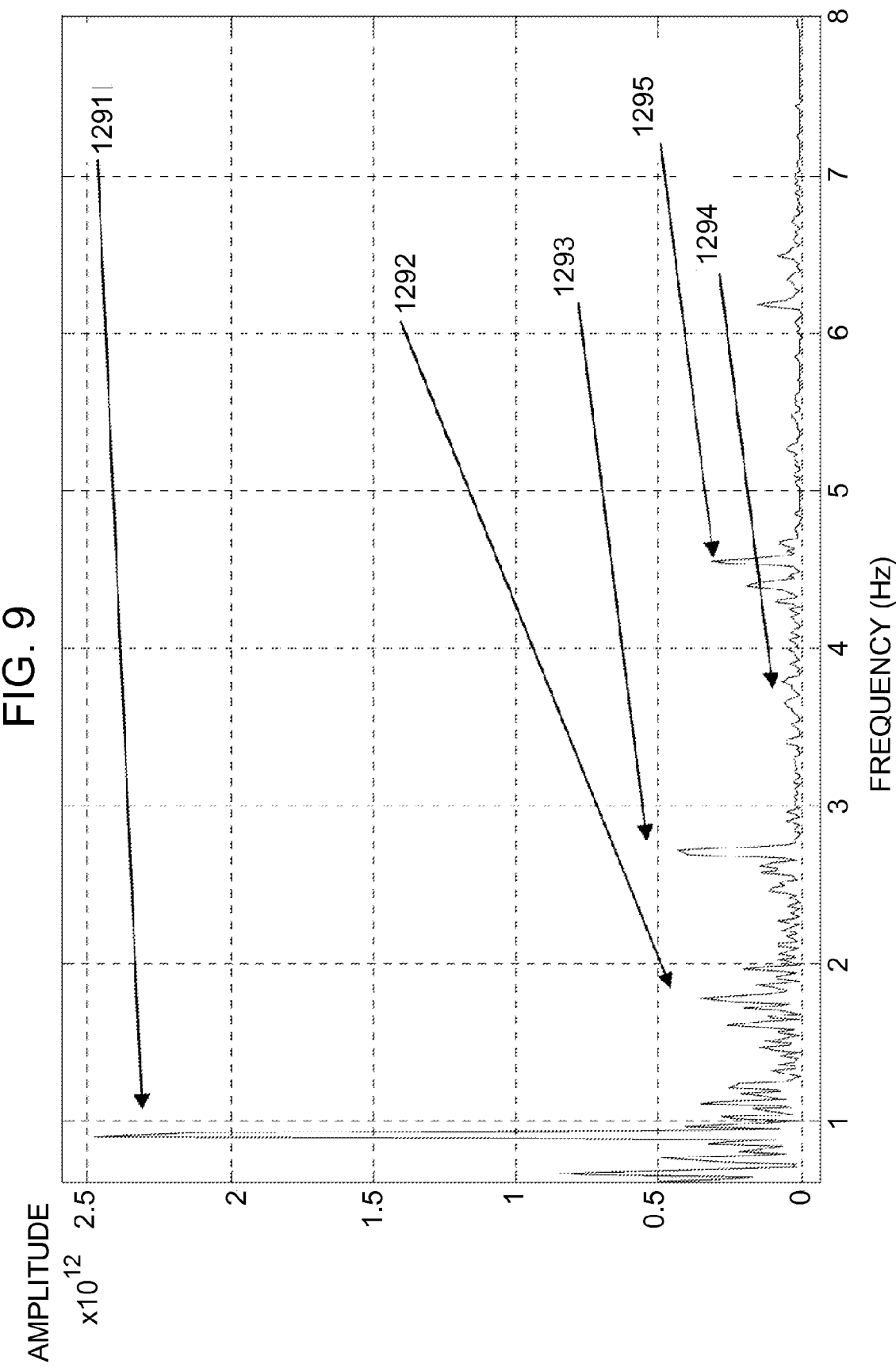
FIG. 9 is a schematic illustration of the frequency analysis of an exemplary heart rate related signal output, measured on a subject lying on his back, in accordance with an embodiment of the present invention.

The posture change identification has 3 phases:
1. Before the posture change
2. During the posture change
3. After the posture change Phase 1: Before the Posture Change During the time period before a posture change, when no large body motions are detected, signal features in the frequency domain and time domain that may change with posture are acquired. This serves as a baseline for then identifying the posture change event. The signal features in the frequency domain include in one embodiment at least one of the following:
- Amplitudes of frequencies generated by the heart beats, at the heart rate frequency and its harmonics. FIG. 9 shows such analysis as performed utilizing an embodiment of the present invention.
- Ratio between the amplitudes of the different harmonics.
- Amplitude of frequencies generated by the breathing related motion at the respiration rate frequency and its harmonics.
- Ratio between these harmonics.

The signal features in the time domain include in one embodiment at least one of the following:
- Patterns generated by the respiration.
- Patterns generated by the heart beats.
- Variability measures of the respiration cycle (e.g. standard deviation of the respiration motion signal amplitude, standard deviation of the respiration cycle times)
- Variability level of the heart beat pattern (e.g. standard deviation of the heart beat signal amplitude, standard deviation of the RR interval times)

Phase 2: During the Posture Change

All posture changes require a significant large body movement. Large body movements are defined and identified as described herein. During a posture change, large body movement events are classified into two categories:
1. Significant large body movement: Identified by a change in the raw signal's baseline (DC level) before vs. after the large body movement, which indicates a change in the patient's weight distribution on the mattress. Alternatively a large body movement is determined to be significant if the time over which the large body movement extends is over a threshold of, for example, 4-10 seconds, e.g., 6-10 seconds.
2. Non significant large body movement: a large body movement that does not meet the criteria above.

If the movement is classified as a significant large body movement, the third phase will determine if a posture change has occurred. Otherwise, the algorithm returns to Phase 1 above.

Phase 3: After the Posture Change

After the end of the large body movement is identified, the same features referred to in 'phase 1' are extracted from the signal portion after the movements, and compared to the features acquired before the large body movement. If a substantial difference is found, then a posture change event is identified. Otherwise a posture change is not recorded. For example, if the amplitude of the signal component corresponding to the base frequency of the heart rate is changed by more than a threshold that is between 30% and 80%, e.g., by more than 50%, a posture change is identified, or if the ratio between the amplitudes of the $1^{st}$ and $2^{nd}$ harmonics of the heart rate changes by more than 33%, a posture change is identified. In one embodiment, a score combining the differences of the different parameters listed above is calculated and compared to a threshold.

Figure 10:
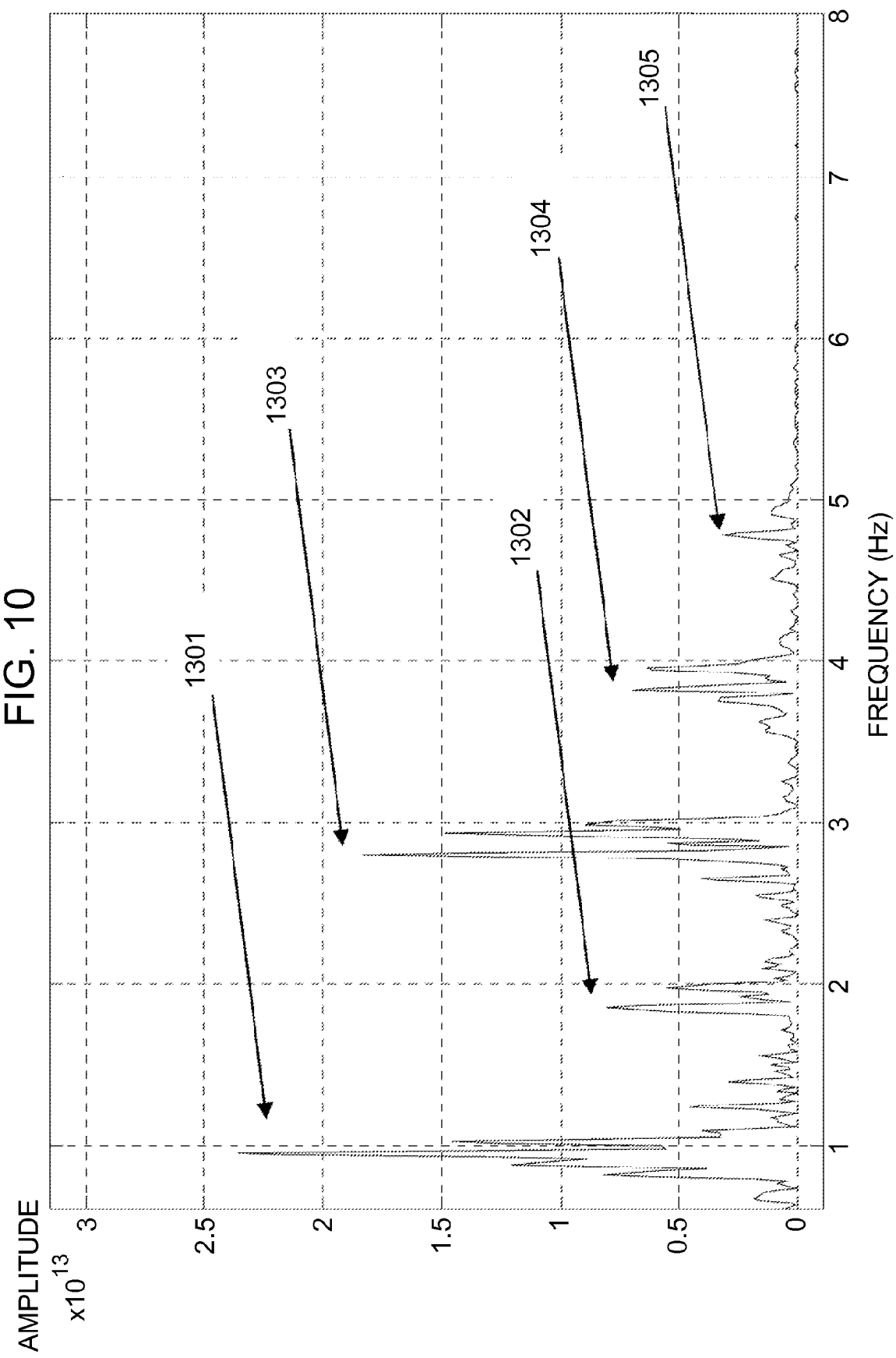
FIG. 10 is a schematic illustration of the frequency analysis of an exemplary heart rate related signal output, measured on the same subject as in FIG. 9, this time lying on his left side, in accordance with an embodiment of the present invention.

FIGS. 9 and 10 show the results of a clinical trial performed utilizing an embodiment of the present invention. Peaks 1291-1295 and 1301-1305 represent peaks in the frequency spectrum representing the different harmonics ($1^{st}$-$5^{th}$) of the heart rate in a spectrum analysis of the measured signal. The height and the ratio of the peaks are quite clearly different between a back (supine) lying position and a left side position. While lying on the left side (FIG. 10) the 3rd harmonic (1303) is much stronger than the 2nd (1302) harmonic; this does not apply for the supine position. A similar case also exists for the ratio between the 4th and 5th harmonic (1294, 1295 and 1304, 1305 respectively)—the 4th harmonic is almost non-existent in the supine position. Similar results were seen in several other clinical trials with various subjects on various beds. In an embodiment, a control unit identifies that a patient is lying on his side in response to determining that a clear change in the ratio of the harmonics of the heart rate in the power spectrum exists, when comparing the spectrum before and after a significant large body motion (e.g., a ratio relating the 2nd and 3rd harmonic, and/or a ratio relating the 4th and 5th harmonic).

This information of whether or not a posture change event was identified, is logged and displayed, and, if so set by the user, the output unit is driven to generate an alert if posture change is not identified for a set period of time (e.g. 2 hours). The logs are presented to the clinical management team in order to assist in maintaining compliance with pressure ulcer prevention protocols.

In one embodiment, phase 2 is identified through a user interface that enables the clinician to input when a posture change was made. The system then verifies that the posture change took place by comparing the readings after the clinician input, to those before, and documents the results accordingly. This provides the clinical team with a double layer of documentation of patient posture change, based both on clinician input and sensor signal analysis.

Piezo-electric sensors mounted on semi-rigid plates are often manufactured in a way that not all components provide a signal in the same direction when the same type of pressure is applied. That means that some sensors from a specific production batch will have a positive signal when additional pressure is applied from a specific direction and some will create a negative signal with the same type of pressure on a sensor with the same orientation. In one embodiment, system 10 utilizes a piezo-electric ceramic sensor mounted on a semi rigid plate that has been calibrated for directionality—i.e. for example that a downwards pressure on the plate's center always creates a positive signal. This is done for example, simply by testing the batch of mounted sensors and selecting only those sensors out of a production line that produce this preferred directionality of a signal.

In one embodiment, system 10 uses the following criteria to identify whether a posture change has taken place:
1. The size of the body motion signal (as compared to the respiratory related motion signal).
2. The change in baseline of the signal before and after the motion segment (phase 1 versus phase 3)
3. The direction of change of the signal during the motion segment (phase 2) compared to baseline (phase 1)
4. Change in heart rate during the motion period (phase 2 versus phase 1 and 3)

Figure 14:
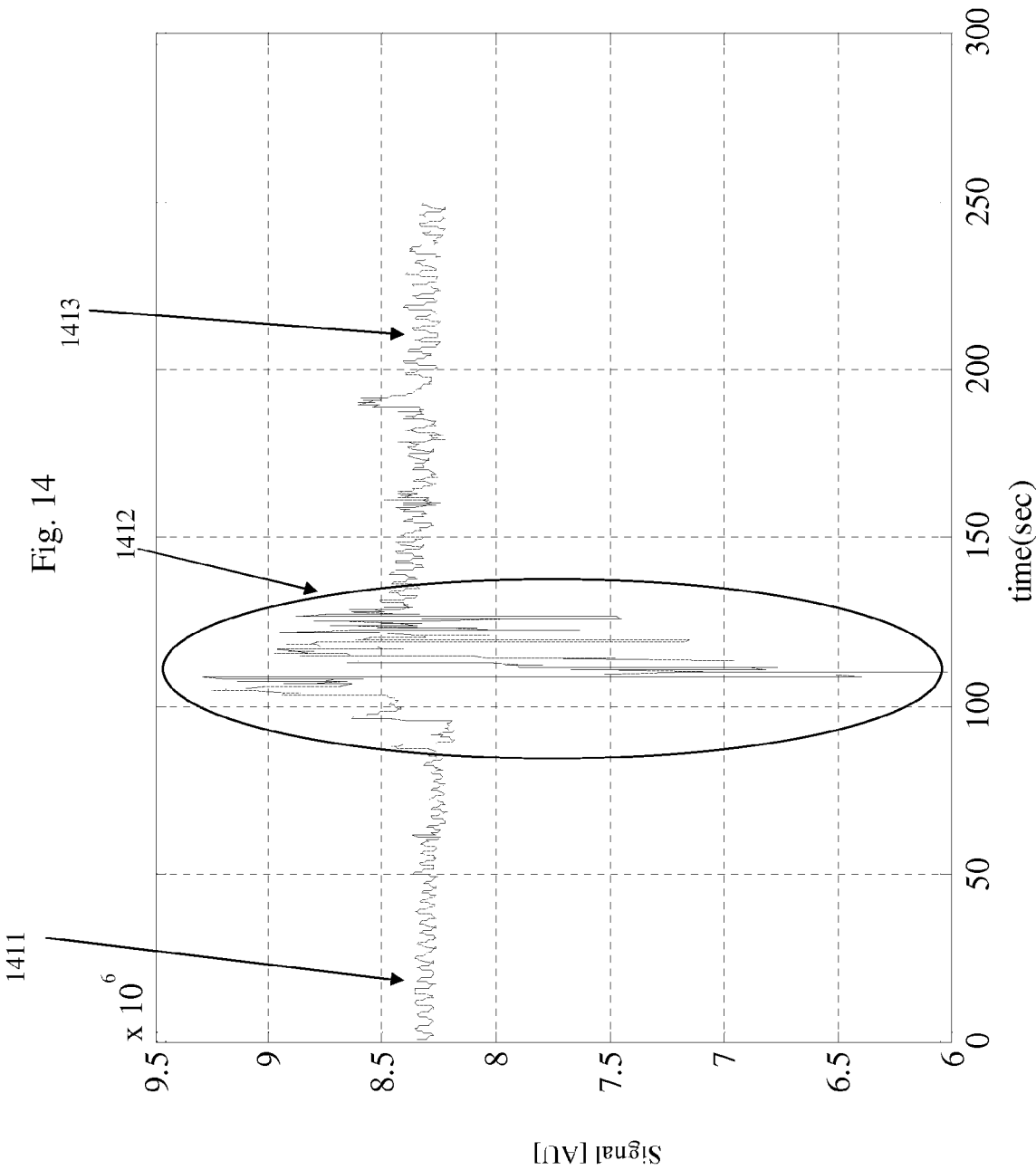
FIG. 14 is a schematic illustration of the motion signal, measured on a subject before during and after a posture change in the center of the bed, in accordance with an embodiment of the present invention.
Figure 15:
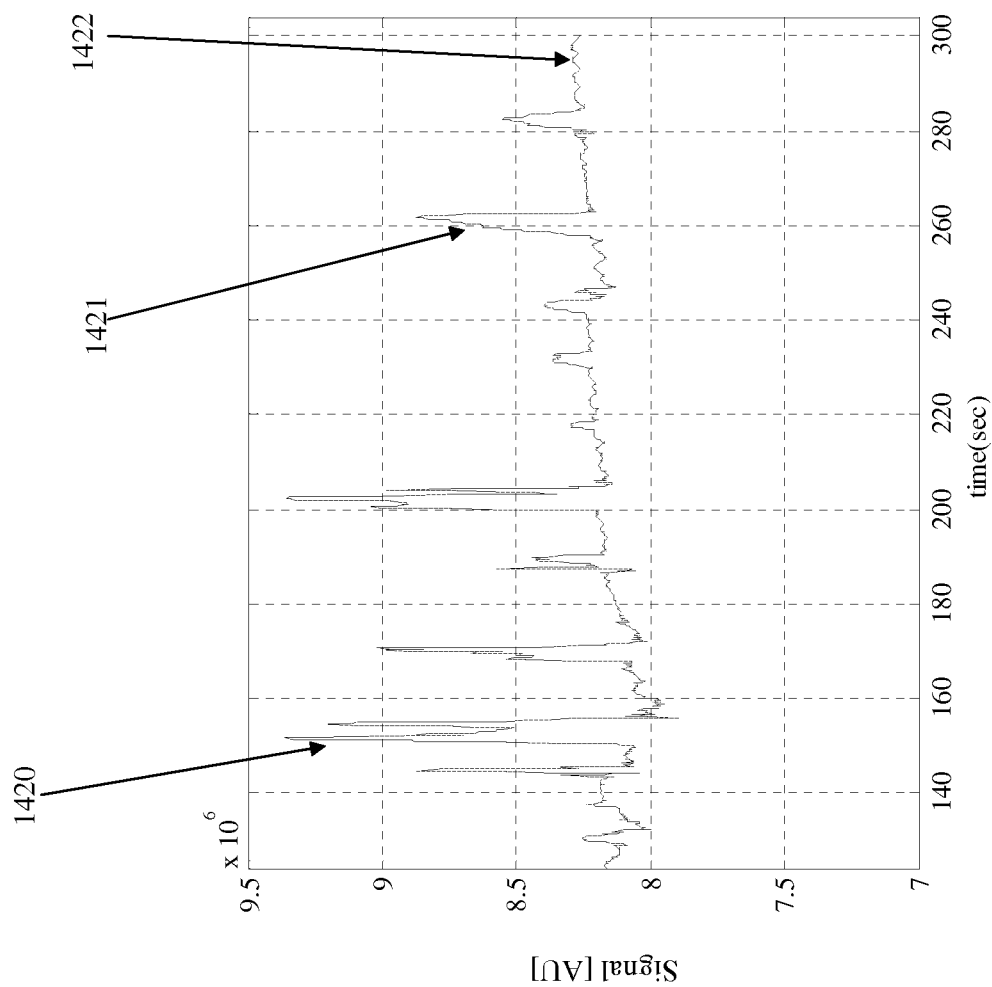
FIG. 15 is a schematic illustration of the motion signal, measured on a subject before and during several body movements that did not include any posture changes, in accordance with an embodiment of the present invention.

In one embodiment, system 10 looks for patterns that fit one of three potential scenarios, assuming the sensor is located in the center of the bed in terms of the width of the bed, and utilizing sensors calibrated for uniform directionality as described above:
1. Turning of patient while in the center of the bed
2. Turning of patient from side of the bed to the center of the bed
3. Turning of patient from the center to the side of the bed Turning of a patient while in the center is characterized by:

Bidirectional motion signal versus baseline. This is shown for example in FIG. 14. Section 1412 of FIG. 14 is the signal measured during a posture change, in which the patient was turned while in the center of the bed. Sections 1411 and 1413 represent baseline, before and after the posture change. FIG. 14 clearly shows that section 1412 of the motion signal moves both above and below sections 1411 and 1413, which represent the baseline. FIG. 15, by contrast, shows a signal collected during a clinical trial where the patient performed other body movements (e.g., moving hands and legs), without a posture change taking place. Unlike FIG. 14, it is seen in FIG. 15 that motion sections 1420 and 1421 show only a one directional (positive) change versus baseline section 1422. Several other such cases where collected and analyzed during clinical trials performed with an embodiment of the present invention.

A significantly larger motion signal than the respiratory motion signal as shown in FIG. 14 where the motion amplitude in section 1412 is much larger than the respiration related motion seen as the ripple in baseline in 1411 and 1413.

A transient increase in the heart rate of the patient during the time period of the motion, which then returns to normal after the motion ends—this is seen in some of the posture change events (data not shown).

In one embodiment, system 10 calculates a score for the probability that the identified motion event was a posture change and compares it to a threshold to determine whether the patient did perform a posture change. In another embodiment, system 10 requires that at least two of the above conditions take place in order to identify a posture change. In another embodiment, system 10 requires that all three of the above conditions take place in order to identify a posture change. There are disadvantages associated with frequent false positive indications of body movement as well as false negative indications of patient non-movement, which overburden the medical staff. In one embodiment, the clinician has the option to set the threshold level for identifying posture change, in response to, for example, patient condition and/or how busy the ward is at a given time.

Figure 16:
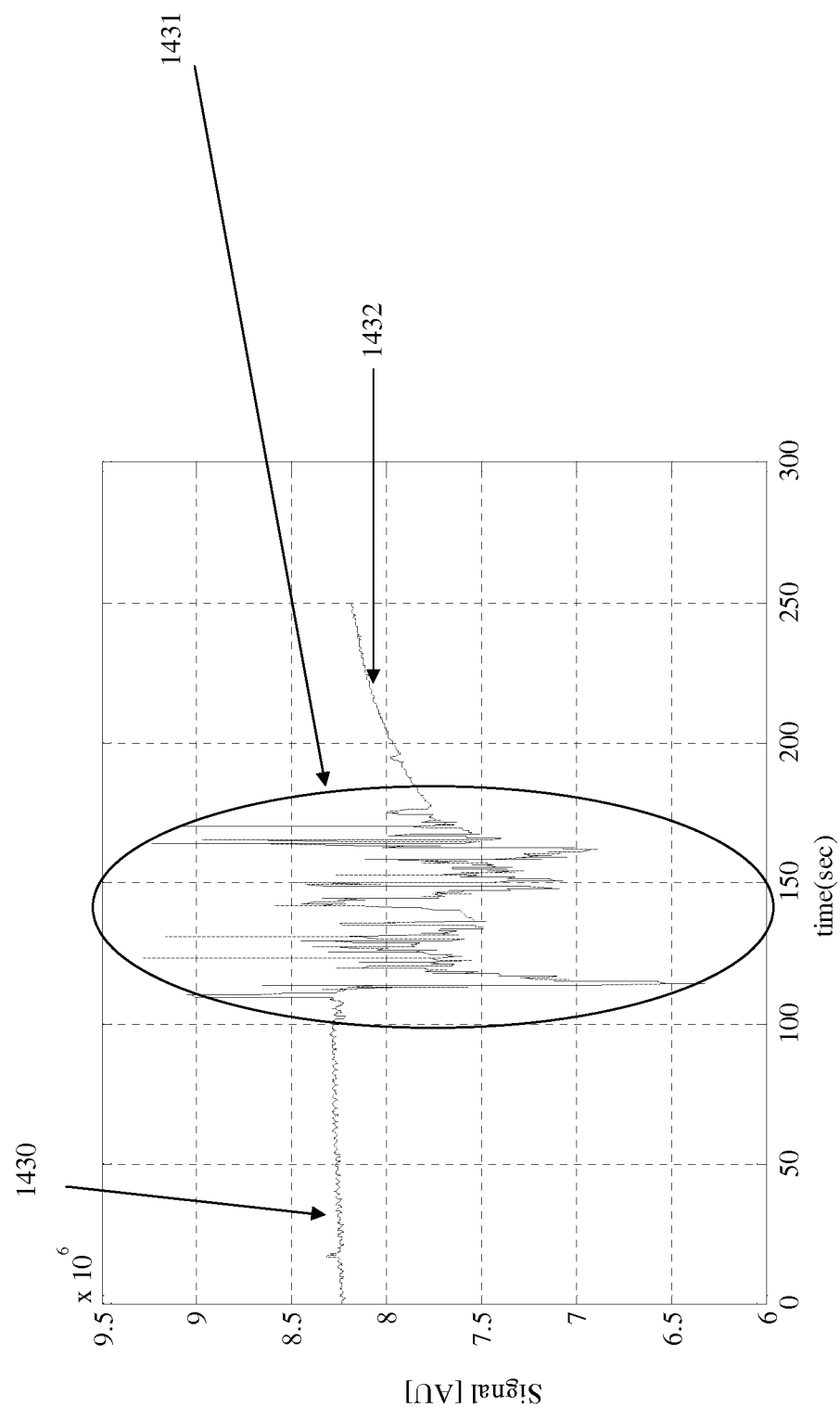
FIG. 16 is a schematic illustration of the motion signal, measured on a subject before during and after a posture change from the center of the bed to the side of the bed, in accordance with an embodiment of the present invention.

Turning of a patient from center to side is identified in one embodiment by:

Change in baseline that (assuming the sensor is in the center of the bed) represents a decreased pressure on the sensor. As shown for example in FIG. 16 where area 1431 shows the motion signal during the actual posture change and where baseline 1432 is lower than baseline 1430. In the specific embodiment used in the clinical trial whose result is shown in FIG. 16, the sensor is coupled to a high pass filter, which explains the slowly reducing change in baseline that will gradually return the baseline in section 1432 to be similar to that of 1430. But that temporary difference between the two baselines 1430 and 1432 is identified as being related to a change in the pressure put on the sensor by the patient before and after the posture change.

Change in heart rate that may take place

Motion signal level indicative of a large body motion and thus significantly higher than the respiration related motion.

The same scoring or decision making mechanism as described above is used in one embodiment for this type of posture change.

Turning of a patient from side to center is identified by:

Change in baseline that (assuming the sensor is in the center of the bed) represents increased pressure on the sensor.

Change in heart rate that may take place

Motion signal level significantly higher than the respiration related motion.

The same scoring or decision making mechanism as described above is used in one embodiment for this type of posture change.

In one embodiment, system 10 uses the above criteria to determine whether the subject changed posture from side to center, center to side, or center to center. The system logs that information and displays it to the clinician. This information helps the clinician and administrators to verify that pressure ulcer prevention protocols are maintained correctly. In one embodiment, system 10 logs which posture changes were performed by a clinician (as indicated through the operator interface) and which were performed by the subject on his own (no indication of clinician involvement through the interface). This again may help determine compliance with pressure ulcer prevention protocols. In one embodiment, system 10 allows the clinician to indicate through the operator interface whether the subject has been turned to the left, right, supine, or sitting position. This information is logged and displayed, and, in some embodiments, also verified through the system's sensor and signal analysis modules.

In one embodiment, system 10 uses the following criteria to distinguish noise, signal and noisy-signal:

1. Auto-correlation. In one embodiment, system 10 uses, but is not limited to, auto-correlation of a small portion of a signal (e.g., half a second, in the example below), and counts the number of local extrema in the result.
2. Power of signal in selected frequency bands e.g., noise signal outside the range of respiration or heart rates, but in the range of typical biological mechanical frequencies. In one embodiment, system 10 uses frequency bands around 3.73 Hz and 12.11 Hz, but additional or other bands can be used as well.
3. Ratio of the powers of the selected frequency bands.

In one embodiment, system 10 combines all three parameters to a noise score by using a system with two or more thresholds. Each measured parameter adds, subtracts or does not change the noise score according to its value relative to the thresholds. The thresholds and noise-score are set so that clearly negative values indicate definite signal, clearly positive values indicate noise, and scores around zero are typically a noisy-signal.

In one possible example, the noise level of each small portion (e.g., half of a second) increases by one point for each true statement in the list below:

PR<10,
PR<3,
PR<2,
P1<P1N,
P2<P2N,
AC>75.

and decreases by one point for each true statement in the list below:

PR>15,
PR>20,
PR>25,
P1>P1S,
P2>P2S,
AC<40.

Wherein:

P1 is the power in the first frequency band (e.g., 3.73 Hz)

P1N is the noise power in the first frequency band—where noise power is defined as the power measured in this frequency band when there is no one in bed P1S is the minimal signal power in the first frequency band—where minimal signal power is defined as the minimal signal power measured in this frequency band when the subject is at the maximal distance from the sensor that still allows measurement.

P2 is the power in the second frequency band (e.g., 12.11 Hz)

P2N is the noise power in the second frequency band

P2S is the minimal signal power in the second frequency

PR is the ratio between P1 and P2, i.e. PR=P1/P2

AC is the number of local extrema in the autocorrelation of the signal

The sum of noise level of two consecutive periods of half a second is considered the noise score (NS), which can have values from −12 to +12. Each half of a second is classified as:

Signal if NS<=0
Noise if NS>5
Noisy-signal if NS equals 1-5.

Figure 17:
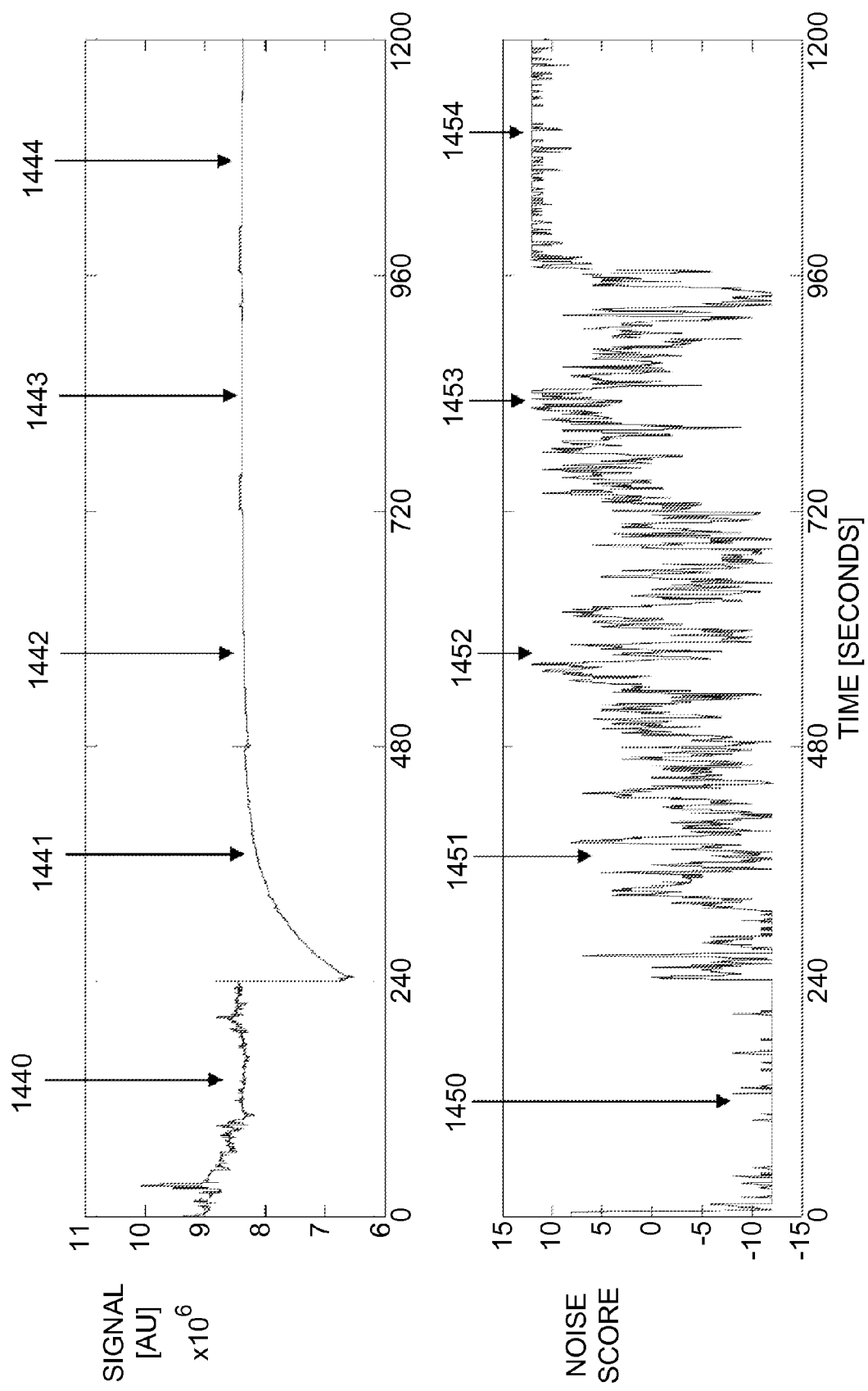
FIG. 17 is a schematic illustration of the motion signal, in accordance with an embodiment of the present invention, measured on a subject that lay in bed for 240 seconds, then sat upright for 240 seconds, then moved his legs out of bed for 240 seconds, then touched the floor with his legs while still sitting in bed for another 240 seconds, and then got out of bed for the last 240 seconds of the recording.

In one embodiment, system 10 uses the above described level of noise and power distribution to detect different relative states of patient and sensor, such as lying in bed, sitting in bed, and out of bed. The upper frame of FIG. 17 shows an example of a signal recorded while a subject lay in bed for 4 minutes (240 seconds)—section 1440, then sat upright for another 240 seconds—section 1441, then moved his legs out of bed for another 240 seconds—section 1442, then touched the floor with his legs for another 240 seconds (while still sitting in bed)—section 1443, and finally stood out of bed for the last 240 seconds of the record—section 1444. The lower frame of the same FIG. 17) shows one possible embodiment of the above-described noise score (NS) that changes from low stable negative values while lying in bed—section 1450, to mid-level fluctuating values around zero while sitting—sections 1451-1453, and high stable and positive values when subject is out of bed—section 1454.

In an embodiment, system 10 measures and analyzes the level of noise from the sensor and accordingly determines information about whether or not there is a subject in the bed and what is his position relative to the sensor. In some applications, it is useful to detect the subject's change of position from supine to sitting up with a single sensor. In some cases it is useful to determine that the subject's upper body is not in contact with the mattress, and to use this as a trigger for a caretaker or clinician to be alerted in order to assist the subject and prevent a potential fall. In one embodiment, system 10 detects bed exit if within 12 seconds after movement (or less), at least 3 periods of half a second are classified as noise. A subject is said to be lying in bed if after detection of movement at least 20 consecutive periods of half a second (10 seconds) were classified as signal. A subject is said to be sitting in bed if neither of the former conditions are met and if within 20 seconds, the majority of half a second periods are classified as noisy-signal, and for each period classified as signal there is at least one classified as noise.

In one embodiment, system 10 is utilized to reduce patient falls by driving the output unit to generate an alert when a subject sits up in bed, thus providing an early warning for the clinical team for a patient who may be leaving bed to enable assisting him before he actually leaves bed and thus prevent the falls effectively. For some applications, system 10 identifies that the patient has sat up in bed in response to ongoing calculation of the noise level in the motion signal, as described hereinabove.

In one embodiment, system 10 is connected to a smart bed system with an active surface such as the InTouch Critical Care Bed with an XPRT enabled active surface made by Stryker Medical of Kalamazoo, Mich. The bed is motorized and is able to provide, for example, the following interventions: change the backrest angle, rotate the patient, and/or provide vibration and percussion treatment. System 10 activates one of these interventions in response to the clinical parameters measured. For example, if an increase in the average respiratory rate over a period of 5 minutes to 3 hours (for example 30 minutes) is identified without a corresponding increase in the subject's activity level, which may indicate a deterioration of a patient's respiratory condition, the vibration and percussion treatment is activated or the backrest angle is increased to 30 degrees. Alternatively, if the subject's number of posture changes per time has been below a threshold for a period of time between 1 hour and 24 hours (for example 3 hours), the active surface rotates the patient. Without sensing the subject's rotation, the bed would have to turn the subject every 3 hours, even if he turned autonomously, thus potentially creating a significant and/or unnecessary discomfort to the subject.

In an embodiment of the present invention, system 10 identifies a trend of change in one or more of the measured clinical parameters as an indication of the onset or progression of a clinical episode. For example, successive increases in respiration rate over three consecutive nights may indicate to system 10 that an asthma exacerbation is likely.

In an embodiment of the present invention, system 10 calculates an asthma score based on measured clinical parameters. For some applications, the system uses the following equation to calculate the asthma score:

$$S(D) = \frac{20R_a(D) + 20R'(D) + 20R_b(D) + 10HR_a(D) + 10HR'(D) + AC(D) + 5SE(D) + 5DI(D)}{N} \quad \text{(Equation 1)}$$

wherein:

S(D)—asthma score for date D $R_a(D)$—average respiration rate for date D, divided by the average respiration rate for all previous measured dates.

R'(D)—first derivative of the respiration rate calculated as follows:

$$R'(D) = \frac{R(D) - R(D-1)}{R(D-1)} \quad \text{(Equation 2)}$$

wherein R(D) is the average respiration rate for date D and R(D−1) is the average respiration rate for the date immediately prior to date D.

$R_b(D)$—average respiration rate for the date immediately prior to date D, divided by the average respiration rate over the previous n dates, e.g., the previous three dates.

$HR_a(D)$—average heart rate for date D, divided by the average heart rate for all previous measured dates.

HR'(D)—first derivative of the average heart rate calculated as follows:

$$HR'(D) = \frac{HR(D) - HR(D-1)}{HR(D-1)} \quad \text{(Equation 3)}$$

wherein HR(D) is the average heart rate for date D and HR(D−1) is the average heart rate for the date immediately prior to date D.

AC(D)—a measure of activity level during sleep (restlessness) for date D, divided by the average of that measure for all previous measured dates.

SE(D)—sleep efficiency for date D, divided by the average sleep efficiency for all previous measured dates.

DI(D)—number of deep inspirations for that date D, divided by the average number of deep inspirations for all previous measured dates.

N—an integer dependent upon the condition under consideration, among other things, and typically having a value between about 80 and about 110, such as between about 88 to about 92, for example, about 91.

Each of the above-mentioned parameters is calculated for the duration of the sleep time or specific hours during the night prior to date D.

The values of $R_a(D)$, $HR_a(D)$, AC(D), SE(D), and DI(D) are typically calculated for at least three dates prior to date D, for example, for at least three successive dates immediately prior to date D. Alternatively, $R_a(D)$, $HR_a(D)$, AC(D), SE(D), and DI(D) are calculated as a ratio of the measurement of the current date to the average over K dates, wherein K is typically between about 7 and about 365, such as about 30. Alternatively, for some applications, the K dates are successive dates, for example, K successive dates immediately before date D. Alternatively, $R_a(D)$, $HR_a(D)$, AC(D), SE(D), and DI(D) are calculated as ratios of the measurement of the current date to the average over the previous K nights that have not included an exacerbation of the chronic condition, identified either manually by user input, or automatically by system 10. For some applications, the average heart rate for each minute of sleep is calculated, and the standard deviation of this time series is calculated. This standard deviation is added as an additional parameter to, for example, a score equation such as Equation 1 above.

In an embodiment of the present invention, system 10 calculates the asthma score based on the clinical parameters, as defined hereinabove. For some applications, the equation comprises a linear expression of the clinical parameters, for example: the breathing rate change in percent versus baseline and the rate of coughs per a specific length of time. For some applications, the equation is an expression dependent on the clinical parameters that is close to linear, i.e., when the score is graphed versus any of the clinical parameters, the area between the graph of the score and the closest linear approximation would be relatively small compared to the area under the linear approximation (e.g., the former area is less than 10% of the latter area). For some applications, the asthma score is calculated using the following equation:

$$S(D)=100-BR(D)-C(D) \quad \text{(Equation 4)}$$

wherein:
S(D)—asthma score for date D.
BR(D)—percent increase in average respiration rate during sleep for date D vs. the subject's baseline (e.g., if respiration rate BR for date D is 20% above baseline, then BR(D)=20).
C(D)—the number of cough events for date D (e.g., the number of coughs measured between 12:00 midnight and 6:00 AM or over another period), or the rate of cough events per unit time.

In an embodiment, the calculated asthma score is compared to a threshold (e.g., between about 50 and about 90, such as about 75). If the score is below the threshold, subject 12 or a healthcare worker is alerted that intervention is required.

In an embodiment of the present invention, system 10 calculates an asthma score based on the clinical parameters, as defined hereinabove. For some applications, the asthma score is calculated using the following equation:

$$S(D)=100-k1*BR(D)-k2*C(D) \quad \text{(Equation 5)}$$

wherein:
S(D)—asthma score for date D.
BR(D)—percent increase in average respiration rate during sleep for date D vs. the subject's baseline (e.g., if respiration rate BR for date D is 20% above baseline, then BR(D)=20).
C(D)—the number of cough events for date D (e.g. the number of coughs measured between 12:00 midnight and 6:00 AM or over another period), or the rate of cough events per unit time.
k1, k2—coefficients for the respiration rate and cough parameters. Typically k1 and k2 are between about 0.7 and about 1.3.

In an embodiment, the calculated asthma score is compared to a threshold (e.g., between about 50 and about 90, such as about 75). If the score is below the threshold, the subject 12 or a healthcare worker is alerted that intervention is required.

In an embodiment of the present invention, system 10 calculates an asthma score based on the clinical parameters, as defined hereinabove. For some applications, the asthma score is calculated using the following equation:

$$S(D)=100-k1*BR(D)-k2*C(D)-k3*RS(D) \quad \text{(Equation 6)}$$

wherein:
S(D)—asthma score for date D.
BR(D)—percent increase in average respiration rate during sleep for date D vs. the subject's baseline (e.g., if respiration rate BR for date D is 20% above baseline, then BR(D)=20).
C(D)—the number of cough events for date D. In an embodiment, this is measured between 12:00 midnight and 6:00 am, or over another period, or C(D) is the rate of cough events per unit time.
RS(D)—The level of restlessness in sleep for date D (e.g., on a scale of 0-Y, where typically Y is between 10 and 30, for example, 17, where Y is the highest level of restlessness and 0 is the lowest level).
k1, k2, k3—coefficients for the respiration rate, cough, and restlessness parameters. Typically k1, k2, and k3 are between about 0.6 and about 1.5.

In an embodiment, the calculated score is compared to a threshold (typically between about 60 and about 80, such as about 74). If the score is below the threshold, subject 12 or a healthcare worker is alerted that intervention is required.

As mentioned above, motion of the subject during sleep includes regular breathing-related and heartbeat-related movements as well as other unrelated body movements. In general, breathing-related motion is the dominant contributor to body motion during sleep. In an embodiment of the present invention, pattern analysis module 16 is configured to substantially eliminate the portion of the motion signal received from motion data acquisition module 20 that represents motion unrelated to breathing and heartbeat. For some applications, pattern analysis module 16 removes segments of the signal contaminated by non-breathing-related and non-heartbeat-related motion. While breathing-related and heartbeat-related motion is periodic, other motion is generally random and unpredictable. For some applications, pattern analysis module 16 eliminates the non-breathing-related and non-heartbeat-related motion using frequency-domain spectral analysis or time-domain regression analysis. Techniques for applying these analysis techniques will be evident to those skilled in art who have read the present application. For some applications, pattern analysis module 16 uses statistical methods, such as linear prediction or outlier analysis, to remove non-breathing-related and non-heartbeat-related motion from the signal.

In an embodiment of the present invention, pattern analysis module 16 determines the onset of an attack, and/or the severity of an attack in progress, by comparing the measured breathing rate pattern to a baseline breathing rate pattern, and/or the measured heart rate pattern to a baseline heart rate pattern.

In an embodiment of the present invention, pattern analysis module 16 comprises cough analysis module 26, which is configured to detect and/or to assess coughing episodes associated with approaching or occurring clinical episodes. In asthma, mild coughing is often an important early pre-episode marker indicating impending onset of a clinical asthma episode (see, for example, the above-mentioned article by Chang AB). In congestive heart failure (CHF), coughing may provide an early warning of fluid retention in the lungs caused by worsening of the heart failure or developing cardiovascular insufficiency.

For some applications, coughing sounds are extracted from motion sensor 30 installed in, on, or under a reclining surface, or from a microphone installed in proximity of the subject, typically using acoustic band filtering of between about 50 Hz and about 8 kHz, e.g., between about 100 Hz and about 1 kHz. Alternatively, the signal is filtered into two or more frequency bands, and motion data acquisition module 20 uses at least one frequency band of typically very low frequencies in the range of up to about 10 Hz for registering body movements, and at least one other frequency band of a higher frequency range, such as between about 50 Hz and about 8 kHz, for registering acoustic sound. For some applications, the module uses a narrower acoustic band, such as between about 150 Hz and about 1 kHz.

In an embodiment of the present invention, breathing pattern analysis module 22 is configured to detect, typically during night sleep, an abnormal breathing pattern associated with CHF, such as tachypnea, Cheyne-Stokes Respiration (CSR), or periodic breathing.

Figure 6:
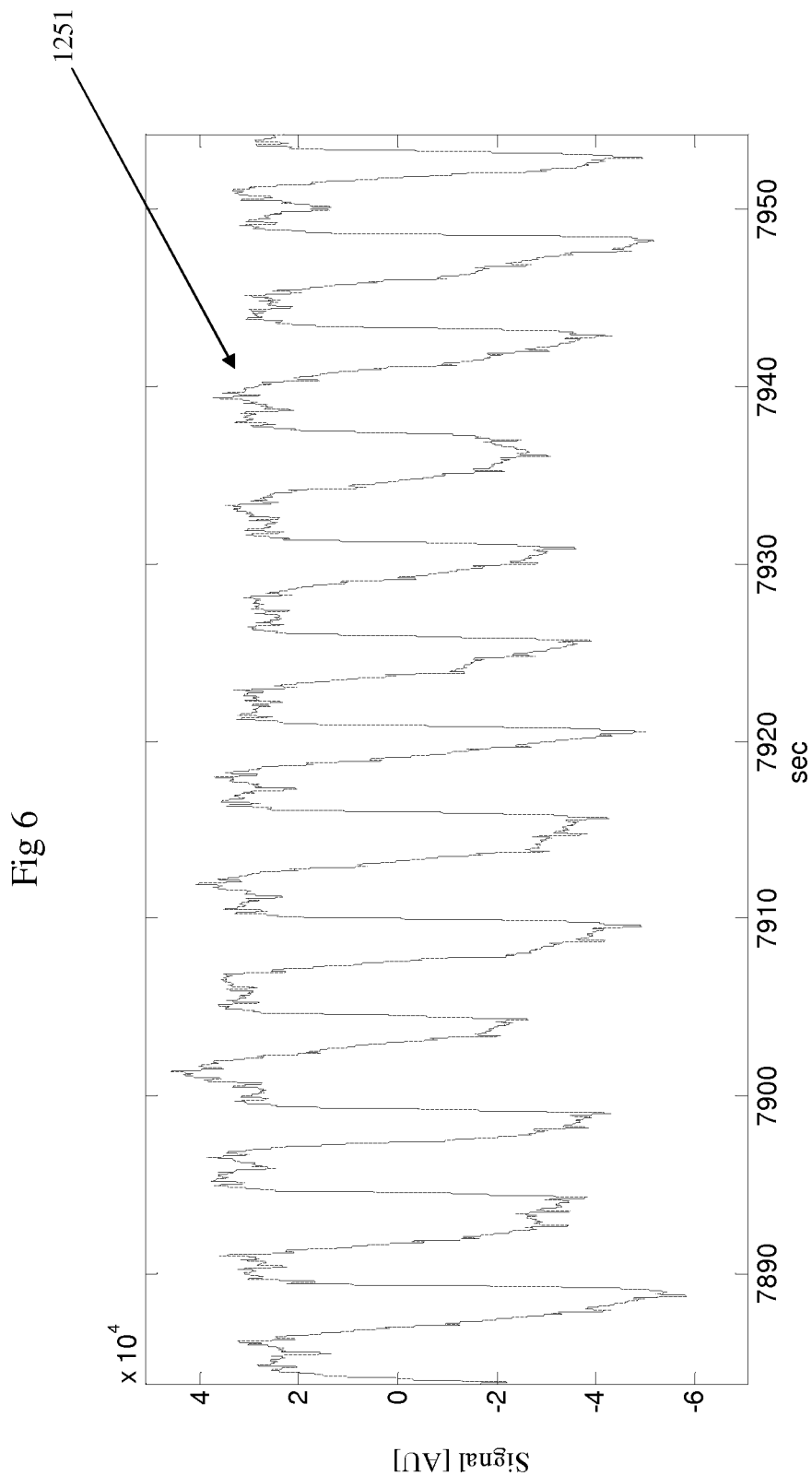
FIG. 6 is a schematic illustration of an exemplary mechanical signal, measured on a subject with a normal respiratory pattern, in accordance with an embodiment of the present invention measured on a subject with a normal respiratory pattern.
Figure 7:
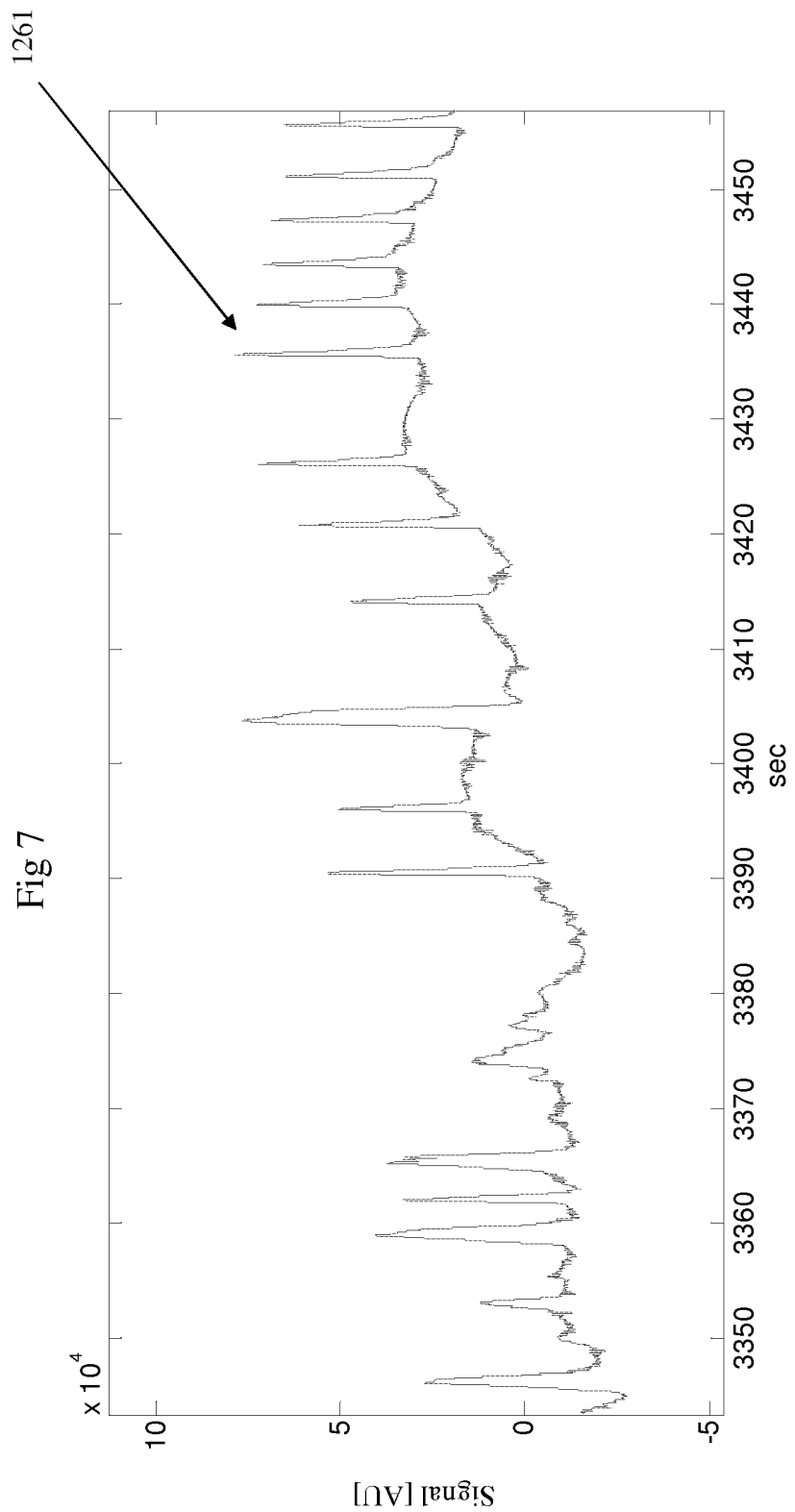
FIG. 7 is a schematic illustration of an exemplary mechanical signal, in accordance with an embodiment of the present invention measured on a subject with gasping breaths.

In an embodiment of the present invention, breathing pattern analysis module 22 is configured to detect abnormal breathing patterns that may indicate a deterioration in patient's condition, e.g. gasps, Agonal Breathing, Ataxic Breathing, Cheyne Stokes, or Biot's respiration. In one embodiment, system 10 identifies patterns that are related to the shape of the respiration motion, independently of any changes in overall rate of the respiratory motion. Monitoring of the shape of the respiration motion constitutes monitoring of non-rate respiratory patterns. Shape may include, for example, the time between characteristic portions of the respiration motion, or the slope of inhale or exhale. A gasp is identified as a sharp breathing motion which is contrasted from a normal breathing motion which is smoother. System 10, for example, identifies a much higher rate of change (slope) in the gasping motion signal than in the signal measured during normal breathing motion (see FIG. 7, line 1261 that shows a gasping breath motion signal versus FIG. 6, line 1251 that shows a normal breathing motion signal). For example, low respiratory rate (3-4 breaths) irregularity in the breathing rate with a sharp gasp like breathing pattern indicates ataxic breathing. Irregularity is analyzed, for example, by calculating the variability of the time between breaths. In one embodiment, the system activates an alert upon identification of one of these breathing patterns.

In clinical studies performed using an embodiment of the present invention, several subjects were identified by a clinician to be using auxiliary muscles (i.e., accessory muscles) in their breathing cycle, in accordance with some applications of the present invention. For example, the subjects were identified as possibly using internal intercostal muscles and/or abdominal muscles during expiration, and/or as using the pectoralis major muscle, scalene muscles, the trapezius muscle, and/or the sternocleidomastoid muscle during inspiration. In some cases, it was determined that such subjects underwent a breathing motion that included a double movement of the chest area during a substantial number of respiratory cycles. Thus, it is hypothesized by the inventors of the present application that an identification that a subject is undergoing a breathing motion that includes a double movement of the chest area during at least some respiratory cycles may be indicative of the fact that the subject is using accessory muscles during respiration of the subject.

Figure 11:
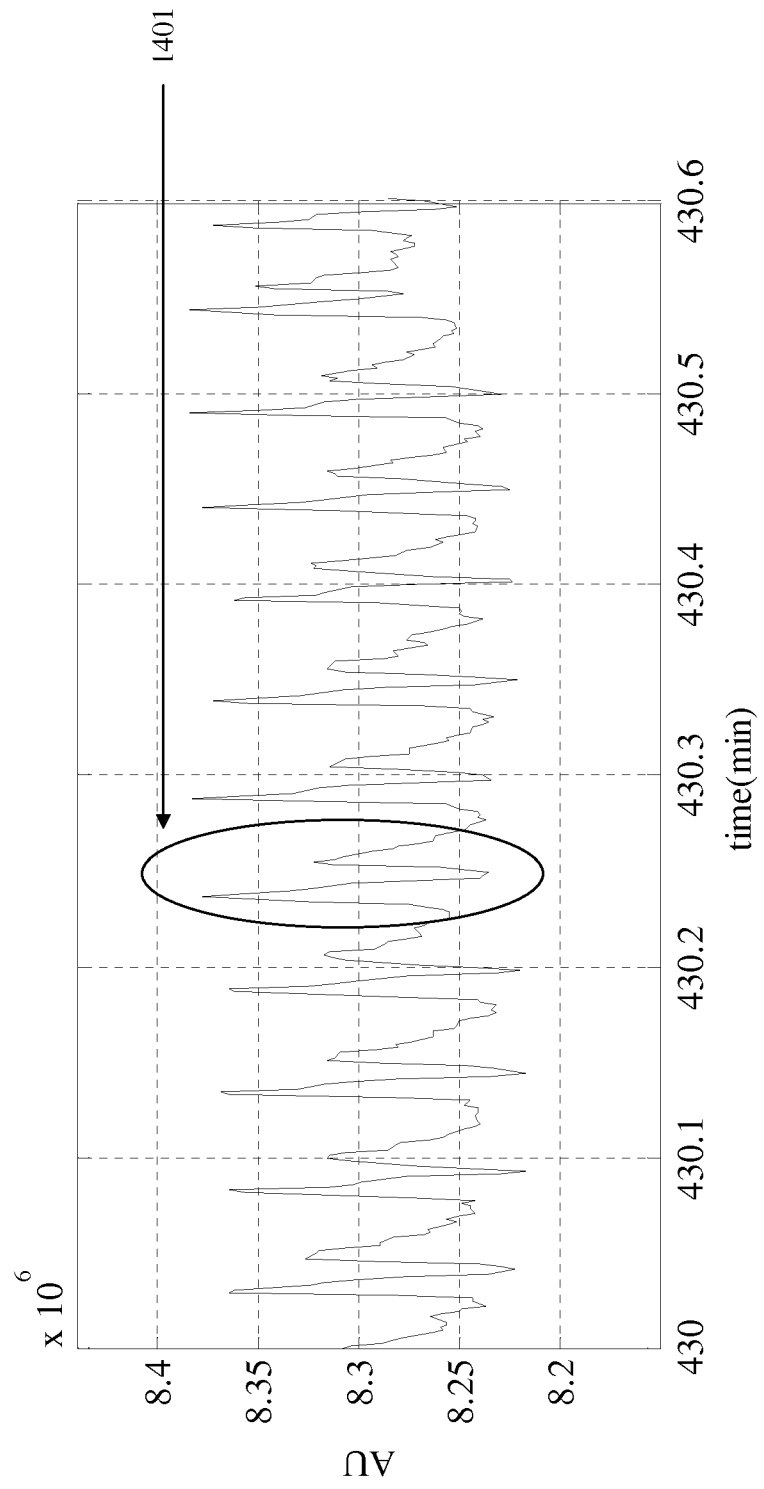
FIG. 11 is a schematic illustration of the respiratory motion signal, measured on a subject with a deteriorating respiratory condition, in accordance with an embodiment of the present invention.
Figure 12:
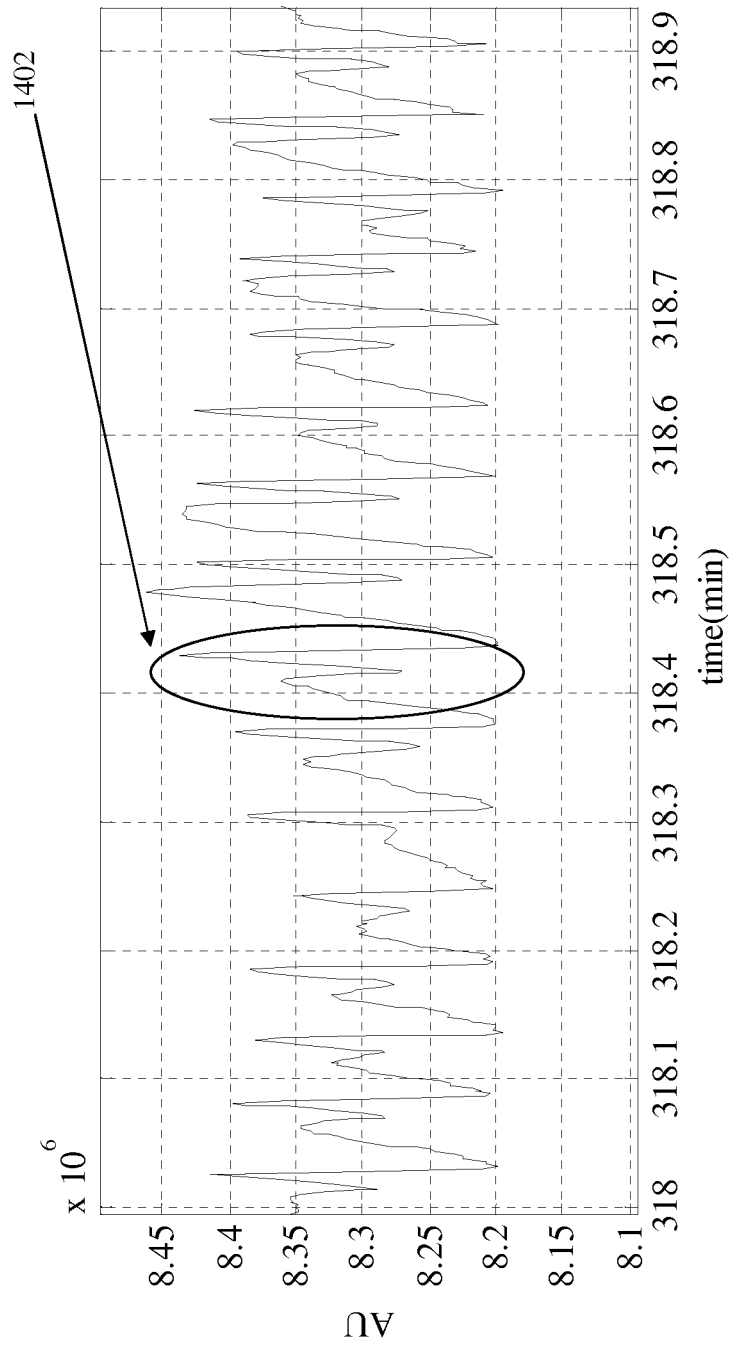
FIG. 12 is a schematic illustration of the respiratory motion signal, measured on a subject with a deteriorating respiratory condition, in accordance with an embodiment of the present invention.
Figure 13:
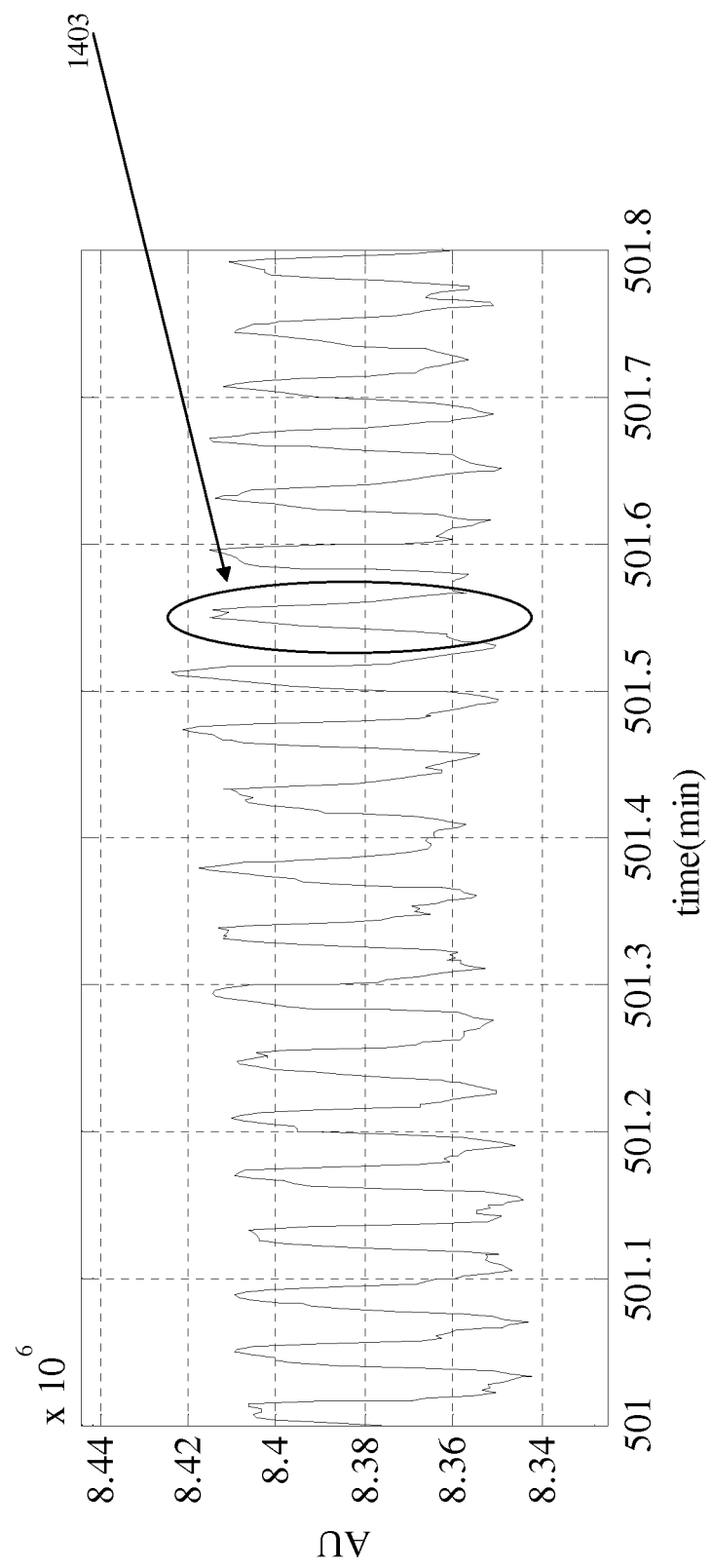
FIG. 13 is a schematic illustration of the respiratory motion signal, measured on a subject with a stable respiratory condition, in accordance with an embodiment of the present invention.

In an embodiment of the present invention, breathing pattern analysis module 22 is configured to detect abnormal breathing patterns that may indicate a deterioration in the patient's condition that is characterized by a respiratory motion pattern that includes a double movement of the chest area during at least some respiratory cycles, which may be indicative of the use of accessory muscles by the subject during the subject's breathing. FIGS. 11 and 12 show breathing patterns that were recorded in accordance with some applications of the present invention, in which each breathing cycle is characterized by defining two distinct subcycles, each of the subcycles defining a distinct peak (see portions 1401 and 1402 of breathing pattern signals shown, respectively, in FIG. 11 and FIG. 12, as compared to a portion 1403 of a normal breathing pattern signal, as shown in FIG. 13). In accordance with some applications of the present invention, a respiratory cycle which defines two subcycles (e.g., as shown in FIGS. 11 and 12) is identified as a Double Movement Respiratory Cycle (DMRC).

In clinical trials performed using an embodiment of the present invention, a DMRC signal has been shown to correlate with serious deterioration of patients' conditions (e.g., as described hereinbelow with reference to FIG. 25), and in several cases with patient death within 24-72 hours. In an embodiment, the system alerts upon detection of such a pattern in at least some respiratory cycles for a period of time of greater than one minute, e.g., greater than 10 minutes, 30 minutes, or 60 minutes, and typically less than 120 minutes.

For some applications, at least one of the following three DMRC-identification criteria is used to determine that a breathing cycle is comprised of two distinct subcycles:

1. Between the two peaks there is a trough whose minimum point is lower than a threshold percentage lower than the average of the two maxima. That threshold is between 50% and 90%, for example 80%.
2. The time between the two peaks is higher than a threshold percentage compared to the overall cycle time. That threshold is between 15% and 45%, for example 30%.
3. The slopes for the rising signals before each of the two peaks are distinctly different from each other. The difference between the two slopes compared to the average of the two is higher than a threshold percentage. That threshold is between is between 30% and 80%, for example 65%. Alternatively or additionally, a similar calculation is repeated for the slopes of the declining signal after the two peaks.

Alternatively or additionally, other criteria are used to determine that a breathing cycle is comprised of two distinct subcycles.

If at least one of the above three criteria (and/or another criterion) is met (and, for some applications, in response to identifying that more than one of the above criteria, and/or other criteria have been met), the current respiration cycle is identified as a DMRC. For some applications, the system determines if the subject is undergoing a DMRC event, in accordance with the following criteria. If for a period of time between 1 and 10 minutes, for example 3 minutes (or greater than 10 minutes, 30 minutes, or 60 minutes), the percentage of respiration cycles that are identified as DMRC out of the total respiration cycles is above a threshold (e.g., between 30% and 80%, for example 60%), then it is determined that the subject is undergoing a DMRC event. Typically, the system logs the event and alerts the clinician and/or the subject that a DMRC event has been identified.

In an embodiment, a DMRC event (as described hereinabove) is interpreted as being indicative of a subject's use of respiratory accessory muscles in the breathing process, which is an indication of a subject's respiratory distress. Thus, for some applications, in response to detecting a DMRC event, a treatment (e.g., administration of oxygen) is applied to the subject, and/or an alert is generated.

In accordance with some applications of the present invention, breathing pattern analysis module 22 includes DMRC-pattern-identification functionality for identifying breathing cycles that are double movement respiratory cycles, e.g., using the DMRC identification criteria described hereinabove. The breathing pattern analysis module further includes DMRC-event-identification functionality configured to identify DMRC events in accordance with the criteria for identifying a DMRC event described hereinabove. In response to identifying a DMRC event, output generation functionality of the system generates an output that is indicative of the subject having undergone a DMRC event, and drives user interface 24 to display the output. For some applications, the system drives the user interface to generate an output indicating that the subject is using accessory muscles for breathing.

Figure 23A:
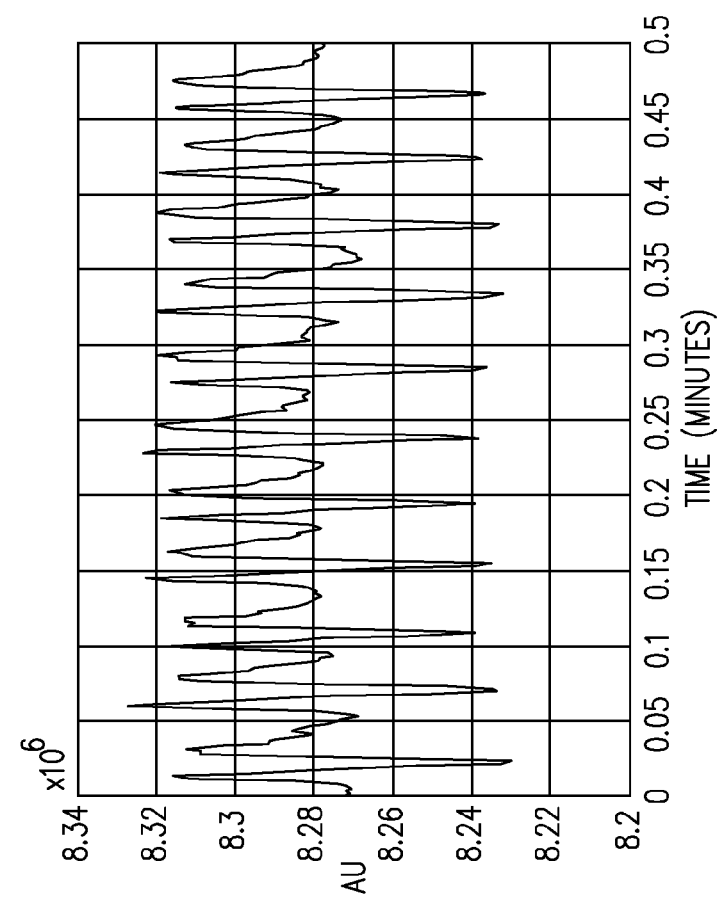
FIGS. 23A-B are graphs showing the respiratory motion signal of a subject, respectively, when the subject is breathing normally, and when the subject is breathing with a double movement respiratory cycle pattern, the respiratory motion signal having been measured in accordance with some applications of the present invention.
Figure 23B:
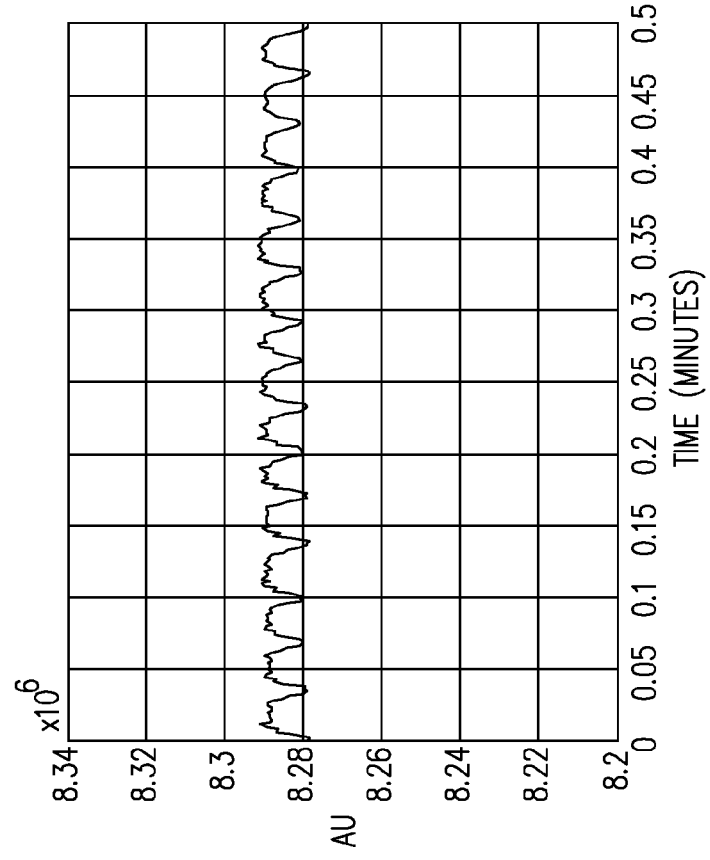

Reference is now made to FIGS. 23A-B, which are graphs showing the respiratory motion signal of a subject, respectively, when the subject is breathing normally, and when the subject is breathing with a double movement respiratory cycle, the respiratory motion signal having been measured in accordance with some applications of the present invention. As may be observed by comparing FIG. 23A to FIG. 23B, in some cases during a DMRC event, the respiratory motion signal has a higher amplitude than the amplitude of the respiratory motion signal when the subject is breathing with a normal breathing pattern. In the example shown in FIGS. 23A-B, the respiration amplitude during the DMRC event is approximately eight times higher than during normal breathing. For some applications, an identification by the breathing pattern analysis module of a significant increase (e.g., an increase of 100% or more) in the amplitude of the respiration may be used as an additional criterion for identifying a DMRC pattern. The inventors hypothesize that this is because, in response to deterioration in respiration, the body may respond by breathing at a greater amplitude, and by using accessory muscles for respiration (which results in a DMRC pattern). It is noted that, although in the example shown, the subject underwent a change in the amplitude of respiration while undergoing breathing with a DMRC pattern, for some applications, a DMRC pattern is detected even in the absence of a change in the amplitude of respiration. Similarly, although in the example shown, the subject underwent a change in the frequency of respiration while undergoing breathing with a DMRC pattern, for some applications, a DMRC pattern is detected even in the absence of a change in the frequency of respiration. Alternatively, a change in the frequency of respiration may be used as an additional criterion for identifying a DMRC pattern.

Figure 24A:
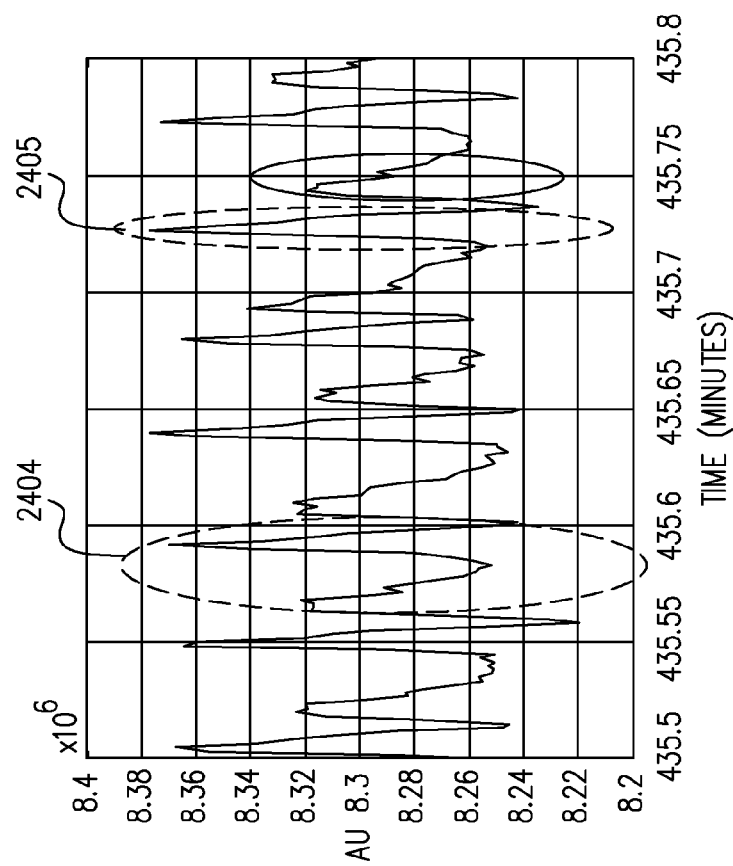
FIGS. 24A-B are graphs showing the respiratory motion signal of a subject when the subject is breathing with double movement respiratory cycles having respective patterns, the respiratory motion signal having been measured in accordance with some applications of the present invention.
Figure 24B:
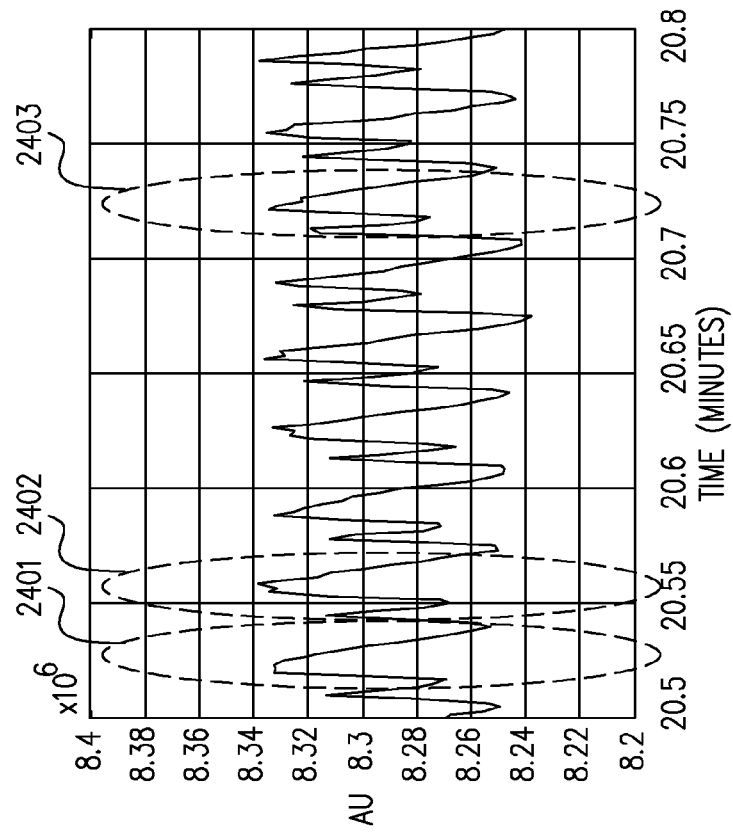

Reference is now made to FIGS. 24A-B, which are graphs showing the respiratory motion signal of a subject when the subject is breathing with double movement respiratory cycles having respective patterns, the respiratory motion signal having been measured in accordance with some applications of the present invention. FIG. 24B shows the respiratory motion signal of the same subject as that of FIG. 24A, the signal in FIG. 24 having been acquired several hours after the signal of FIG. 24A had been acquired. It is noted that when a subject is undergoing breathing with a DMRC pattern, the two subcycles of a single respiration cycle may have respective amplitudes and widths, as seen by comparing subcycle 2406 to subcycle 2405. It is noted that, in general, as shown, the double movement pattern is substantially asymmetrical, i.e., the two subcycles (i.e., the two adjacent sets of peaks and troughs) of a given respiratory cycle are substantially asymmetrical with respect to one another. For some applications, the asymmetry of adjacent subcycles is used as a criterion for identifying a DMRC pattern.

Typically, within a given time period (e.g., within a time period of several minutes), the patterns of respiratory cycles are generally similar to each other, as may be observed by comparing cycles 2401, 2402, and 2403 to each other. However, at a later time period (e.g., one hour or more later), the shape of the pattern may change even though the subject is still breathing with a DMRC pattern, as may be observed by comparing cycle 2403 of FIG. 24A, to cycle 2404 of FIG. 24B, the subject having undergone cycle 2404 several hours after the subject underwent cycle 2403.

Figure 25A:
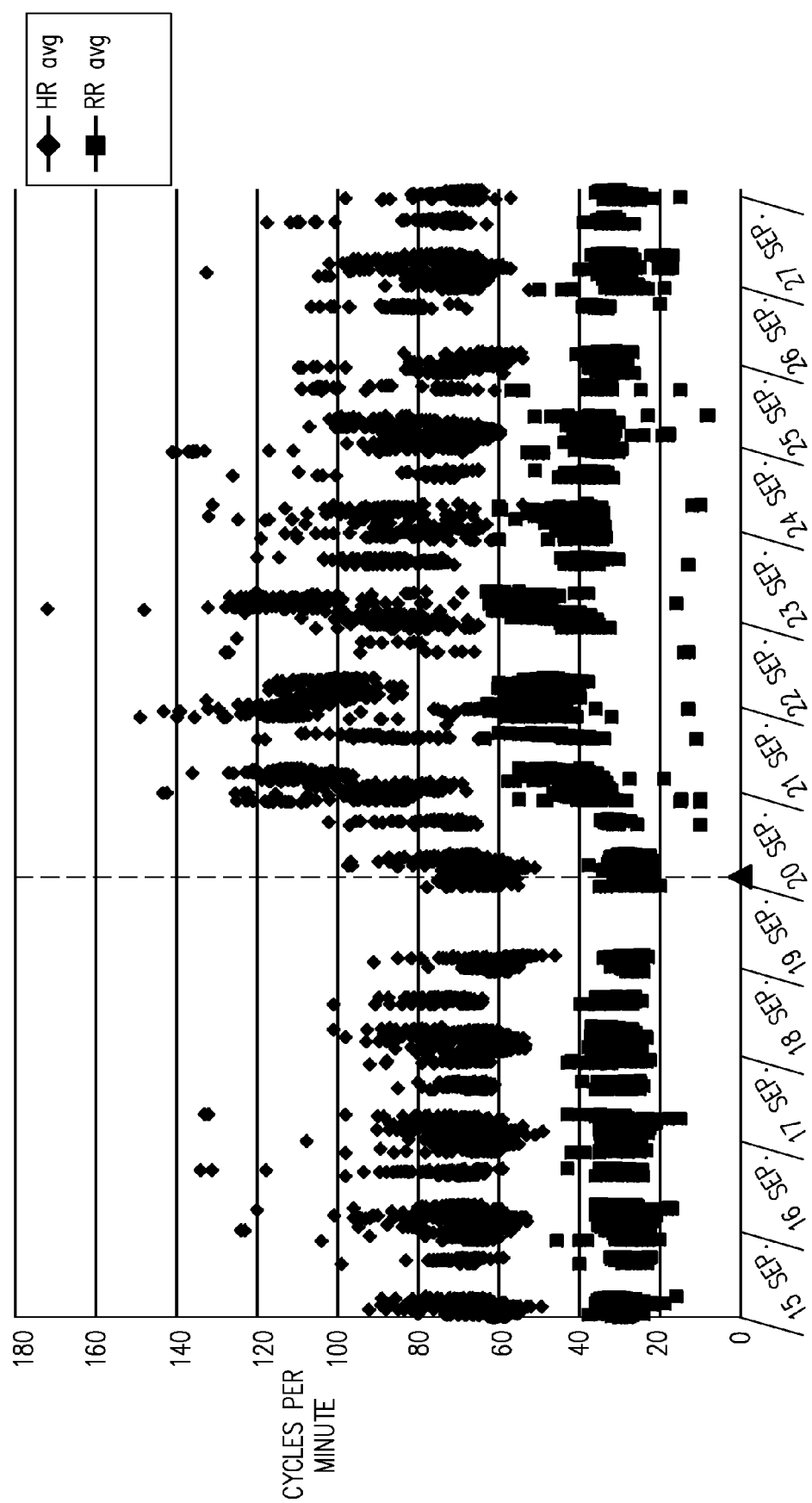
FIGS. 25A-B are graphs showing variations in the heart rate and respiratory rate of a subject, measured in accordance with some applications of the present invention.
Figure 25B:
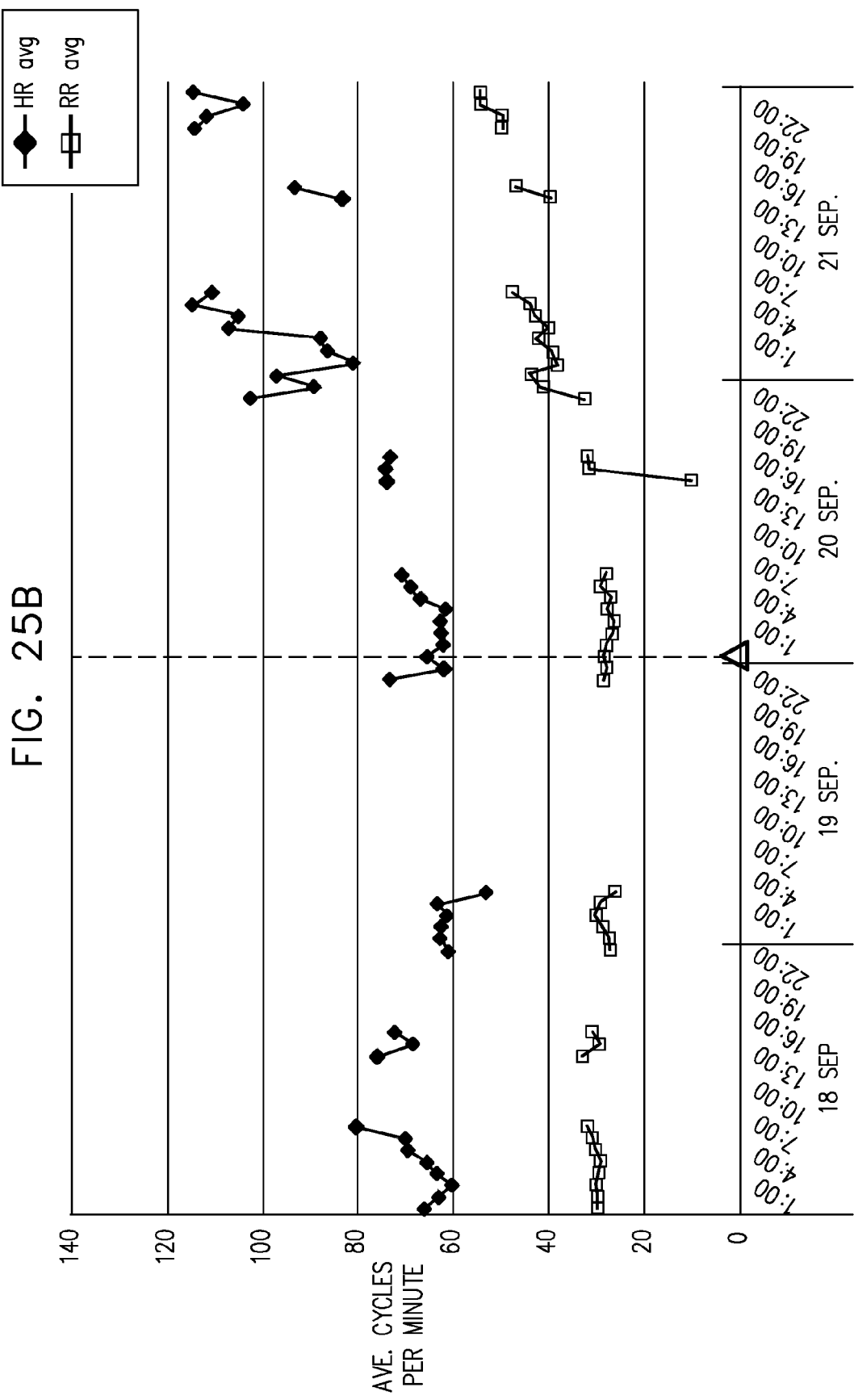

Reference is now made to FIGS. 25A-B, which are graphs showing variations in the heart rate and respiratory rate of a subject, measured in accordance with some applications of the present invention. The subject was a four-year old girl whose heart rate, and respiratory rate were monitored in accordance with some applications of the present invention. FIG. 25A shows data that were collected from September 15 through September 27. It may be observed that there are gaps in the data. This is because the data were collected using a sensor that was placed underneath the subject's bed, and, therefore, the data were only acquired while the subject was in her bed. FIG. 25B shows the data for September 18 through September 21. To generate FIG. 25B, the heart rate data that were acquired each hour were averaged and then plotted. Similarly, the respiration rate data that were acquired each hour were averaged and then plotted. Thus FIG. 25B is a plot of the hourly-average heart rate and respiration rate of the subject.

It may observed that from September 15 to September 19, there were no substantial prolonged changes in the subject's heart rate (which generally varied within a range of 50 cycles per minute to 100 cycles per minute, with a few exceptions). In addition, there were no substantial prolonged changes in the subject's respiration rate (which generally varied within a range of 20 cycles per minute to 40 cycles per minute, with a few exceptions). Shortly after midnight (between 00:20 and 00:50) on September 20, a DMRC event was sensed, and was subsequently identified as a DMRC event, in accordance with the techniques described hereinabove. The DMRC event is indicated by the dotted line and the arrow at around midnight on September 20. Within several hours, the subject's heart rate and respiration rate became elevated. The subject's heart rate and respiration rate continued to increase for the next 24 hours (at which point oxygen was administered to the subject) and remained elevated for a prolonged period. From midnight of September 21 until midnight of September 25, the subject's heart rate generally varied within a range of 60 cycles per minute to 130 cycles per minute, with a few exceptions. The subject's respiration rate generally varied within a range of 30 cycles per minute to 60 cycles per minute, with a few exceptions. Thus, in accordance with some applications of the present invention, a DMRC event of a subject is identified in accordance with the techniques described hereinabove, in order to predict the onset of a clinical episode such as an increased heart rate and/or an increased respiration rate by the subject, and/or to alert a caregiver to a potential medical distress of the subject. For some applications, the DMRC event is identified, in order to predict the onset of a clinical episode (e.g., an increased heart rate and/or an episode of respiratory distress, such as an increased respiration rate) several minutes or hours (e.g., 30 minutes, one hour, three hours, or five hours) before the onset of the condition.

In an embodiment, respiratory rate is continuously monitored. In some cases when a subject exhibits a gasping breathing pattern with high slope of the respiratory motion graph, some respiratory rate analysis algorithms will erroneously detect these patterns as a respiratory rate that is double the actual rate. In an embodiment, system 10 alerts upon an identification of a change in respiratory rate within less than a relatively short amount of time, for example 15 minutes that is close to double the respiratory rate (e.g. between 1.8 and 2.2 times the average respiratory rate) within the previous 15 minutes. For example, if the patient's respiratory rate average is 12 breaths per minute for 3 hours and then the average over 15 minutes changes to 24 breaths per minute, then the system alerts the clinician that there is either a rapid change in respiratory rate or in the respiratory rate pattern that is causing a double respiratory rate reading. In one embodiment, system 10 alerts for such a change only if the patient does not show a simultaneous increase in the amount of large body motions (since those motions, if present, may be the cause for a significant increase in respiratory rate, which is not indicative of patient deterioration).

Patients with sleep apnea are often treated with Continuous Positive Airway Pressure (CPAP) systems. In many cases, it is beneficial to sense the respiration rate and heart rate in order to optimize the use of CPAP devices. In an embodiment of the present invention, the breathing-related signals and heartbeat-related signals which motion data acquisition module 20 extracts (as well as, in some cases, other clinical parameters measured by system 10) are used to optimize the operation of the CPAP device.

In an embodiment of the present invention, motion sensor 30 and all or a portion of motion data acquisition module 20 are packaged in a biocompatible housing (or in multiple housings) configured to be implanted in subject 12. The implantable components comprise a wireless transmitter, which is configured to transmit the acquired signals to an external receiver using a transmission technology such as RF (e.g., using the Bluetooth® or ZigBee protocols, or a proprietary protocol) or ultrasound. Alternatively, one or more of analysis modules 22, 23, 26, 28, 29, or 31, and/or user interface 24 are also configured to be implanted in subject 12, either in the same housing as the other implantable components, or in separate housings. Further alternatively, motion sensor 30 is configured to be implanted in subject 12, while motion data acquisition module 20 is configured to be external to the subject, and to communicate with motion sensor 30 either wirelessly or via wires.

In an embodiment of the present invention, system 10 comprises a plurality of motion sensors 30, such as a first sensor in a vicinity of abdomen 38 or chest 39 (FIG. 1), and a second sensor in a vicinity of legs 40. Pattern analysis module 16 determines a time delay between the pulse signal measured by the sensor under the abdomen or chest and the pulse signal measured by the sensor under the legs. For some applications, the module measures the time delay by performing a cross correlation between the heartbeat signals using a time window less than the respiration cycle time, such as between about 1 and 3 heart beat cycles. Alternatively, for some applications, the module identifies the peaks in the heartbeat signals, and calculates time differences between the signal peaks. Pattern analysis module 16 uses the time differences to calculate a blood pressure change signal on a continuous basis, for example as described in the above-mentioned U.S. Pat. No. 6,599,251 to Chen et al., mutatis mutandis. Module 16 calculates an amplitude of the change in the blood pressure change signal over a full inspiration/expiration cycle, and compares the amplitude to a threshold, such as 10 mmHg, or to a baseline value, either previously measured for the subject or based on a population average. Module 16 interprets amplitudes greater than the threshold as indicative of pulsus paradoxus. Alternatively or additionally, the system displays the amplitude and/or logs the amplitude to form a baseline for the specific subject which is later used to identify a change in condition.

In some cases, an increase in the average delay of the heart beat from the area of the heart to the extremities of the limbs (pulse transit time) vs. earlier readings for the same patient is used as an indication of a deterioration in heart performance.

In an embodiment of the present invention, system 10 comprises one or more mechanical motion sensors as described above (e.g., a piezoelectric sensor) and a pulse oximeter sensor such as the OxiMax® sold by Nellcor of Pleasanton, Calif. The system measures a propagation delay between detection of a pulse signal detected by the mechanical sensor placed under the subject's chest area and detection of a pulse signal detected by the pulse oximeter sensor placed on the subject's finger. For some applications, the system measures this propagation delay using a cross-correlation calculation. The system outputs the delay to user interface 24 and/or logs the delay. In addition, changes in the delay are used as described above for evaluating change in blood pressure, change in cardiac output and detection of pulsus paradoxus. For some applications, the propagation delay is used as one of the clinical parameters, as defined hereinabove, such as for calculating the subject's score. In an embodiment, pulse propagation time is detected using a pair of contactless sensors placed under the mattress. In such an embodiment, the pulse transit time measurement is less susceptible to instantaneous artifacts due to limb movement than with a sensor placed on the finger.

In an embodiment of the present invention, the system uses the propagation delay described immediately above to calculate blood pressure, for example using the pulse transit time method described in the above-mentioned article by Sorvoja, H. and Myllylä, R. for identifying changes in blood pressure. The continuously calculated changes in blood pressure (BP) can be calibrated to measure the absolute BP value if the clinician intermittently measures absolute BP (e.g., every four hours), and enters the BP measurement into the system—this can also be done automatically utilizing an automatic BP cuff. The advantage of this technique is that the system provides a continuous BP measurement, while only needing to squeeze the subject's arm every 4 hours. Alternatively, even if no BP cuff is used, the system can alert a clinician that a subject's BP has undergone an acute change that may require intervention. For some applications, system 10 identifies body movements as described herein and identifies transit time changes that are correlated with body movements as false alarms.

Figure 21A:
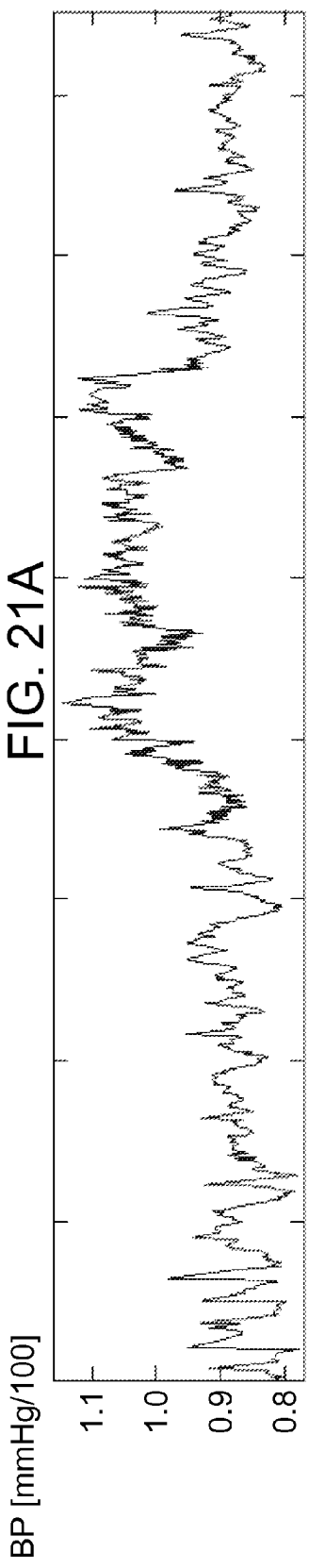
FIGS. 21A-C are schematic illustrations of the Mean Arterial Blood Pressure reference signal (21A), the corresponding Pulse Transit Time (PTT) between an ECG device and a pulse oximeter (21B), and the corresponding PTT between a contactless motion sensor and a pulse oximeter (21C) measured in accordance with an embodiment of the present invention measured on a subject.
Figure 21B:
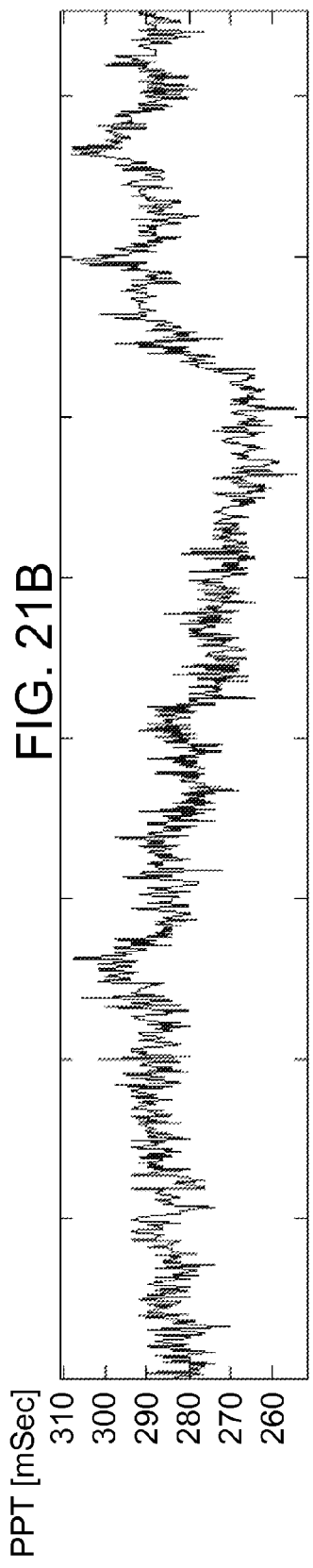
Figure 21C:
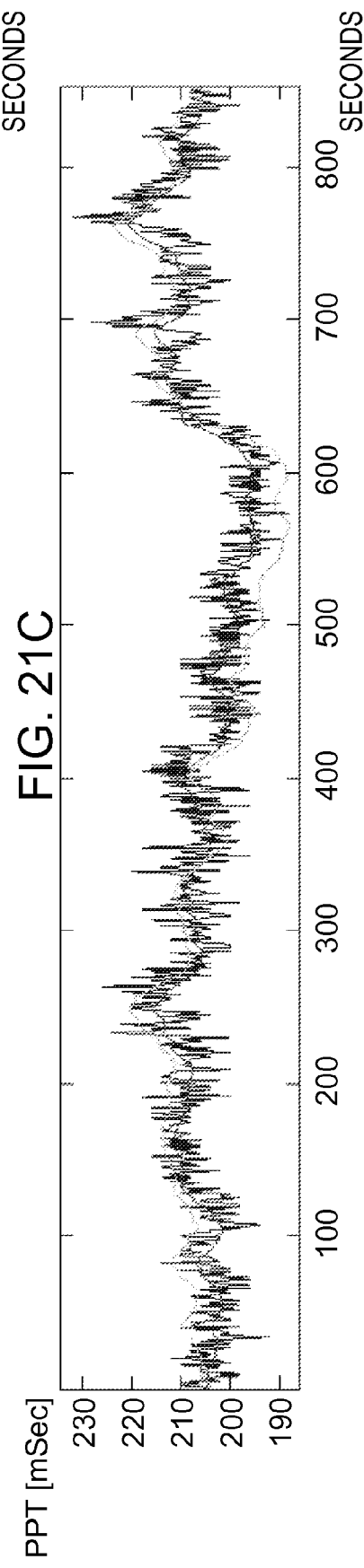

FIGS. 21A-C are schematic illustrations of the Mean Arterial Blood Pressure (MAP) reference signal (21A), the corresponding Pulse Transit Time (PTT) between an ECG device and a pulse oximeter (21B), and the corresponding PTT between a contactless motion sensor and a pulse oximeter (21C) measured in accordance with an embodiment of the present invention measured on a subject. The increase in MAP at time approximately 450-650 seconds clearly causes a reduction in the PTT as shown in 21B and 21C. The decrease in MAP in time 650-800 seconds clearly causes an increase in PTT as shown in 21B and 21C.

In some embodiments of the present application, the system identifies and provides an alert upon detecting a significant change in blood pressure, for example a drop in systolic blood pressure that is considered a warning sign that requires medical intervention, such as for hospitalized subjects.

In previous techniques for measuring blood pressure and/or identifying changes in blood pressure utilizing the pulse transit time methodology, multiple sensors had to be used. The use of multiple sensors makes a system more complex and expensive, and, in some cases, cannot be practically installed on the patient or his surroundings. For example, it is difficult to practically install such a multi-sensor system in a chair where the patient is sitting. In one embodiment, system 10 measures blood pressure and/or identifies change in blood pressure utilizing the pulse transit time methodology utilizing only a single sensor. Typically (but not necessarily), this single sensor is contactless.

As noted, changes in blood pressure (BP) can be measured by calculating pulse wave transit time (PTT) between two reference points in the body. When the BP increases, blood flow also increases and PTT between the two reference points decreases. In the literature, there are references comparing measuring PTT using electrocardiogram (ECG) measurements and photoplethysmograph (PPG) measurements. In an embodiment, PTT is measured between a PPG sensor placed on the finger and a motion sensor placed under the area of the subject's chest. Alternatively, PTT is measured between a motion sensor placed under the area of the subject's chest and a motion sensor placed at some other point, e.g., below the subject's legs. When the PPG sensor is placed on the subject's finger, the measurements may be affected by the subject raising the arm whose finger has the PPG placed on it, because the PTT will decrease without a physiological change in BP. For some applications, an additional tube is used that can facilitate a measurement of the difference in heights between the arm and the chest area. In the case of measurements being made between two mechanical sensors placed under the chest and (for example) below the legs, such an effect may be obtained by changing the angle of the backrest of the bed. Advantageously, such measurements can be easily performed using a measurement system as described herein that is integrated or interfaced with a smart, motorized bed that continuously measures or regulates and can communicate the backrest angle of the bed. Alternatively, the two sensors are placed so that one is under the area of the buttocks/sacrum and one is under the area of the ankles In such a case, there is rarely a significant difference in height when a subject is in bed, and thus no additional measurement is required.

The velocity of progression of the mechanical pulse signal in the body is generally known to be about 4 m/s and may be calibrated per subject as necessary. Knowing the distance between two mechanical sensors and the pulse progression velocity of a pressure wave advancing in the body may be used to locate the heart beat peaks in the mechanical signals. For example, if this velocity is 4 m/s and the distance is 1 m, the approximate difference between peaks in both sensors should be 200 msec.

In one embodiment, the two points for calculating the pulse transit time are calculated using a single mechanical sensor. This sensor is placed in the legs area (or some other area located some distance, for example more than 0.5 m, from the chest. The first point is the time when the aortic valve is opened (valve point') (sometimes two close peaks are found that may indicate two valves, aortic and pulmonary). The pulse is transmitted through the mattress at the speed of sound, i.e., v>330 msec. This means that it will be in effect be received almost immediately by the sensor placed under the mattress, i.e., with a delay of not more than 6 msec from the actual opening of the valve. The second reference point is identified when the pressure wave reaches the sensor (pressure point') through the point of the subject's body located above the sensor (e.g., legs, assuming the sensor is placed under the legs) with a delay of about 200 msec if the distance is 1 meter. Changes in time difference between the 'valve point' and 'pressure point' are used in the pulse transit time calculation to reflect the BP. For these calculations to be performed, the approximate distance between the heart location and the location of the sensor should be known. In one embodiment, this distance is fixed (e.g. 1 meter), and the clinician installing the system is instructed to place the sensor at that distance from the heart (e.g., around the area of the knees, depending the patient's height). In another embodiment, the operator interface enables the clinician to input that distance. Furthermore, for many implementations, an advantage of the system is in identifying the change and the direction of change of BP. Since the subject is unlikely to move substantially in the longitudinal direction in bed, a change in the time delay between the two points is highly likely to indicate a change in blood pressure. In one embodiment, a single mechanical sensor is placed in contact with the subject's body.

In order to identify the 'valve point' and 'pressure point,' in one embodiment the following steps are taken:
1. Pass the signal through a high pass filter of 2-5 Hz (for example, 3 Hz), to filter out respiration-related data from the heart signal.
2. Pass the signal through a low pass filter of 50-150 Hz (for example, 80 Hz) to clean high frequency noise from the signal.
3. Locate all local maxima and minima. Alternatively, the local extremum points can be located on the $1^{st}$ derivative of the signal, which emphasizes sharp changes rather than slow changing extremum points.
4. Using the current measured heart rate for the subject as calculated by heartbeat pattern analysis module 23 (e.g. for the previous 8 seconds), cut the signal into time segments representing a single heart beat (e.g. if the heart rate is 120 bpm then the time segment length is 0.5 seconds).
5. The sharpest local extremum point in a given time segment complex indicates one of two reference points, either 'valve point' or ' pressure point'
6. Using the approximate distance of the distant sensor from the chest, the approximate PTT can be estimated. For example, if the distance is 1 meter and the pulse propagation velocity is about 4 meters per second, then the PTT is 250 milliseconds. As a rough rule of thumb, a change in blood pressure of 10 mmHg is expected to change the pulse propagation velocity by roughly 0.2 meters per second. Thus, for a one meter spacing between the heart and the sensor, a 10 mmHg change in BP is expected to cause a change in PTT of roughly 12 milliseconds. Since the measurement is continuous, the PTT from one calculation to the next is not expected to change by more than 10 milliseconds. This is useful in identifying the correct extrema in the signal by looking for the extrema with the appropriate time difference between them.
7. Find the closest matching extrema that are spaced with the above approximated time difference.
8. Validate both points by calculating the difference between consecutive 'valve' points and consecutive 'pressure' points in the following time segments—they should be spaced 1 heartbeat time apart from each consecutive respective point. In addition, measure the time difference between the 'valve point' and 'pressure point' in consecutive segments—this distance should remain relatively constant.
9. Measure the difference between these 'valve' and 'pressure' points—this is the PTT. Use the obtained PTT in order to calculate the change in blood pressure.

FIGS. 22A-B show the valve point and pressure point as measured with an embodiment of the present invention. FIG. 22A shows the ECG signal (dashed line) and corresponding signal from a contactless motion sensor placed under the area of the chest (solid line), measured in accordance with an embodiment of the present invention on a subject. FIG. 22B shows the ECG signal (dashed line) and corresponding signal from a contactless motion sensor placed under the area of the legs (solid line), measured simultaneously with FIG. 22A, in accordance with an embodiment of the present invention. 1491 and 1495 are the R peaks of the QRS complex, and 1493 and 1496 are the peaks of the T wave of the ECG signal measured on the subject. 1492 and 1497 are the extrema of the mechanical signal identified as the 'valve point' by an embodiment of the present invention. 1492 and 1497 are sensed by both sensors close to simultaneously. Peak 1494 is the 'pressure point' as detected by the sensor in the area of the subject's legs. The difference in time between 1494 and 1497 (approximately 250 msec) is the PTT.

It is noted that in the context of the "single sensor" detection of blood pressure described immediately hereinabove, the scope of the present invention includes using a single sensor assembly placed (for example) under the subject's legs, without placing any sensor for use in this calculation below the subject's heart. The sensor assembly itself, however, may comprise one or a plurality of sensors. For example, the sensor assembly may comprise two sensors, aligned along a line which generally points toward the subject's heart (e.g., aligned along the longitudinal axis of the bed), the two sensors typically being 10-30 cm, for example 25 cm apart. A propagating pulse is detected by the two sensors at different respective times. If the techniques described hereinabove for detecting valve point and pressure point were not utilized, a small sensor assembly having two sensors would typically not generate sufficient temporal resolution to accurately determine PTT. Using the techniques described herein for identifying valve point and pressure point, however, allows the known longitudinal offset between the two sensors in the sensor assembly to reduce error in measurement of PTT, when combined with the identification of the valve point.

In some cases, a pulse oximeter may give erroneous readings without any visible warning. This may happen, for example, because of poor perfusion. In an embodiment of the present invention, system 10 comprises the above-mentioned pulse oximeter and a mechanical sensor. System 10 calculates the subject's heart rate using both the pulse oximeter signal and the mechanical sensor's signal. The system compares the two calculated heart rates to verify that the measured heart rate is correct. If there is a mismatch, the system alerts a healthcare worker.

The pulse signal detected by the pulse oximeter is modulated by the subject's respiration cycle. In an embodiment of the present invention, system 10 uses the level of modulation of the pulse signal detected in the pulse oximeter during a respiratory cycle to evaluate whether the subject suffers from pulsus paradoxus. For some applications, in order to identify this modulation, the system measures the respiratory signal using the mechanical sensor described above. The system analyzes the signal to find the frequency and timing of the respiratory cycle, and, accordingly, to measure the depth of the modulation of the pulse signal by the respiratory cycle. For some applications, the system uses a technique similar to that described in U.S. Pat. No. 5,743,263 to Baker, mutatis mutandis, except that the respiration rate, instead of the heart rate, is used as a virtual trigger.

In an embodiment of the present invention, system 10 uses the heart rate as detected by a contactless mechanical sensor as described hereinabove in order to improve the signal-to-noise ratio in the pulse oximeter reading. For example, the heart rate is used as a virtual trigger in a similar manner to the technique described in U.S. Pat. No. 5,743,263 to Baker. Alternatively, the exact timing of the pulse signal as measured by the contactless mechanical sensor is used to trigger the heart beat synchronization process, in order to improve the signal-to-noise ratio in the pulse oximeter signal.

In an embodiment of the present invention, system 10 is configured to monitor breathing and pulse (or heartbeat) patterns in order to recognize Central Sleep Apnea (CSA) episodes.

In an embodiment, system 10 comprises a Positive Airway Pressure (PAP) device. Upon detecting that the subject has fallen asleep, the system activates the PAP device. Alternatively, the system activates the PAP device a predefined period of time after the system identifies quiet breathing, so as to facilitate the falling asleep of the subject, which may be compromised by the activation of PAP. For some applications, techniques of this embodiment are used to treat a subject suffering from obstructive sleep apnea (OSA), without preventing the subject from falling asleep.

In an embodiment of the present invention, system 10 continuously monitors the heart rate of subject 12 during sleep. The system identifies and logs short-term substantial increases in heart rate. For example, pattern analysis module 16 calculates average heart rate for each minute and the average for the previous 10 minutes. The system identifies the occurrence of an event upon detecting that the average heart rate in the current minute is at least a certain percent greater than the average of the previous 10 minutes, e.g., between about 5% and about 30%, such as about 10%. The system logs the number and severity of such events, and uses the events as an additional clinical parameter, as defined hereinabove. In some cases, the occurrence of such events correlates closely with drops in blood oxygen saturation level. Alternatively, the number and severity of such events is logged for a COPD subject, and a significant change is used as an indication of a change in the subject's clinical condition. For some applications, system 10 builds a baseline of the characteristics of such peaks or troughs in heart rate for a subject over one or more nights, and alerts the subject or a healthcare worker upon detecting a clear change in the characteristics of such peaks, e.g., the height, frequency or distribution over the sleep period. In one embodiment, such peaks are further analyzed and categorized according to whether they occur simultaneously with or in close proximity after large body motions. In one embodiment, only those cases which are not preceded by large body motion are reported to the clinicians.

In an embodiment of the present invention, system 10 is configured to receive a specified range of values for a clinical parameter, such as heart rate or respiration rate. Responsively to the motion signal sensed with motion sensor 30, the system calculates a value of the clinical parameter of the subject at least once every 10 seconds, during a period having a duration of at least 30 seconds, e.g., at least 60 seconds, or at least one hour. Only upon finding that the value falls outside the specified range over 50% of the times it is calculated throughout the period, the system generates an alert. For some applications, this technique is used to monitor subjects having a condition such as pneumonia, COPD, CHF or some other condition other than apnea or SIDS.

In an embodiment of the present invention, system 10 is configured to receive a specified range of values for a clinical parameter, such as heart rate or respiration rate. Responsively to motion sensed with motion sensor 30, the system calculates respective raw values of the clinical parameter of the subject at least once every 10 seconds, during a period having a duration of at least 30 seconds, e.g., at least 60 seconds, or at least one hour. The system calculates a representative value based on the raw values, such as a mean or median of the raw values, or another representative value based on the raw values (e.g., including discarding outlying raw values). Only upon finding that the representative value falls outside the specified range, the system generates an alert.

In an embodiment of the present invention, system 10 is configured to receive an indication of a baseline value for a clinical parameter, such as heart rate or respiration rate. Responsively to motion sensed with motion sensor 30, the system calculates a value of the clinical parameter of the subject at least three times, e.g., at least 10 times, during a period having a duration of at least 10 seconds, e.g., at least 30 seconds, at least 60 seconds, or at least one hour. Only upon finding that the value is at least a threshold percentage different from the baseline value over 50% of the times it is calculated throughout the period, the system generates an alert. For some applications, this technique is used to monitor subjects having a condition such as pneumonia, COPD, CHF, or some other condition other than apnea or SIDS.

In an embodiment of the present invention, system 10 is configured to receive an indication of a baseline value for a clinical parameter, such as heart rate or respiration rate. Responsively to motion sensed with motion sensor 30, the system calculates respective raw values of the clinical parameter of the subject at least three times, during a period having a duration of at least 10 seconds, e.g., at least 60 seconds, or at least one hour. The system calculates a representative value based on the raw values, such as a mean or median of the raw values, or another representative value based on the raw values (e.g., including discarding outlying raw values). Only upon finding that the representative value is at least a threshold percentage different from the baseline value, the system generates an alert.

Subjects undergoing cytotoxic chemotherapy are at high risk of suffering from CHF and/or pulmonary edema. In an embodiment of the present invention, system 10 is used to monitor subject 12 during and after receiving chemotherapy treatment and to alert the subject or a healthcare worker upon detection of a clinical indication of impending CHF or pulmonary edema.

In an embodiment of the present invention, system 10 is used to monitor subjects suffering from renal failure. System 10 identifies changes in vital signs or other measured parameters (e.g., increase in heart rate and respiration rate or reduction in sleep quality) (indicated, for example, by frequency and amplitude of large body motions during the hours of midnight through 6:00 AM) that indicate that a subject may need dialysis treatment or other intervention.

Pulmonary hypertension is characterized by elevated blood pressure in the pulmonary arteries from constriction in the lung or stenosis of the mitral valve. The condition adversely affects the blood flow in the lungs, and causes the heart to work harder. In an embodiment of the present invention, system 10 is used to monitor subjects suffering from pulmonary hypertension and to identify the onset and/or deterioration of their condition. System 10 monitors the clinical parameters and identifies a change that may indicate such a deterioration, for example an increase in respiration rate or heart rate.

In an embodiment, system 10 detects changes in respiration rate, heart rate, large body motions, and tremor that indicate that in a subject known to be likely to experience pain (e.g., admitted to the hospital for pain treatment) the subject is actually suffering from pain. For some applications, upon detection of pain, the system activates a drug administration device 84 (FIG. 2) in order to alleviate the pain automatically with the appropriate medication.

Blood oxygen saturation level is an important indicator of a patient's condition. However in some cases, a drop in blood oxygen saturation is a relatively late indicator that is preceded by changes in respiration, heart and motion patterns. For example, in patients receiving oxygen support, blood oxygen saturation drop is often a late indicator of respiratory failure. Reference is again made to FIG. 2. In an embodiment of the present invention, system 10 comprises a blood oxygen monitor 86 (e.g., a pulse oximeter). System 10 monitors a respiration pattern of the subject, a heart rate pattern of the subject, or a respiration motion pattern of the subject (which includes the depth of each breath) (or a combination of two or more of these patterns) while monitoring the subject's blood oxygen level using blood oxygen monitor 86. The system uses learning techniques to identify one or more characteristic patterns associated with an impending change in the blood oxygen level. Upon detecting at least one of the learned characteristic patterns that precede changes in blood oxygen level, the system generates an alert to the subject or a healthcare worker. The system thus serves as an early warning system for change in blood oxygen level. Optionally, even when not performing learning, the system uses this pattern-monitoring technique, in combination with blood oxygen monitor 86, in order to provide an earlier warning of an impending change in blood oxygen than is possible using the blood oxygen level meter alone. For some applications, the system uses blood oxygen monitor 86 only for learning the characteristic respiration or heart rate patterns, and not during subsequent monitoring of the subject for an impending change in blood oxygen level.

For some applications, system 10 interprets a change in respiratory rate and a change in respiratory pattern as indicative of a high probability of an impending deterioration in blood oxygen level. For example, an increased respiratory rate combined with shallow breaths or DMRC in a resting patient may provide such an indication. An increased heart rate in conjunction with these changes serves as an additional indication of a high likelihood of a decline in oxygen saturation.

In an embodiment of the present invention, system 10 combines the information regarding blood oxygen measured using blood oxygen monitor 86 with information regarding respiration rate and/or heart rate measured using motion sensor 30, to generate a combined clinical score. When the score crosses a threshold, the system generates an alert that the subject is at risk of respiratory distress. For some applications, system 10 also calculates a clinical parameter of breathing irregularity. For some applications, the system calculates a baseline for the subject for each of the measured parameters over a baseline period of time (e.g., less than an hour, such as between about 15 and about 45 minutes, or more than about an hour). The system calculates the clinical score using, for example, the following equation:

$$S=5(100-Ox)-k1*\text{Delta}RR-k2*\text{Delta}HR+k3*\text{RESPIrreg} \quad \text{(Equation 7)}$$

wherein:
- S—clinical score
- Ox—blood oxygen saturation level in percent
- DeltaRR—percentage change in respiration rate versus baseline
- DeltaHR—percentage change in heart rate versus baseline
- RESPIrreg—percentage change in respiration irregularity versus baseline.
- k1, k2, k3—coefficients for the respiration and heart rate parameters. Typically k1, k2 and k3 are between about 0.6 and about 1.4.

In some cases, especially when the heart rate is relatively low, higher harmonics of the respiration rate may appear in the spectrum of the heart channel and may affect the measurement of the heart rate. In an embodiment of the present invention, system 10 uses a band pass filter to eliminate most of the respiratory harmonics (as well as the basic frequency of the heart rate), using, for example, a pass band of between about 2 Hz and about 10 Hz. In a Fourier analysis of the resulting signal, the basic frequency of the heart rate is no longer the highest peak. However, the harmonics of the heart rate signal are still present as peaks. Heart beat pattern analysis module 23 identifies these peaks and calculates the heart rate by calculating the distance between consecutive peaks.

In another embodiment, system 10 calculates the heart rate using an amplitude demodulation method. In this method, a band pass filter which rejects the basic heart rate frequency as well as most of the respiratory harmonics is used. For example, the band pass filter may be tuned to between about 2 Hz and about 10 Hz. The absolute value of the filtered signal is calculated, and a low pass filter with appropriate cutoff frequency (e.g., about 3 Hz) is applied to the absolute value signal result. Finally, the system calculates the power spectrum and identifies its main peak, which corresponds to the heart rate.

Tremor Measurements

There are multiple clinical uses for the measurement of tremor. One application is the monitoring of diabetic subjects to identify hypoglycemia. In an embodiment of the present invention, system 10 identifies the signal associated with heart rate and respiration rate. The system subtracts the heart rate and respiration rate signal from the overall signal. The resulting signal in those areas where there are no restlessness events is regarded as the tremor signal for the analysis described above. For some applications, the energy of the tremor signal is normalized by the size of the respiration and/or heart signal.

Typically, tremor-related body vibrations occur in a frequency band of between about 3 and about 18 Hz. In an embodiment of the present invention, motion data acquisition module 20 and pattern analysis module 16 are configured to digitize and analyze data at these frequencies. The system attributes a significant change in the energy measured in this frequency range to a change in the level of tremor, and a change in the spectrum of the signal to a change in the spectrum of the tremor.

In one embodiment, system 10 is used to identify the cessation of breath and heart signal using mechanical sensor 30. Other standard monitoring technologies, e.g., ECG, often fail this task since after death, the heart still produces some electrical activity that is mistaken by an ECG monitor as a signal. In one embodiment, system 10 is used to identify the cessation of heart and breathing motion signals. In one embodiment, the measurement using mechanical sensor 30 is characterized by large signals (compared to the breathing and heart related signals) due to large body movements, speaking or some other activity. In those cases, absence of heart rate and respiration signal detection results does not necessarily means cardiac death. In one embodiment, system 10 implements an additional criterion to detect cardiac death. When the heart and breathing related motion signals disappear, (or become very weak), the tremor signal can be detected as significantly higher than all other signals. If there is a tremor signal, but no heart and breathing related motion, this is utilized by system 10 as an indication of cardiac death. In one embodiment, a frequency analysis of the detected mechanical signal is performed. For example, short window time frames are used (not more than 30 sec to allow quick detection of cardiac death). System 10 identifies whether a tremor related peak in the frequencies of 3-7 Hz is found in the power spectrum. Such a peak is identified in the power spectrum as a wide peak which is not characteristic of a sinusoidal signal (such as that which would be characteristically generated by respiration related motion and its harmonics). If system 10 identifies such a peak that is significantly higher than the energy found in the 0.05 Hz-3.0 Hz where the respiratory and heart related motion signal is found, then system 10 identifies that the tremor related signal is higher than respiratory or heart related signal and an appropriate alert is generated for a healthcare professional. FIG. 5 shows the signal detected by sensor 30 in a clinical trial during a time shortly following a subject's death. Line 1210 shows the signal in the time domain and line 1211 in the frequency domain as analyzed by system 10. Line 1211 shows the peak related to the tremor after death which is higher than any other signal in the spectrum since no breathing and heart related motion is present. In an embodiment of the present invention, system 10 is configured to identify large body movement of subject 12. Large body movements are defined as having an amplitude that is substantially greater (e.g., at least 5 times greater) than that of respiration-related body movement, and/or having frequency components that are higher than those of respiratory motion (e.g., frequencies greater than about 1 Hz). For some applications, the system extracts relative and absolute movement time and amplitude parameters from the mechanical signal. The signal pattern prior to movement corresponds either to regular breath (when the subject is in the bed) or to system noise (the subject is entering the bed). The signal pattern during large body movement is characterized by high amplitude in the range of 5 to 100 times greater than regular breath amplitudes, and by rapid signal change from maximum positive value to minimum negative value. The initial large body movement phase that includes the transition from the pattern corresponding to regular breath or system noise to the movement pattern typically has a duration of about 0.5 seconds. The typical duration of the large body movement event ranges between 10 and 20 seconds. The dynamics of the initial phase are characterized by change of signal to maximum amplitude during one second. During the initial phase of the large body movement, increase in amplitude is typically in the range of 10 to 100 times greater than the maximum value corresponding to regular breath pattern.

In an embodiment of the present invention, system 10 identifies the start of the large body movement event by detecting the initial movement phase, and the end of the movement event when the movement phase concludes. For some applications, the system performs real-time signal analysis by evaluating sliding overlapping windows, and identifying the initial movement phase as occurring during a window characterized by at least one of the following ratios, or, for some applications, by both of the following ratios:

a signal-to-noise ratio (SNR) that is less than a threshold value; and a ratio of the signal standard deviation (STD) during the window to the signal STD during a window characterized by a typically respiratory signal (e.g., the most recent window in which a respiratory signal was detected), which is greater than a threshold value.

To calculate the SNR, the system typically calculates the power spectrum, and sets the SNR equal to the ratio of: (a) the energy in a specific frequency interval in the respiratory range (e.g., between about 0.1 and about 1 Hz) to (b) the energy of the noise in the entire spectrum excluding the respiratory range—i.e. in order to calculate the SNR, the value of (a) is divided by the value of (b). The frequency interval is similar to the range of respiration rates detected by the system. The system typically specifies a window size such that each window includes at least one respiratory cycle (e.g., 5 seconds if the breathing rate is 12 breaths/minute). For some applications, the system adaptively sets the window size, while for other applications the system fixes the window size according to the lowest allowed respiratory rate.

Alternatively, the system performs the detection of the initial phase of the large body movement by dividing the time window into small windows having a duration of between about 0.25 and about 0.75 seconds (with or without overlapping). For each window, the system calculates a set of parameters based on the signal variance within the window. For some applications, the system sets the variance equal to the sum of absolute values of pairs of sequential samples differences normalized by the square root of the number of samples in the window. The system compares the variance parameter to a threshold, and if the variance parameter is greater than the threshold, the system identifies the window as including a large body movement.

In an embodiment, system 10 is configured to detect bed entry and/or exit by subject 12. The system identifies bed entry upon detecting large body movement followed by a signal indicative of continuous motion (e.g., related to respiration or heartbeat), and bed exit upon detecting large body movement followed by a lack of motion signal. For some applications, sensor 30 comprises a single semi-rigid plate, and, coupled thereto, a vibration sensor and two strain gauges that are configured to detect the weight the subject's body applies to sensor 30.

In an embodiment, system 10 is configured to alert if subject 12 has left the bed and has not returned for a time period that is higher than a specified length of time between 3 minutes and 2 hours, for example 10 minutes. This may be manually or automatically activated for patients for specific times of day, for example during the night. This is useful for supervising patients who may enter or exit the bed independently but may be at risk of falling. The nurse may not want to be alerted every time the patient leaves the bed, but may want to be alerted if the patient left bed and has not returned for 10 minutes, since that could mean that the patient fell and requires assistance or is wandering in the hospital or nursing home with no escort. The nurse may, for example, want this system activated only at night when the nursing team is smaller and the patients are expected to stay in bed practically all the time except for brief bed exits. This 'long time bed exit alert' is valuable for reducing the number of alerts and thus "alert fatigue," while effectively notifying nursing teams of unusual situations that may require interventions.

In an embodiment, system 10 monitors heart rate and additional physiological parameters such as respiration rate and motion level. If over a significant period of time between 1 minute and 6 hours (for example, 15 minutes) the respiratory rate is measured with a good quality signal and/or there is no large body motion detected and the heart rate is not consistently measured using the methods described herein, this may be an indication for an unstable heart rate, e.g. atrial fibrillation. System 10 then alerts of an unstable heart reading and in some embodiments additionally displays a recommendation to the clinician to connect the patient to an ECG device.

For some subjects, it is useful to identify an instability in the heart rate that may be an indication of cardiac arrhythmia. In some cases, alerting a clinician on every event of high heart rate variability may cause an unacceptable level of false alerts, as many such events may be caused by patient motion or agitation. In an embodiment, system 10 monitors heart rate and respiration rate. If over a significant period of time between 1 minute and 1 hour (for example, 15 minutes) the respiratory rate is stable (for example, the standard deviation of the respiratory rate readings is less than 5% of the average rate for that time period) and there is no large body motion detected and the heart rate shows high variability (for example, the standard deviation of the heart rate readings is more than 8% of the average for that time period and there is no trend of decrease or increase in heart rate), this may be an indication for an unstable heart rate, e.g., atrial fibrillation. System 10 then alerts of an unstable heart reading and in some embodiments additionally displays a recommendation to the clinician to connect the patient to an ECG device.

In one embodiment, system 10 includes the mattress itself that is designed to optimally transfer the mechanical signal to the piezo-electric sensor and thus becomes part of the sensing element. For example, in one embodiment, the sensor is integrated into a dynamic, non-powered mattress such as the AtmosAir9000 manufactured by Kinetic Concepts. The mattress' self adjusting technology that maximizes subject's body surface area in contact with the mattress leads, in some embodiments, to an improved signal detected by the system.

In an embodiment, system 10 is used to monitor subjects during transport on a stretcher. The sensor is implanted within the fabric of the stretcher and continuously monitors the subject during transport. System 10 generates an alert upon detecting an acute change in subject condition without requiring any activation by the clinician or any compliance by the subject.

Rapid Change Detection

In an embodiment of the present invention, system 10 is configured to identify a change in the condition of at least one subject in a hospital, such as in a surgical or medical ward, such as by using techniques described in U.S. patent application Ser. No. 11/782,750, which is assigned to the assignee of the present application and incorporated herein by reference. The change typically includes a deterioration that requires rapid intervention. System 10 typically identifies the change without contacting or viewing the subject or clothes the subject is wearing, without limiting the mobility of the subject, and without requiring any effort by the nursing staff or other healthcare workers. For example, upon detecting a decrease in the subject's respiration rate to below eight breaths per minute, which may be a sign of respiratory depression, the system may generate an alert to a nurse. For some applications, the system is configured to predict an onset of a clinical episode, and to generate an alert.

For some applications, system 10 monitors the subject in the hospital automatically upon entry of the subject into a subject site such as a bed. Typically, system 10 does not require activation by a nurse or other healthcare worker, and no compliance by the subject is required other than to be in bed. Typically, motion sensor 30 is contactless (i.e., does not contact the subject or clothes the subject is wearing), and operates substantially continuously. When the subject enters the bed, the sensor detects the vibrations or other movements generated by the subject and initiates monitoring. Alternatively or additionally, the system uses the technique described hereinabove for detecting bed entry. The system alerts clinicians upon any change that may require intervention. For example, the system may send an alert to a nurse, a member of a rapid response team, or other healthcare worker, such as wirelessly, e.g., to a wireless communication device, such as a pager, or using another call system in the hospital. For some applications, upon receiving the message, the wireless communication device sounds an audible alert, e.g., including an automatically generated voice message that includes the subject's name or number, room number, and/or alert type. This enables a clinician to act upon the alert and/or assess the situation without having to handle the pager (which is useful in situation where the clinician's hands are busy).

For some applications, when the subject enters the bed, system 10 initially uses a preset threshold for alerts. Over a period of time, e.g., one hour, the system establishes a reference baseline, e.g., the average respiration rate over that time period. Once the baseline has been established, upon identifying a change (e.g., a rapid change) in a clinical parameter versus the baseline, the system alerts a clinician. For example, the system may generate an alert upon detecting a change of 35% in a clinical parameter rate within a 15 minute period.

For some applications, the system makes a decision whether to generate an alert responsively to at least one clinical parameter selected from the group consisting of: a current value of the clinical parameter, a change in the clinical parameter versus baseline, and a rate of change of the clinical parameter over a relatively brief period of time, such as over a period of time having a duration of between about 2 and about 180 minutes, e.g., between about 10 and about 20 minutes. For some applications, the system uses a score which combines two or more of these parameters. For example, the score may include a weighted average of two or more of the parameters, e.g.:

$$\text{Score}=K*\text{Param}+J*\text{DeltaParam}+L*\text{DeltaParamRate} \quad \text{(Eq. 19)}$$

wherein K, J, and L are coefficients (e.g., equal to 1, 0.2, and 0.4, respectively); Param is the current value of the clinical parameter, for example respiration rate or heart rate; Delta-Param is the difference (e.g., expressed as a percentage) of the parameter versus the subject's baseline; and DeltaParamRate is the change in percent of the parameter between the current time and that in a previous time period, for example between about 10 and about 20 minutes earlier, e.g., about 15 minutes earlier. Typically, Param has a unit of measurement, e.g., breaths per minute, or heartbeats per minute, while Delta-Param and DeltaParamRate do not have units. For some applications, Param is normalized, such as by dividing the measured value by the baseline value and multiplying by a constant, e.g., 100. For example, the upper and lower thresholds for Score (if Param is normalized) may be set to 65 and 135, respectively, for monitoring respiration rate. If Score falls outside the range between the thresholds, the system generates an alert. In an embodiment, sensor 10 is implemented inside the mattress of the bed, thereby adding no visible extra parts to the bed.

In some embodiments of the present invention, including the embodiment described immediately above, it is generally desirable to minimize alarms, especially alarms that activate the nurse call system and are heard throughout the ward in a hospital. In an embodiment, upon identifying cause for alert, system 10 first activates a local alarm in the subject's room for a brief period of time, e.g., 30 seconds. User interface 24 of system 30 comprises a deactivation control, such as a button, that allows a clinician who is in the room to deactivate the alarm, thereby preventing the activation of an alarm throughout the entire hospital ward. After the brief period of time, if the local alarm was not deactivated by a clinician, the system generates the general alert.

For some applications, sensor 30 is installed in a subject site such as a chair near the subject's bed.

For some applications, the system deletes the baseline upon detecting that the bed is empty for a certain period of time, e.g., one hour, which may indicate that the subject has left the bed and a new subject has entered the bed.

In an embodiment of the present invention, system 10 comprises one or more of the following sensors: a urine output sensor, a temperature sensor (wired or wireless), and a blood pressure sensor.

In an embodiment of the present invention, system 10 is used to monitor subjects and generate an alert upon detecting a deterioration. For some applications, pattern analysis module 16 is fed information about patterns of specific types of deteriorations, such as pulmonary embolism, hypoglycemia, and alcohol withdrawal. The clinician selects for which types of conditions the subject is at risk, and the system looks up a set of parameters appropriate for the selected conditions, and generates an alert for these conditions. For example, tachycardia, palpitations, tremor, agitation in sleep, and seizures are symptoms for alcohol withdrawal; tremor and tachycardia are symptoms for hyperglycemia; and tachypnea, tachycardia, and coughing are symptoms for pulmonary embolism. The system checks for the combinations that fit the conditions that the clinician has selected, and generates an alert upon identifying any of these combinations. This technique provides effective early warning for the clinician, while reducing false alarms for events that are highly unlikely for a specific subject (e.g., hypoglycemia is unlikely for a subject who does not have diabetes, and pulmonary embolism is unlikely for a subject with no known risk for DVT).

It is recommended that most hospitalized subjects avoid staying in bed continuously for extended periods of times. In an embodiment of the present invention, system 10 measures how long the subject stays in bed continuously. The system logs the data and optionally generates an alert for a clinician if the length of time exceeds a threshold value, e.g., 12 hours, or a value set by the clinician.

In an embodiment of the present invention, sensor 30 is installed within a bed mattress as an integral part of the mattress.

Reference is again made to FIG. 2. In an embodiment of the present invention, system 10 monitors subjects in a hospital with a contactless mechanical sensor (sensor 30) and acoustic sensor 82. The system identifies audio signals that correlate with the motion signal as belonging to the subject. The system identifies snoring and wheezing, for example, and generates an alert for a clinician. For some applications, the system identifies talking by the subject by detecting a combination of vibration signal and audio signal. While the subject is talking, the system configures the heart rate and respiration rate detection algorithms so as not to mistake the talking-related body motion with respiration or heart rate data, e.g., by setting a blanking period during which data are not gathered.

A subject who is at risk of pressure ulcers is often placed on an alternating pressure mattress that is intended to vary the points on the subject's body that are in contact with the bed. In an embodiment of the present invention, each time the pressure mattress is activated to change position, system 10 detects the mechanical signal (i.e., the vibration) generated by the alternating pressure mattress and incorporates this vibration into the detection algorithm so as not to mistakenly identify this vibration as a respiration or heart rate signal. Alternatively, system 10 learns a characteristic vibration signature of the pressure mattress system, and pattern analysis module 16 identifies the signal each time it occurs in order to disregard it. Alternatively, when system 10 identifies the characteristic vibration of the alternating pressure mattress, it activates a blanking period during which data are not gathered.

In an embodiment of the present invention, system 10 calculates a confidence level for each clinical parameter detected. The confidence value is calculated, for example, for the respiration rate by calculating the signal-to-noise ratio in the frequency domain of the peak related to the respiration rate to the baseline noise level of the frequency spectrum. The system uses the confidence level to minimize false alarms. Thus, for example, if the respiration rate crosses a threshold set for an alarm, but the confidence level is not sufficiently high, the system may wait for an additional reading (e.g., 30 seconds later) before activating the alarm.

In an embodiment of the present invention, system 10 identifies change of posture of a subject using exactly one sensor, by identifying the change in the amplitude of the signal.

In an embodiment of the present invention, system 10 detects heart rate using high frequency components of the spectrum, using demodulation that uses a bank of band pass filters. For example, such a bank filter may include filters from 3 Hz up to 12 Hz, and each filter may be 1 Hz broad and have 0.5 Hz overlap with another filter. The algorithm selects the filter with the highest signal-to-noise ratio (SNR) of the heartbeat peak, and the system uses this filter until there is a change in subject's position, or until large body motion is detected. (In clinical trials carried out by the inventors, it was found that the optimal filter can change by 4-5 Hz for the same subject in different positions.) For some applications, the SNR of the heartbeat peak is defined as the magnitude of this peak divided by the spectrum amplitude in the vicinity of the peak not including any whole number harmonics of the peak. For example, if the frequency of the heart rate peak is f and the amplitude of the spectrum at frequency f is H(f), then:

$$SNR = \frac{H(f)}{1/2*(\text{mean}(H(f-0.5f:f-0.1f)+\text{mean}(H(f+0.1f:f+0.5f))} \quad \text{(Equation 8)}$$

where mean(H(a:b))=average value of H(f) where f is in the range a to b.

In an embodiment of the present invention, the system identifies the heart-beat-related signal by running a relatively high bandwidth band pass filter on the signal detected by a piezoelectric vibration sensor. The bandpass filter used has a passband of, for example, 30-80 Hz. The resulting signal is run through a peak detection algorithm in order to identify the locations of the actual heart beats.

In an embodiment of the present invention, system 10 calculates a clinical parameter as defined hereinabove, such as respiration rate and/or heart rate, and records the results. The system subsequently calculates a representative value for the clinical parameter over a specific period of time. Typically, the system calculates an average or median of the clinical parameter for the period of time, or calculates a series of representative values for the clinical parameter during smaller sub-periods of the period, and passes this series of values through a low pass filter or a median filter. The system generates an alert upon the onset of at least one of the following alert conditions (the system allows a clinician to set a level for each of the thresholds and timing ranges; alternatively, the system learns the parameter distribution for a specific subject, disease type, or hospital ward, and sets the levels accordingly):

The representative value of the clinical parameter for a time period of between about 10 seconds and about 3 minutes, for example, about 30 seconds, is greater than or less than a predefined threshold.

The representative value of the clinical parameter calculated for a time period T is above or below a set threshold. The time period T is a function of the threshold and the current reading, so that the further away the threshold is from the baseline reading of the subject or the population average, the shorter is the time period T. For example, if the average respiratory rate for the population is 12 breaths per minute and the high threshold is set to 20 breaths per minute, then time T is 2 minutes; but, if the threshold is set to 45 breaths per minute, then time T is automatically reduced to 15 seconds. Alternatively a continuous threshold vs. time T relationship is defined. For example, for the same example above, for each reading R (expressed in breaths per minute) which is greater than, for example 15, a threshold function T(R) in seconds is calculated using the following formula:

$$T(R)=540/(R-12)$$

If the value of the representative value of the respiratory rate calculated over time T(R) is greater than or equal to R, then an alarm is activated. A similar logic is applied in one embodiment, to other clinical parameters such as heart rate or activity level.

A sharp change occurs in the representative value of the clinical parameter for a time period of between about 10 seconds and about 3 minutes, for example, about 30 seconds. For example, a sharp change may be defined as at least a percentage change versus baseline of between about 20% and about 70%, for example, about 50%. The change is calculated versus the baseline, which is defined, for example, as the representative value for the clinical parameter for a certain amount of trailing time, e.g., the previous 15 minutes.

The clinical parameter shows a slow but substantial change. For example, the representative value of the clinical parameter measured in the most recent 10 minutes ($A_{10}$) may be compared to the representative value of the clinical parameter measured in the following time segments:

Last hour ($H_1$)
The hour before the last hour ($H_2$)
The hour before the two last hours ($H_3$)
The hour before the last three last hours ($H_4$)

A threshold is set between about 20% and about 70%, for example about 50%. The system generates an alarm if the following criterion is true:

$$\Delta_i = \text{ABS}[A_{10}-H_i]/A_{10}; \quad \text{(Equation 9)}$$

Alarm on=If [Max $\{\Delta_1, \Delta_2, \Delta_3, \Delta_4\}$>threshold (e.g., 50%)]

If a sudden loss in clinical parameter sensing is detected by the system without a change in weight (i.e., no bed exit has occurred), the system activates the alarm immediately, or, for example, within 1 minute.

The representative value of the clinical parameter during a most recent period of time, e.g., in the past 5 minutes, is different from the representative value for the clinical parameter during a substantially longer previous period of time, for example, the last 6 hours, by more than a certain number n (e.g., 2-10, such as 3) times the standard deviation of the clinical parameter within the substantially longer period of time. The range of n times the standard deviation around the representative value is defined as the accepted range for the clinical parameter.

In an embodiment of the present invention, system 10 is designed to prevent false alerts that may be generated by an additional person (e.g., a visitor or nurse) who is sitting on the bed in addition to the subject who is being monitored. In one embodiment, the system comprises a weight sensor that weighs the subject on the bed (as, for example, is installed in several beds manufactured by Stryker Medical of Kalamazoo, Mich. and Hill Rom of Batesville, Ind.). The reading from the weight sensor is communicated through standard communication means to control unit 14. System 10 has a set range of expected weights for the subject (e.g. between 30 and 250 Kg). Before the subject enters the bed, the weight measured is approximately 0. As long as the reading is below the 30 Kg level, the system does not generate any readings. When a weight within the above range is identified, the system automatically initiates measurement. If while measuring the subject a sudden increase in weight is identified of, for example, more than 30 Kg, system 10 recognizes that as an additional person on bed and stops measurement and/or alerts a clinician. This is used to prevent potentially false readings that may be caused due to more than one person being in bed. Alternatively, system 10 includes in one embodiment an operator interface to indicate to the system when the subject is in bed. The weight measured at that point is logged, and any time that a weight reading that is over 10% above the initial reading is identified, the system stops measurement and/or alerts a clinician.

In addition, in one embodiment, system 10 uses the weight reading from the weight sensor to identify situations of sudden loss of signal in contactless sensor 30. This loss of signal can be caused by the subject exiting the bed or by a cardiac arrest event. Utilizing the weight reading, system 10 can differentiate between those two scenarios. If the loss of signal is accompanied by a weight drop measured in bed, then the system identifies this as a patient exiting the bed. If such a change in weight is not identified, system 10 identifies this event as a cardiac arrest (for example), and alerts accordingly. In one embodiment, the bed includes a set of weight sensors that in a combined fashion can calculate the center of mass of the subject (as, for example, are sold by Stryker Medical of Kalamazoo, Mich.). In one embodiment, system 10 integrates the readings from these weight sensors with a contactless sensor in order to improve the accuracy of detection of a posture change of the subject. A posture change is identified only when the center of mass has shown some movement and the sensor 30 has identified additional features of a posture change as described above. In an embodiment, the detection of subject entry to and exit from bed, including the identification of an additional subject sitting or lying on the bed, can be identified with a camera coupled to an image processing unit. In one embodiment, an adaptation of the above described system is implemented for a subject in a chair or wheelchair.

When a clinician evaluates the condition of a patient, in some cases it is useful to combine the current reading of a parameter of the subject's condition with the trend of that parameter over the past few minutes, hours or days. The combination of the current reading and the trend enables an integrated assessment of the subject's current risk level and the need for immediate intervention. For example, a patient whose breathing rate is currently stable at 36 breaths per minute is in very different condition from a patient with the same current breathing rate who until an hour ago had a stable rate of 25 breaths per minute. In an embodiment of the present invention, system 10 identifies a slow change pattern and is configured with a threshold indicating when the system should generate an alert. The system calculates and outputs the amount of time until the subject will reach the alert threshold if the current slow trend continues. For example, if the system identifies a trend for an increase in breathing rate of 3 breaths/minute every hour, and the current breathing rate is 21 breaths/minute and the threshold is 36 breaths/minute, then the system calculates that the time to alert is 5 hours (5=(36−21)/3) and displays that value of time to alert on the screen. This alert enables the clinician to evaluate the risk level of the current condition based on both the current value and the slow trend. In addition, in an embodiment, the system outputs a warning if the time to alert is below a threshold value. For example, if the time to alert is less than 2 hours, the system may display a warning message on the screen.

In an embodiment of the present invention, system 10 combines two or more changes in clinical parameters. For example, the system may sum the percentage change in representative value of the heart rate and respiration rate over the last 10 minutes, and compare the sum to a threshold. The system generates an alarm upon finding that the sum is greater than a set threshold for the sum. This helps identify patient deteriorations while reducing false alerts that may be due to local artifacts in one specific reading (e.g. mistaken measurement of heart or respiration rate). In an embodiment, system 10 alerts when a change in one parameter occurs in the opposite direction of the normal correlation between the two parameters. For example, in most cases, heart and respiratory rates are highly correlated so that when for example the heart rate goes up, the respiratory rate tends to go up as well or at least stay approximately the same. Thus, in one embodiment, system 10 alerts when the heart rate increases by at least 20% and during the same time period the respiration rate decreases by at least 20%. This may be an indication of a deterioration associated with respiratory depression that may, for example, be caused by pain medication.

In an embodiment of the present invention, triggers for an alarm include events that combine heart and respiration deterioration. For example, the system generates an alarm upon finding that both (a) respiration rate values are greater than a threshold value continuously over a period of time, e.g., between about 10 seconds and about 3 minutes, and (b) the heart rate values are greater than a threshold value continuously during the period. For some applications, the system generates the alarm if both conditions (a) and (b) are true for a period of time that is between about 10 seconds and about 3 minutes, for example about 30 seconds.

In an embodiment of the present invention, system 10 identifies a high level of variability of the subject's heart rate as an indication of a possible risk of arrhythmia. For some applications, system 10 filters out measured heart rates that are highly variable when these measured heart rates correlate with a high or highly variable level of body movement, as measured with a motion sensor, because the variability of these measured heart rates may have been caused by a change in heart rate caused by the subject's body motion.

In an embodiment of the present invention, the system assigns each clinical parameter measurement (e.g., respiratory rate) a confidence level as a function, for example, of the following: signal quality, signal to noise ratio, repeatability of the results of the clinical parameter measurement within very short time windows, and/or repeatability of the results using different sensors or different calculation algorithms (e.g., one in the frequency domain and another in the time domain). The system typically continuously updates the confidence levels. The system generates an alarm only if the confidence level of the activating clinical parameter is greater than a threshold. Alternatively, the system generates the alarm if the average confidence level for the clinical parameter over a period of time, e.g., between about 10 seconds and about 3 minutes, is greater than a threshold level.

In an embodiment of the present invention, the system monitors a subject during time periods when he is awake and during time periods when he is asleep. The variation in clinical parameters is in some cases lower during sleep than during wake periods. In an embodiment, the system uses different thresholds for identification of subject deterioration for the two different states. The system switches between these two levels of thresholds either automatically or manually. For example, a healthcare worker or caregiver may manually switch between sleep mode and wake mode upon observing when the subject changes wake state, by entering the change in state into system 10 via user interface 24. Alternatively or additionally, the system may automatically switch according to the time of day when subject is expected to be asleep or awake, or based on detection by the system whether the subject is awake or asleep, such as by detecting when the patient exhibits a high level of non-respiratory body movements vs. low levels of non-respiratory body movements, as described hereinabove regarding techniques for identifying large body movement.

For example, a subject whose baseline breathing rate is 14 breaths/minute (br/min) may have alert activation thresholds set at 8 br/min and 30 br/min during wake period, but during sleep the range is narrowed to 8 br/min and 20 br/min, for more effective identification of deterioration. The use of the narrower threshold range during the wake state might create an unacceptable level of false alarms, but during sleep these tighter thresholds in some cases enable better identification of subject deterioration with few additional false alarms.

In an embodiment of the present invention, system 10 switches between different algorithms for calculating respiratory rates or heart rates between sleep and wake mode, and/or between low activity level and high activity level. For example, for some applications, it is more effective to use a time domain algorithm for calculating respiratory rate when the subject is awake and a frequency domain algorithm when the subject is asleep. Alternatively, the system switches between the different algorithms according to a level of subject activity and/or restlessness. For some applications, upon identifying that a subject is sleeping or in quiet rest, the system activates an early warning mechanism that generates an alert if these is a high risk that the subject will attempt to leave the bed. For example, if the subject is lying quietly in bed and the system suddenly identifies that the subject is moving around in bed continuously for over 30 seconds, the system may generate an alert a clinician that the subject is at high risk of trying to exit the bed. This is useful for preventing subject falls, especially for elderly, demented subjects. For some applications, system 10 builds a baseline of the subject's body movements during sleep and generates an alert upon detecting a movement pattern that is significantly different from baseline, which may indicate that the subject is having trouble sleeping or is transitioning out of sleep. For some applications, the system uses different criteria for generating alerts upon subject movement for different hours of the day. For example, between 2:00 AM and 5:00 AM, a relatively low level of motion in a 30 second interval creates an alert, while at other times of the day the threshold is greater. In one embodiment, system 10 enables a clinician to designate the subject as a high fall risk patient. For that patient, the system uses more stringent criteria to alert upon motion patterns that may indicate an oncoming fall. For example, the highest risk time period for patient falls for most institutions is the night period (e.g. between 8:00 PM and 5:00 AM). For a patient designated as high risk, the system identifies when the patient is entering rest mode (e.g. low patient motion for over 15 minutes and possibly also reduction of 5% in heart rate vs. the average in the previous 3 hours). Then, after such a rest status is determined, if there is an increase in motion which is above a threshold, an alert is activated to inform the nurse that the patient is not in resting mode any more. For example, if the system identifies large body movements for a period of over 30 seconds, an alert is activated. This may be an indication that the risk of falls has significantly increased and the nurse should attend to the patient as soon as possible. Activating such an alert only at night or only after patient rest is identified helps reduce alerts and accordingly alert fatigue for the clinical team. In one embodiment, the system is configured to alert upon bed exit of patients who are sedated post surgery for the first few hours while they gradually recover from the effects of sedation. The system has an operator interface that enables the clinician to indicate that a patient is post surgery and to indicate his expected recovery from sedation time. The system generates an alert if the patient attempts to leave bed during that recovery time, e.g. 12 hours, but then automatically turns off the alert feature in order to minimize false alarms. Alternatively, the system turns off the alerts when a motion level indicating full alertness is identified for a set period of time.

In some cases, movement of the subject reduces the accuracy of the detected parameters (e.g., respiratory rate and heart rate by a contactless sensor, and blood oxygen saturation and blood pressure by a contact sensor). In an embodiment of the present invention, system 10, when calculating the level of confidence given to the measurement, takes into account the level of the subject's motion (e.g., restlessness) during the time of measurement. In one embodiment, readings performed during a time period with large body motion are disregarded or given a lower weight in averaging over time. In another embodiment, if a value of a clinical parameter indicates that the system should generate an alarm, the system delays generating the alarm if the confidence level is lower. During this delay, the system continues to measure the clinical parameter and to evaluate whether to generate an alarm. If the value of the parameter throughout the delay, or on average during the delay, continues to indicate that an alarm is warranted, the system generates the alarm upon the conclusion of the delay. Thus, for example, assume that the system is configured to measure blood oxygen saturation, and to generate an alarm upon detecting that saturation drops below 90%. If the system identifies such a drop and does not detect any large body motion during the saturation measurement, the system generates an alert immediately. If, on the other hand, the system identifies such a drop and detects large body motion during the saturation measurement, the system continues to measure and average the saturation level during a delay, e.g., having a duration of 60 seconds, and generates an alarm only if the average over the full delay is below 90%. This technique generally reduces false alarms caused by motion artifacts.

In some cases, a change in a clinical parameter may be caused by large body motion of the subject. For example, a sudden increase in a subject's respiratory rate may be cause for alarm if the patient is lying still, but may be normal if the subject just exhibited restlessness in bed (this is particularly true for highly obese subjects). In an embodiment of the present invention, system 10 uses a tighter threshold or a quicker alert response time for changes in clinical parameters that do not occur immediately after or during a period of restlessness, and a second, looser, threshold for changes that occur immediately after or during a period of restlessness and that are to be expected to occur during restlessness (e.g., an increase in respiratory rate). For some applications, the system does not implement this double threshold if the restlessness occurs after the identification of the change in the clinical parameter.

In an embodiment of the present invention, upon identifying that a clinical parameter passes a threshold for generating an alert, the system delays generating the alert for a certain period of time. For example, the delay period may have a duration of between about 15 seconds and about 10 minutes, depending on clinician input, prior variability of the subject's readings, a confidence level of the measurement, and the subject's current condition (e.g. asleep, awake, REM sleep, known asthma condition, etc.). During this delay period the system further verifies that the reading was indeed accurate and/or is consistently beyond the alert threshold. Upon such verification, the system generates the alert. Otherwise the system does not generate the alert. This technique helps prevent false alerts.

In an embodiment of the present invention, system 10 identifies the onset and monitors the progression of sepsis according to changes in clinical parameters of a subject, for example, in heart rate and/or respiration rate of the subject. For some applications, the system identifies sepsis responsively to detection of an increase in a level of tremor, and/or heart rate and/or agitation level. For some applications, the system identifies sepsis responsively to detection of rapid shallow breaths, characterized by a decrease in the magnitude of the breathing-related motion together with an increase in the respiration rate. For some applications, the system calculates a sepsis score based on the combination of two or more of the following parameters: respiration rate, respiration depth (shallow vs. deep), heart rate, agitation/large body movement, and tremor. When the score changes significantly versus baseline or crosses a predefined threshold, the system generates an alert for a clinician.

In an embodiment of the present invention, system 10 identifies rapid shallow breaths by identifying an increase in respiration rate with a decrease in respiration motion signal size and without a change in subject's posture compared to before the onset of shallow breathing.

In an embodiment of the present invention, system 10 identifies rapid shallow breathing by identifying a decrease in magnitude of respiratory sinus arrhythmia of the subject.

In an embodiment of the present invention, system 10 notifies the nursing care staff of the any of the alarm conditions described herein using the existing nurse call system used in the healthcare facility.

In an embodiment of the present invention, system 10 persistently reminds nurses of a continued deterioration in the condition of a subject until intervention is successful.

In an embodiment of the present invention, system 10 identifies the entry of subject 12 into bed, such as using techniques described hereinabove. For some subjects, it is important that the subject not spend too much time in bed without exiting the bed (for example, in order to prevent pressure ulcers). System 10 alerts the medical staff if the subject has not left the bed for a predefined period of time, for example, 12 hours. For some applications, system 10 also identifies that a subject has changed position in bed or has been turned over, such as using techniques described hereinabove. Alternatively or additionally, the system identifies posture change using techniques described in U.S. patent application Ser. No. 11/552,872, which published as US Patent Application Publication 2007/0118054 to Pinhas et al., and which is assigned to the assignee of the present application and incorporated herein by reference. The system generates an alert if the subject has not changed position in bed or was not turned over for a predefined period of time. For some applications, system 10 comprises a user interface that enables the clinician to indicate to the system that the subject has been turned over in bed. This log enables historical analysis and creates a record that proper treatment has been provided to the subject. The system's automatic detection of subject motion is implemented either to confirm the clinician's entry or to replace it. For some applications, the system uses manual indication of subject turning over to calibrate the automatic posture change detection algorithm.

In an embodiment of the present invention, system 10 helps medical establishments enforce and log the compliance with a pressure ulcer prevention protocol. For example, in many hospitals, the protocol for preventing pressure ulcers in patients who are considered at high risk for such ulcers is to have the patients turned over once every 2 hours. In an embodiment, system 10 comprises a user interface that enables a clinician (e.g. physician or head nurse) to indicate the required protocol to prevent pressure ulcers, e.g., the maximal amount of time allowed between patient's posture change or patient being turned. The system's user interface 24 then displays a counter counting down the time till the next required posture change of the patient, according to the protocol. If that counter reaches zero an alarm is activated. If the system identifies a posture change, the counter is reset to the original value (e.g. 2 hours) and initiates the countdown again.

In an embodiment, system 10 includes a double layer of protection to prevent a false detection of a patient being turned. In order to make the identification of a posture change and to reset the counter, it requires both a posture change to be detected via the sensor and control unit and the clinician to make an input via the user interface that he/she actually turned the patient. So, in order to reset the counter, system 10 requires the clinician input and sensor input regarding posture change to coincide within a set period of time (e.g., 10 to 300 seconds, typically 60 seconds. Thus, when the nurse approaches the pressure ulcer risk patient to turn him, she presses the appropriate button on the user interface and then turns the patient. The system identifies the turn through its sensor and accepts the input through the user interface; if they both coincide within (for example) 60 seconds, then the counter is reset. In one embodiment, the system also logs every such event to help document patient care and reduce hospital liability. In one embodiment, the detection of posture change is implemented without contacting the subject's body, via a sensor under the mattress or a camera.

In an embodiment, system 10 combines two sensing elements: a camera and a mechanical sensor. The signal from the two sensors is correlated in order to reduce artifacts. For each sensor, a confidence value is calculated for each reading, and the source with the higher confidence level is selected. Alternatively, a clinical parameter (e.g. heart rate) is calculated independently from the signal of each sensor. If the two readings are similar within a set range, the readings are allowed, displayed, and logged. If relevant, alerts are created. If the signals are different, they are rejected.

In an embodiment of the present invention, system 10 calculates a score based on the level of motion and number of subject posture changes. The system analyzes this score over a time period ranging from about 15 minutes to about 3 days, for example about 4 hours. This score serves as an indication of the level of risk of development of a pressure ulcer. This score index may be adapted according to the guidelines set by relevant regulatory bodies or by an attending physician. For example, most hospitals have a policy that requires subjects who are at risk of developing pressure ulcers to be turned over or repositioned at least once every two hours.

In accordance with a first exemplary technique for calculating this score, the system uses the following equation:

$$\text{Score}=100-20*(TC/RTC) \quad \text{(Equation 10)}$$

wherein TC is the time from last posture change measured in minutes, and RTC is the recommended time in minutes between posture changes according to guidelines or physician order.

For some applications, the calculated score is displayed numerically and graphically, e.g., color-coded. For example, the score is shown as green if it is greater than 85. A score of 75-85 is shown as yellow, and a score below 75 is shown as red. For some applications, if the score falls below a threshold, the system generates an alarm in order to alert a clinician and enable timely intervention.

In accordance with a second exemplary technique for calculating this score, the system uses the following equation:

$$\text{Score}=[100-20*(TC/RTC)]+MPR \quad \text{(Equation 11)}$$

wherein TC is time from last posture change measured in minutes, RTC is recommended time in minutes between posture changes according to guidelines or physician order, and MPR is the percentage of time during the last hour in which the subject made large body movements (e.g., each 15 second interval is marked as movement if a large body movement is identified in the interval, and the percentage of such marked intervals during the last hour is used in Equation 11).

In an embodiment of the present invention, the system calculates an average score over a time period ranging from about one hour to the duration of the subject's stay in the hospital. The average score serves as an indication of the compliance (i.e., a compliance index) of the clinical team with the designated guideline. The average score can be used by the hospital administration in order to evaluate team performance and enable continuous improvement of subject care and subject experience. In one embodiment, a moving (for example) 8-hour window is used for averaging the score. The system reports the lowest score in any 6-hour window during which the patient was in the hospital.

In an embodiment of the present invention, this score also reflects changes in respiration rate, heart rate, and/or level of tremor compared to baseline. An increase in these parameters may indicate an infection that in some cases accompanies the onset of pressure ulcers. For some applications, the score alternatively or additionally reflects a level of variability in the heart rate and respiration rate as additional indicators of infection.

In an embodiment of the present invention, system 10 (comprising any suitable sensor described herein) is used to identify when a subject is in bed. Periodically, e.g., every hour, the system logs whether or not there is a subject in the bed. For example, this logging may enable hospital equipment rental providers to charge hospitals for rental beds only for the days or hours when a subject uses the bed.

Clustering:

In calculating respiratory rate utilizing raw sensor data there are often several challenges. One of the challenges is how to overcome local motion artifacts and utilize historic data in order to minimize false readings while still maintaining responsiveness to changes in respiration rate. Previous algorithms have focused on different types of filtering with varying level of success. The clustering model described below, in accordance with an embodiment of the present invention, provides an effective method to integrate current and historic data plus an effective method to integrate not just historic time-related information, but also respiration-shape-related information and information related to changes in shape over time, and combines all of this information to reduce provide false readings. In one embodiment, system 10 includes a respiration rate algorithm that is based on a fuzzy c-means logic algorithm. The clustering based algorithm is implemented in 4 steps:

Global max detection of potential respiration cycles
Outlier removal
Fuzzy C-mean clustering
Decision block Global Max Detection Algorithm Global max detection of potential respiration cycles is performed by a global max algorithm. This algorithm distinguishes local max/min from global max/min, based on the respiration signal's amplitude and periodicity. The output of this algorithm is the list of potential respiration cycles over a fixed period of time, called respiration history (for example 2 minutes), and a D-dimensional vector of the cycle parameters for each respiration cycle. In one embodiment, the cycle parameters used are: respiration cycle time duration and peak-to-peak amplitude (so D=2). In another embodiment, the shape features of the respiration cycle are used, namely, the slope of the sensor signal in the rising portion of the respiration cycle, the rise time of the sensor signal in the rising portion of the respiration cycle, the slope of the sensor signal in the falling portion of the respiration cycle, and the sensor signal fall time in the falling portion of the respiration cycle (D=6).

In another embodiment, the length of the respiration history is adaptive, depending on the detected respiration rate.

Outlier Removal

In one embodiment, respiration cycles with parameters distant from all other potential respiration cycles (outliers) are removed from the respiration history.

This may be done using the following steps:

A spatial grid in the D-dimensional space of respiration cycle parameters is created. Each cycle in the respiration history belongs to a specific grid cell. The discrete spatial density of the respiration cycles is determined as the number of cycles in each cell. All cells with a density lower than a density threshold are considered as outliers and corresponding cycles are removed from the respiration history.

Fuzzy C-Mean Clustering

In an embodiment, fuzzy c-means clustering is applied to the respiration history. Fuzzy c-means clustering is described by J. C. Bezdek in: "Pattern Recognition with Fuzzy Objective Function Algorithms", Plenum Press, New York (1981), which is incorporated herein by reference. The clustering process is repeated for configurations of 4 clusters, 3 clusters, 2 clusters and 1 cluster.

For each cluster, a relative indicator is calculated as stated in equation 12 below. The best cluster is determined as the cluster with the minimum indicator value. In one embodiment, the new respiration rate is determined according to the time duration coordinate of the best cluster center. In another embodiment, the new respiration rate is determined according to the latest cycle detected in the best cluster.

In another embodiment, the new respiration rate is determined according to the mean duration of the respiration cycles belonging to the best cluster and detected over the last T sec (for example T=60 sec).

For the best cluster, a confidence value is calculated as stated in equation 13 below. If the confidence is bigger than the selected threshold, the cluster is rejected and the new respiration rate is determined in the decision block. If the confidence is below the threshold, then its value and the new respiration rate are sent to the decision block.

Decision Block

In one embodiment, the decision block decides whether the new respiration rate received from the clustering block should be displayed on the display of system 10. The decision is based on the general phenomenon that an accurate respiration value is more likely to be close to the previous ones. To do this, a probability density function (PDF) of the previously accepted respiration rate values is calculated, and the probability of the new respiration rate is extracted from this PDF. Finally, according to a combination of the probability and confidence values, the decision block decides whether to reject or display the latest value.

$$D_k = \frac{\sum_{items\_in\_cluster\_k} \|x - \bar{x}_k\|^2}{N_k} \cdot conf3_k \quad \text{(Equation 12)}$$

$$conf3_k = 1 - \min\left[0.9, \frac{\sum_{items\_in\_cluster\_k} cycle\_duration}{2(History\_Lenght)}\right]$$

where:
x is the vector of the normalized parameters
$N_k$ is the number of cycles in cluster k $$Conf = \frac{\sum_{items\_in\_best\_cluster} \left( \sum_{d=1}^{D} (X_d / \overline{X}_d) - 1 \right)^2}{N_{best\_cluster}} \cdot conf3 \quad \text{(Equation 13)}$$

$X_d$ is the parameter value of dimension d
$N_{best\_cluster}$ is the number of cycles in the best cluster In one embodiment, system 10 evaluates the quality of rest the subject has had during a period of time (e.g. at night) and calculates a score. This score is presented to a clinician to help make a decision regarding the management of the patient's therapy (e.g. medication or discharge from the hospital). For example score S can be calculated as follows:

$$S = R + HR + RR + K*BEX \quad \text{(Equation 14)}$$

wherein:
S—clinical score
R—level of patient restlessness during the time period, the higher the score the higher the restlessness
RR—the change in the average respiratory rate of the subject in the current time period vs. a previous time period (e.g. the previous 6 hours), i.e. if the average respiratory rate during the current time period is 12% higher than in the previous 6 hour period, this parameter get the value of 12.
HR—the change in the average heart rate of the subject in the current time period vs. a previous time period (e.g. the previous 6 hours), i.e. if the average heart rate during the current time period is 12% lower than in the previous 6 hour period, this parameter get the value of −12.
BEX—number of bed entry/exit cycles during the time period
K—constant that serves as coefficient for bed exit in the score, typically between 3 and 20, for example 8.

The lower the score S, the more restful the time period was and so is indicated to the clinician. For example, several clinicians believe that for many patients in hospitals, if they have had a restful night, in many cases they can be discharged home immediately.

Apnea Detection

In one embodiment, system 10 is used to identify apnea events. Apnea detection is performed in two stages. The first stage is the preliminary identification of suspicious intervals. In the second stage, a vector of scores is calculated for each interval—the score is correlated with the estimated likelihood of the apnea event. A decision block then analyzes the scores, and provides the detection of the apnea events. This is especially useful for identifying subjects who are at high risk for having moderate or severe apnea.

Detection of suspicious intervals:

In the first stage, for detection of suspicious intervals, two methods are utilized:—correlation and movement detection.

i. Correlation.

For each subject, a matched filter is selected which consists of the sensor signal shape measured during three sequential regular breath cycles previously detected for that subject. The correlation result of this matched filter with the overall signal recorded for the patient is calculated by shifting of the match filter window over the entire recording.

The intervals with the lowest correlation response are defined as suspected apnea intervals. The detection of these intervals is performed using two parameters:

(1) Substantial drop in the amplitude of the correlation signal compared to the running average of the correlation signal over the previous time period. For example, a correlation level that is 60% lower than the running average of the correlation signal for the previous 90 seconds.
(2) Substantial narrowing in the distance between correlation peaks. When a cross correlation between the matched filter and the respiration related motion signal is performed, the result is expected to show a series of peaks spaced according to the respiratory time period, i.e. if the respiratory rate is 12 breaths/minute, the peaks will be spaced approximately 5 seconds from each other. Substantial narrowing is defined as a distance less than 70% of the distance between peaks based on the running average respiratory rate. Thus, for a respiratory rate of 12 breaths/minute, this criterion is met if the peaks have a distance below 70% of that i.e. 3.5 seconds.

Intervals that meet both conditions are identified as apnea suspicious intervals. The output is a vector of the time stamps of the beginning of each suspicious interval.

ii. Movement Detection:

In one embodiment, this algorithm utilizes algorithms designed for identification of large body movements as described herein or, for example, in previous patent applications by the same assignee, cited herein. The large body movement algorithm provides an indication for which time slots within the sensor detected signal are characterized by large body movement. In one embodiment, the apnea detection algorithm further implements methods for recognition of the complete large body movement time period, as follows: an algorithm is used to unite relevant fragments of body movement periods into whole movement periods even if the identified movement slots are separated by short segments where large movement is not detected.

The input of this algorithm is the indication of time slots of large body movement fragments, and the output is start and end points of large body movement time periods.

Suspected interval from both methods described above are combined into a single list of suspected apnea events.

The next step is that each suspicious interval is evaluated again, where for each interval the three minutes surrounding the event are taken and analyzed as the "current interval." For each such interval, the algorithm determines whether or not an apnea event occurred and calculates a confidence level for that decision. The decision for each current interval is based on the following criteria:

Change in Heart Rate.

A rise in heart rate that reflects a short arousal that terminates the apnea event is known as a characteristic of apnea. The duration of this rise is often about 5-8 heart beats. This rise is detected by analyzing the heart rate signal beat to beat distances, for example as identified between peaks in the photoplethysmography signal derived from a pulse oximeter sensor integrated into system 10. Each two adjacent peaks represent the R-R interval, meaning two peaks straddle one heart beat. A rise in heart rate is defined versus the mean and taking into account the standard deviation of the heart rate along the night. For example, heart rate increase is determined as a potential apnea pattern if the heart rate is more than 20% higher than the average of the heart rate over the duration of the night, and more than 12% higher than the average+ standard deviation for duration of the night.

The highest confidence score will be given to areas which meet both the 20% and 12% requirements.

Change in Saturation Level:

In one embodiment, a Pulse-Oximeter oxygen saturation level signal is used as well. Using this signal it is possible to identify the de-saturation following apnea events. De-saturation is identified as an apnea pattern if a decrease of at least 5% from the maximal value in the current interval is identified.

Change in Respiration Rate.

In one embodiment, a change of the respiration rate before and after the suspected apnea event is utilized to identify an apnea event. The change in respiration rate (RR) is detected by calculating the Power Spectrum Density (PSD) of the signal in the current interval. If the RR is constant for the duration of the time interval, then there is a single significant peak in the PSD corresponding to the constant RR. However, if the RR changes after the suspected apnea event versus before the event, the PSD will show two peaks in the range of potential respiratory rates.

Apnea occurs usually along with a movement. If a suspicious interval contains movement, the PSD is significantly distorted and the detection of the two peaks is more difficult. Because of this, in an embodiment, the movement intervals are removed from the current interval and the remaining sections of the interval are concatenated. In one embodiment, this is implemented in the following way:

Suspicious intervals sensor signal segments are analyzed by sliding a 60 second window with 10 seconds of data overlapping adjacent windows.

Each 60 second window is processed in three stages.
(1) The movement (large body movement) (if there is any) is removed in order to get a 'clean signal'.
(2) Low Pass FIR Filter is applied on the 'clean signal'. A cutoff frequency of 1-2 Hz (e.g., 1.2 Hz) can be used for the low pass FIR filter.
(3) A Welch algorithm for calculating PSD is utilized and applied to the filtered 'clean signal'.

The change of the RR is detected if at least one of the resulting PSD diagrams contains two peaks.

The Score Formula.

In one embodiment, the results that are calculated for the current interval using each of the above methods (i.e., detection of change in Heart Rate, Change in Saturation Rate, and Change in Respiration Rate) are combined utilizing a scoring formula. For example, for each of the above criteria, a score for matching that criteron is calculated as a confidence level between 0 and 100 for each such current interval, where a score of 100 is given to the result for each criterion measured in the most severe apnea events, and 0 is the score given when there is absolutely no change. For example, for change in Heart Rate, a score of 100 is given for any change above 40 bpm. For change in Saturation, a score of 100 is given for a change over 20%, and for Respiration Rate, a score of 100 is give for change of over 10 breaths/minute. For any result below these thresholds, a linear interpolation is utilized to calculate the score. Thus, for example, for a change in heart rate of 10 bpm, a score of 25 is given. Then, the overall confidence level score is the average of the three confidence numbers for the three criteria.

Decision Block

The purpose of this module is to arrive at a final decision whether the current interval contains an apnea event. For example, the score is compared to a threshold value.

In one embodiment, system 10 identifies patients with a high risk for apnea by analyzing the variation of heart rate during sleep. A patient with sleep apnea is expected in many cases to have a cyclical heart rate pattern during sleep. This pattern is expected to have a period in the range of 40-120 seconds. In one embodiment, system 10 analyzes the periodicity of the heart rate signal at night, and if an appropriate cyclical pattern is found, an indication is given to the clinician that the patient is at high risk of sleep apnea.

Figure 18:
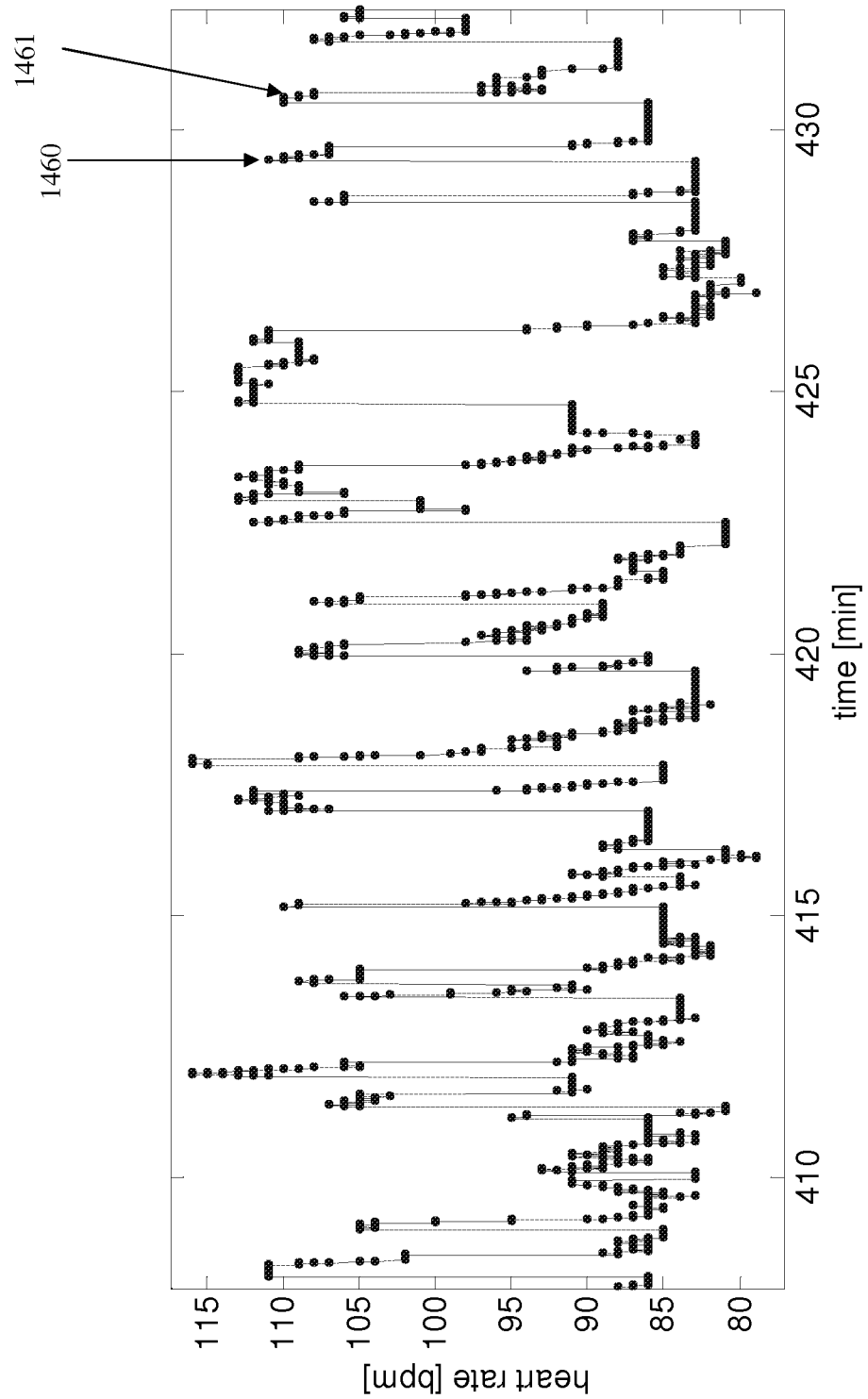
FIG. 18 is a schematic illustration of an exemplary heart rate signal output, measured on a subject during sleep where the subject is suspected of having sleep apnea, in accordance with an embodiment of the present invention.

FIG. 18 shows a heart rate pattern measured with an embodiment of the present invention utilizing a contactless sensor that shows a patient identified by the system as having a high risk of sleep apnea. Peaks 1460 and 1461 are sample peaks in the heart rate pattern that are about 60 seconds apart.

Figure 19:
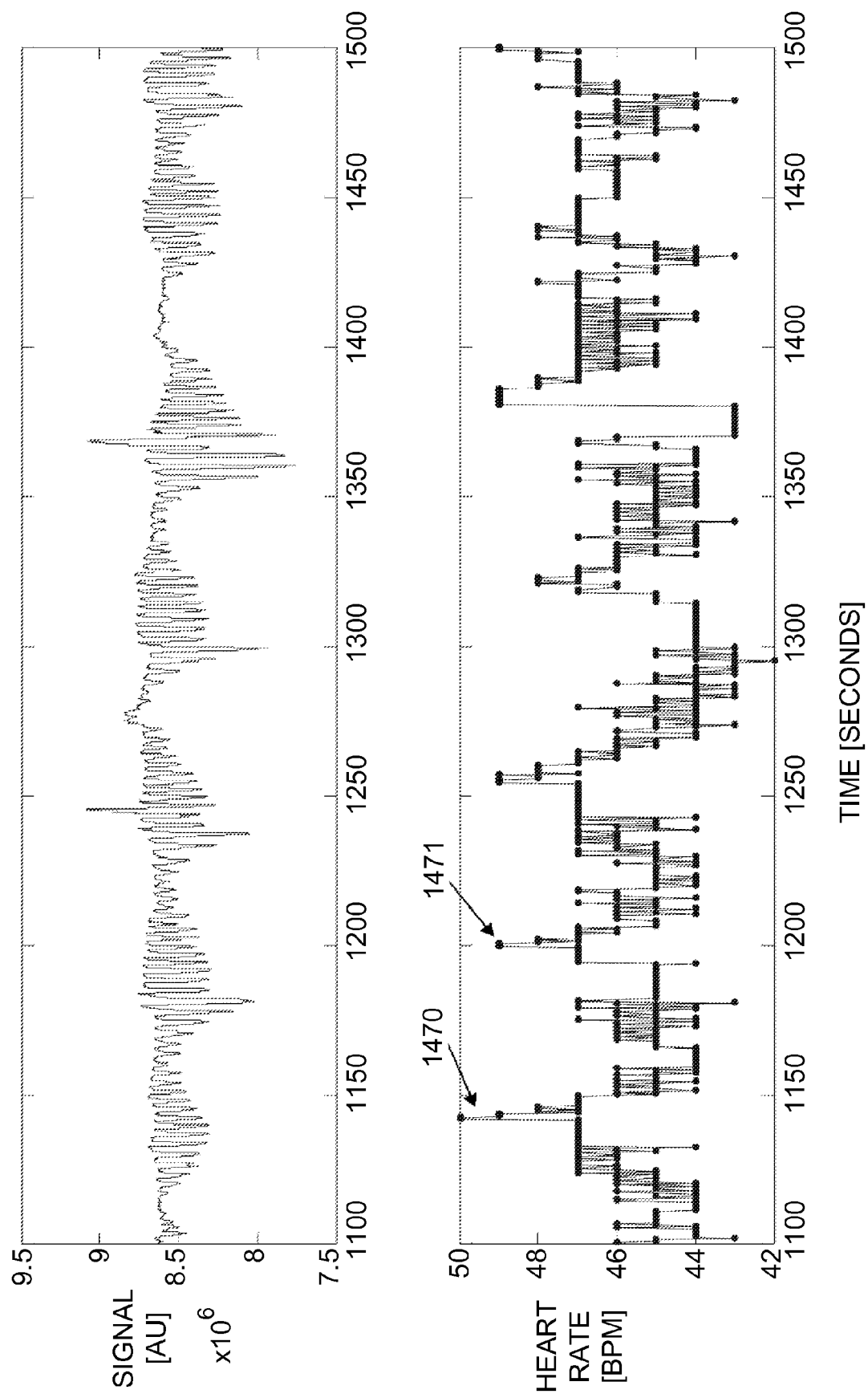
FIG. 19 is a schematic illustration of the motion signal (upper panel) and the corresponding detected heart rate (lower panel) in accordance with an embodiment of the present invention measured on a subject.

FIG. 19 shows a similar cyclic heart rate pattern (lower panel) that corresponds to a cyclic breathing pattern (upper panel—respiration amplitude increasing and decreasing once every 60 seconds) that reflects an apnea event, in this case most likely central apnea with a cycle time of approximately 60 seconds. This repeating cyclical heart rate pattern is identified by system 10 and presented to a clinician as indicating potentially high risk of apnea. In one embodiment, system 10 correlates between the peaks in heart rate and changes in respiratory pattern as shown in the upper panel of FIG. 19, or with evidence of large body motions as measured by a motion sensor. In this example, the subject has low heart rate and low variability in comparison to the example in FIG. 18. Heart rate increases as respiratory amplitude decreases (due to apnea).

If the evidence of large body motion and/or the respiratory motion pattern change correlate with a significant subset of the heart rate peaks, the level of risk of apnea determined is increased and accordingly displayed to the clinician.

Figure 20A:
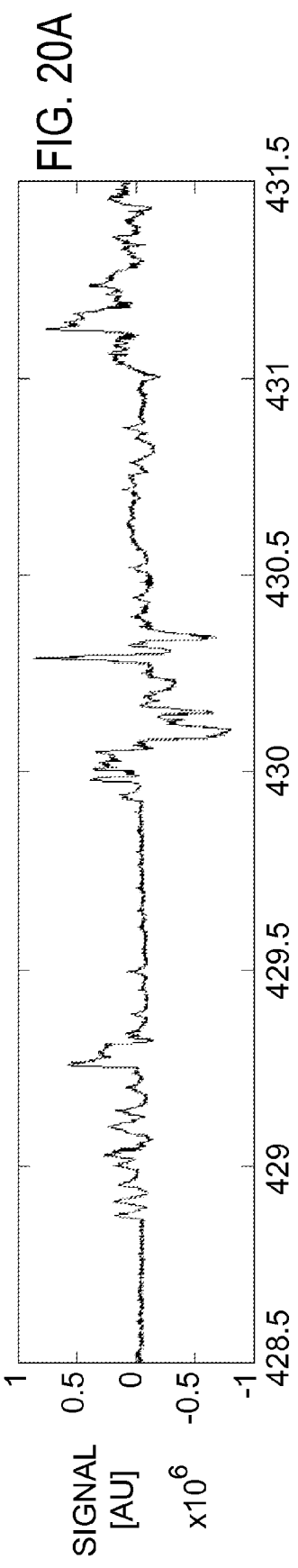
FIGS. 20A-C are schematic illustrations of the motion signal (20A), the corresponding detected heart rate (20B), and the large body motion detected output (20C), measured in accordance with an embodiment of the present invention measured on a subject.
Figure 20B:
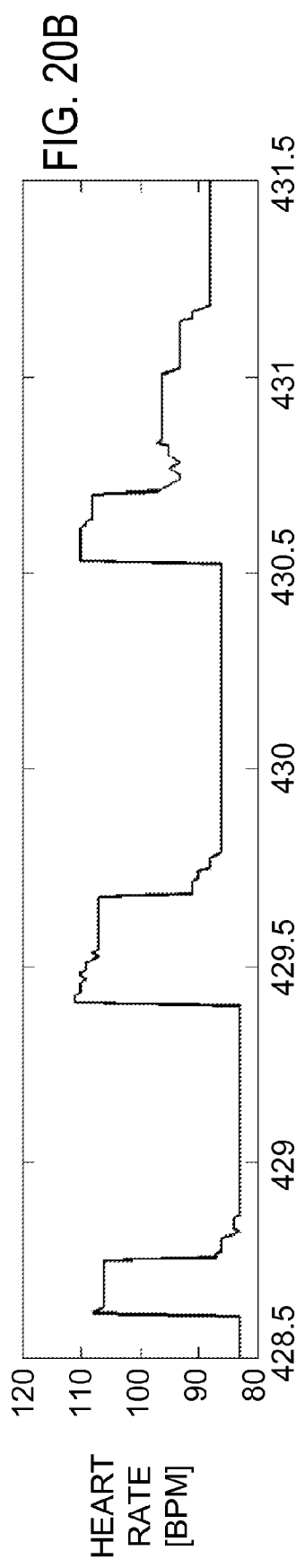
Figure 20C:
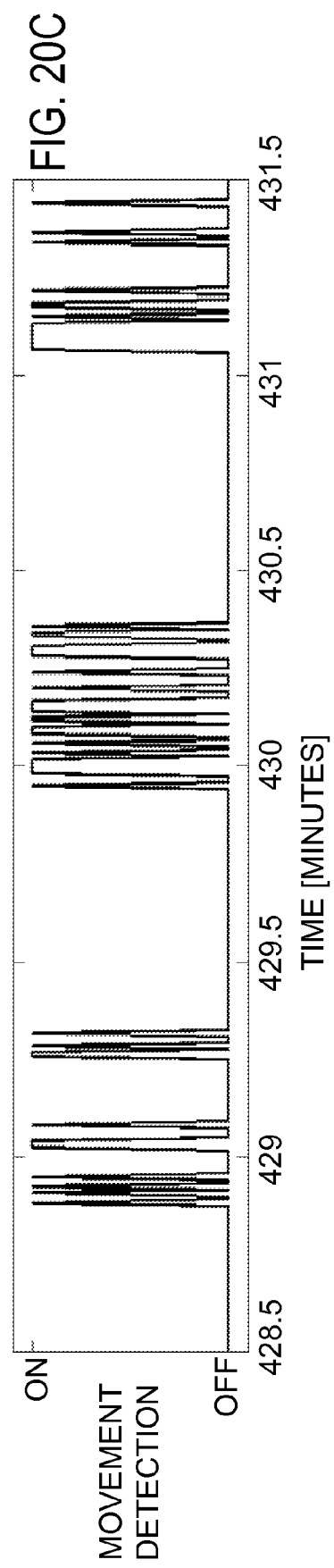

FIGS. 20A-C show the general motion signal (20A), heart rate output signal (20B) and large body motion detection output signal (20C) for a subject with a high risk of sleep apnea. Large body motion detection is indicated with an output of "On", while no large body motion is indicated with an output of "Off". The large body motion detection correlates well with the periodicity of the heart rate pattern— showing a brief series of motions that repeats itself for each cycle of the heart rate increase (approximately every 50 seconds), thus strengthening the case for a high apnea risk. In one embodiment, system 10 calculates an apnea risk index based on one or more of: existence of a heart rate cyclical pattern with a period of 40-120 seconds, correlation of heart rate pattern with respiratory cyclical pattern, correlation of heart rate cyclical pattern with large body motion detection, and correlation of oxygen saturation reduction (as measured with, for example, a finger mounted pulse-oximeter with the heart rate cyclical pattern. For example, for each detected peak of the cycle of the heart rate, a time window of length corresponding to the periodicity of the heart rate is opened for the section preceding that peak. Thus, for example, if the heart rate's cyclical pattern has a period of 50 seconds, a window of length 50 seconds is analyzed each time. If within that period a large body motion is detected, a respiratory pattern with a distinct change in the amplitude of breaths (a standard deviation of the respiratory signal amplitude that is over a threshold set between 15% and 30% of the average cycle amplitude, e.g. 20%), or a DMRC is identified within that time window, then this event is counted as an apnea risk event. If the number of such events per hour is above a threshold (for example, a threshold that is between 10 and 30, for example, 15), then a clinician is alerted that the patient is at risk for having apnea with a risk index which is the number of such events per hour.

Techniques described herein may be practiced in combination with techniques described in one or more of the following applications and patents, which are incorporated herein by reference. In an embodiment, techniques and apparatus described in one or more of the following applications are combined with techniques and apparatus described herein:

U.S. Provisional Patent Application 61/052,395;
U.S. Provisional Patent Application 61/054,754;
U.S. Provisional Patent Application 60/674,382;
U.S. Provisional Patent Application 60/692,105;
U.S. Provisional Patent Application 60/731,934;
U.S. Provisional Patent Application 60/784,799;
U.S. Provisional Patent Application 60/843,672;
U.S. Provisional Patent Application 60/924,459, filed May 16, 2007;
U.S. Provisional Patent Application 60/924,181, filed May 2, 2007;
U.S. Provisional Patent Application 60/935,194, filed Jul. 31, 2007;
U.S. Provisional Patent Application 60/981,525, filed Oct. 22, 2007;
U.S. Provisional Patent Application 60/983,945, filed Oct. 31, 2007;
U.S. Provisional Patent Application 60/989,942, filed Nov. 25, 2007;
U.S. Provisional Patent Application 61/028,551, filed Feb. 14, 2008;
U.S. Provisional Patent Application 61/034,165, filed Mar. 6, 2008;
U.S. Provisional Application 61/082,510, filed Jul. 22, 2008;
U.S. patent application Ser. No. 11/197,786, filed Aug. 3, 2005, which issued as U.S. Pat. No. 7,314,451;
U.S. patent application Ser. No. 11/782,750;
U.S. patent application Ser. No. 11/446,281;
U.S. patent application Ser. No. 11/755,066;
U.S. patent application Ser. No. 12/113,680;
U.S. patent application Ser. No. 11/048,100, filed Jan. 31, 2005, which issued as U.S. Pat. No. 7,077,810;
International Patent Application PCT/IL2005/000113, which published as WO 2005/074361;
International Patent Application PCT/IL2006/000727, which published as WO 2006/137067; and
International Patent Application PCT/IL2006/002998, which published as WO 2007/052108.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a subject who is undergoing respiration, the apparatus comprising:
a motion sensor configured to sense motion of a subject;
a control unit comprising:
a breathing pattern analysis unit that is configured to analyze components of the sensed motion that result from the subject's respiration, the breathing pattern analysis unit comprising:
double-movement-respiration-cycle-pattern-identification functionality that is configured to designate respiration cycles as being double-movement-respiration-cycles by determining that the cycles define two subcycles; and
double-movement-respiration-cycle-event-identification functionality configured to identify a double-movement-respiration-cycle event by detecting that the subject has undergone a plurality of double-movement-respiration-cycles; and
output-generation functionality configured to generate an output that is indicative of the subject having used accessory muscles in breathing, in response to identification of the double-movement-respiration-cycle event; and
a user interface configured to display the output,
wherein the double-movement-respiration-cycle-pattern-identification functionality is configured to distinguish between a first cycle that defines two subcycles, and a second cycle that does not define two subcycles, even if the first and second cycles have substantially similar amplitudes to one another.

2. The apparatus according to claim 1, wherein the sensor is configured to sense motion of the subject without contacting the subject or clothes the subject is wearing.

3. The apparatus according to claim 1, wherein the sensor is configured to sense motion of the subject without contacting or viewing the subject or clothes the subject is wearing.

4. The apparatus according to claim 1, wherein the double-movement-respiration-cycle-pattern-identification functionality is configured to determine that a cycle defines two subcycles at least partially in response to a slope of a respiration motion signal of the subject.

5. The apparatus according to claim 1, wherein the control unit is configured to predict an onset of a clinical condition of the subject in response to the double-movement-respiration-cycle-event-identification functionality identifying the double-movement-respiration-cycle event.

6. The apparatus according to claim 5, wherein the control unit is configured to predict the onset of the clinical condition by predicting the onset of a clinical condition selected from the group consisting of: elevated heart rate and elevated respiration rate.

7. The apparatus according to claim 5, wherein the control unit is configured to predict the onset of the clinical condition at least 30 minutes before the onset of the clinical condition.

8. Apparatus for use with a subject who is undergoing respiration, the apparatus comprising:
a motion sensor configured to sense motion of a subject;
a control unit comprising:
a breathing pattern analysis unit that is configured to analyze components of the sensed motion that result from the subject's respiration, the breathing pattern analysis unit comprising:
double-movement-respiration-cycle-pattern-identification functionality that is configured to designate respiration cycles as being double-movement-respiration-cycles by determining that the cycles define two subcycles; and
double-movement-respiration-cycle-event-identification functionality configured to identify a double-movement-respiration-cycle event by detecting that the subject has undergone a plurality of double-movement-respiration-cycles; and
output-generation functionality configured to generate an output that is indicative of the subject having used accessory muscles in breathing, in response to identification of the double-movement-respiration-cycle event; and
a user interface configured to display the output,
wherein the double-movement-respiration-cycle-pattern-identification functionality is configured to distinguish between a first cycle that defines two subcycles, and a second cycle that does not define two subcycles, even if the first and second cycles have substantially similar frequencies to one another.

9. The apparatus according to claim 8, wherein the control unit is configured to predict an onset of a clinical condition of the subject in response to the double-movement-respiration-cycle-event-identification functionality identifying the double-movement-respiration-cycle event.

10. Apparatus for use with a subject who is undergoing respiration, the apparatus comprising:
  a motion sensor configured to sense motion of a subject;
  a control unit comprising:
    a breathing pattern analysis unit that is configured to analyze components of the sensed motion that result from the subject's respiration, the breathing pattern analysis unit comprising:
      double-movement-respiration-cycle-pattern-identification functionality that is configured to designate respiration cycles as being double-movement-respiration-cycles by determining that the cycles define two subcycles; and
      double-movement-respiration-cycle-event-identification functionality configured to identify a double-movement-respiration-cycle event by detecting that the subject has undergone a plurality of double-movement-respiration-cycles; and
    output-generation functionality configured to generate an output that is indicative of the subject having used accessory muscles in breathing, in response to identification of the double-movement-respiration-cycle event; and
  a user interface configured to display the output,
  wherein the double-movement-respiration-cycle-pattern-identification functionality is configured to determine that a cycle defines two subcycles at least partially in response to an amplitude of the cycle.

11. The apparatus according to claim 10, wherein the control unit is configured to predict an onset of a clinical condition of the subject in response to the double-movement-respiration-cycle-event-identification functionality identifying the double-movement-respiration-cycle event.

12. Apparatus for use with a subject who is undergoing respiration, the apparatus comprising:
  a motion sensor configured to sense motion of a subject;
  a control unit comprising:
    a breathing pattern analysis unit that is configured to analyze components of the sensed motion that result from the subject's respiration, the breathing pattern analysis unit comprising:
      double-movement-respiration-cycle-pattern-identification functionality that is configured to designate respiration cycles as being double-movement-respiration-cycles by determining that the cycles define two subcycles; and
      double-movement-respiration-cycle-event-identification functionality configured to identify a double-movement-respiration-cycle event by detecting that the subject has undergone a plurality of double-movement-respiration-cycles; and
    output-generation functionality configured to generate an output that is indicative of the subject having used accessory muscles in breathing, in response to identification of the double-movement-respiration-cycle event; and
  a user interface configured to display the output,
  wherein the double-movement-respiration-cycle-pattern-identification functionality is configured to determine that a cycle defines two subcycles at least partially in response to a frequency of the cycle.

13. The apparatus according to claim 12, wherein the control unit is configured to predict an onset of a clinical condition of the subject in response to the double-movement-respiration-cycle-event-identification functionality identifying the double-movement-respiration-cycle event.

14. Apparatus for use with a subject who is undergoing respiration, the apparatus comprising:
  a motion sensor configured to sense motion of a subject;
  a control unit comprising:
    a breathing pattern analysis unit that is configured to analyze components of the sensed motion that result from the subject's respiration, the breathing pattern analysis unit comprising:
      double-movement-respiration-cycle-pattern-identification functionality that is configured to designate respiration cycles as being double-movement-respiration-cycles by determining that the cycles define two subcycles; and
      double-movement-respiration-cycle-event-identification functionality configured to identify a double-movement-respiration-cycle event by detecting that the subject has undergone a plurality of double-movement-respiration-cycles; and
    output-generation functionality configured to generate an output that is indicative of the subject having used accessory muscles in breathing, in response to identification of the double-movement-respiration-cycle event; and
  a user interface configured to display the output,
  wherein the double-movement-respiration-cycle-pattern-identification functionality is configured to determine that a cycle defines two subcycles by identifying two adjacent peak and trough sets of a respiration motion signal of the subject, the sets being substantially asymmetrical with respect to one another, and, in response thereto, designating the adjacent peak and trough sets as being two subcycles of a single respiration cycle.

15. The apparatus according to claim 14, wherein the control unit is configured to predict an onset of a clinical condition of the subject in response to the double-movement-respiration-cycle-event-identification functionality identifying the double-movement-respiration-cycle event.

16. Apparatus for use with a subject who is undergoing respiration, the apparatus comprising:
  a motion sensor configured to sense motion of a subject;
  a control unit comprising:
    a breathing pattern analysis unit that is configured to analyze components of the sensed motion that result from the subject's respiration, the breathing pattern analysis unit comprising:
      double-movement-respiration-cycle-pattern-identification functionality that is configured to designate respiration cycles as being double-movement-respiration-cycles by determining that the cycles define two subcycles; and
      double-movement-respiration-cycle-event-identification) functionality configured to identify a double-movement-respiration-cycle event by detecting that the subject has undergone a plurality of double-movement-respiration-cycles; and
    output-generation functionality configured to generate an output that is indicative of the subject having used accessory muscles in breathing, in response to identification of the double-movement-respiration-cycle event; and a user interface configured to display the output, wherein the double-movement-respiration-cycle-event-identification functionality is configured to identify the double-movement-respiration-cycle event by detecting that at least 30% of respiration cycles of the subject over a period of time of at least one minute define two subcycles.

17. The apparatus according to claim 16, wherein the double-movement-respiration-cycle-event-identification functionality is configured to identify the double-movement-respiration-cycle event by detecting that at least 60% of respiration cycles of the subject over the period of time of at least one minute define two subcycles.

18. The apparatus according to claim 16, wherein the double-movement-respiration-cycle-event-identification functionality is configured to identify the double-movement-respiration-cycle event by detecting that at least 30% of respiration cycles of the subject over a period of time of at least ten minutes define two subcycles.

19. The apparatus according to claim 18, wherein the double-movement-respiration-cycle-event-identification functionality is configured to identify the double-movement-respiration-cycle event by detecting that at least 30% of respiration cycles of the subject over a period of time of at least 30 minutes define two subcycles.

20. The apparatus according to claim 19, wherein the double-movement-respiration-cycle-event-identification functionality is configured to identify the double-movement-respiration-cycle event by detecting that at least 30% of respiration cycles of the subject over a period of time of at least 60 minutes define two subcycles.

21. The apparatus according to claim 16, wherein the control unit is configured to predict an onset of a clinical condition of the subject in response to the double-movement-respiration-cycle-event-identification functionality identifying the double-movement-respiration-cycle event.

22. Apparatus for use with a subject who is undergoing respiration, the apparatus comprising:
a motion sensor configured to sense motion of a subject;
a control unit comprising:
a breathing pattern analysis unit that is configured to analyze components of the sensed motion that result from the subject's respiration, the breathing pattern analysis unit comprising:
double-movement-respiration-cycle-pattern-identification functionality that is configured to designate respiration cycles as being double-movement-respiration-cycles by determining that the cycles define two subcycles; and
double-movement-respiration-cycle-event-identification functionality configured to identify a double-movement-respiration-cycle event by detecting that the subject has undergone a plurality of double-movement-respiration-cycles; and
output-generation functionality configured to generate an output that is indicative of an onset of an episode of respiratory distress, in response to the double-movement-respiration-cycle event; and
a user interface configured to display the output,
wherein the double-movement-respiration-cycle-pattern-identification functionality is configured to distinguish between a first cycle that defines two subcycles, and a second cycle that does not define two subcycles, even if the first and second cycles have substantially similar amplitudes to one another.

23. The apparatus according to claim 22, wherein the output-generation functionality is configured to generate the output by generating an output that is indicative of the onset of an elevated respiration rate.

24. The apparatus according to claim 22, wherein the double-movement-respiration-cycle-event-identification functionality is configured to predict the onset of the respiratory distress at least 30 minutes before the onset of the respiratory distress, in response to the double-movement-respiration-cycle event, and wherein the output-generation functionality is configured to generate the output, in response thereto.

25. The apparatus according to claim 22, wherein the output-generation functionality is further configured to generate an output that is indicative of the onset of an elevated heart rate of the subject, in response to the double-movement-respiration-cycle event.

26. The apparatus according to claim 22, wherein the sensor is configured to sense motion of the subject without contacting the subject or clothes the subject is wearing.

27. The apparatus according to claim 22, wherein the sensor is configured to sense motion of the subject without contacting or viewing the subject or clothes the subject is wearing.

28. The apparatus according to claim 22, wherein the double-movement-respiration-cycle-pattern-identification functionality is configured to determine that a cycle defines two subcycles at least partially in response to a slope of a respiration motion signal of the subject.

29. Apparatus for use with a subject who is undergoing respiration, the apparatus comprising:
a motion sensor configured to sense motion of a subject;
a control unit comprising:
a breathing pattern analysis unit that is configured to analyze components of the sensed motion that result from the subject's respiration, the breathing pattern analysis unit comprising:
double-movement-respiration-cycle-pattern-identification functionality that is configured to designate respiration cycles as being double-movement-respiration-cycles by determining that the cycles define two subcycles; and
double-movement-respiration-cycle-event-identification functionality configured to identify a double-movement-respiration-cycle event by detecting that the subject has undergone a plurality of double-movement-respiration-cycles; and
output-generation functionality configured to generate an output that is indicative of an onset of an episode of respiratory distress, in response to the double-movement-respiration-cycle event; and
a user interface configured to display the output,
wherein the double-movement-respiration-cycle-pattern-identification functionality is configured to distinguish between a first cycle that defines two subcycles, and a second cycle that does not define two subcycles, even if the first and second cycles have substantially similar frequencies to one another.

30. Apparatus for use with a subject who is undergoing respiration, the apparatus comprising:
a motion sensor configured to sense motion of a subject;
a control unit comprising:
a breathing pattern analysis unit that is configured to analyze components of the sensed motion that result from the subject's respiration, the breathing pattern analysis unit comprising:

double-movement-respiration-cycle-pattern-identification functionality that is configured to designate respiration cycles as being double-movement-respiration-cycles by determining that the cycles define two subcycles; and double-movement-respiration-cycle-event-identification functionality configured to identify a double-movement-respiration-cycle event by detecting that the subject has undergone a plurality of double-movement-respiration-cycles; and output-generation functionality configured to generate an output that is indicative of an onset of an episode of respiratory distress, in response to the double-movement-respiration-cycle event; and a user interface configured to display the output, wherein the double-movement-respiration-cycle-pattern-identification functionality is configured to determine that a cycle defines two subcycles at least partially in response to an amplitude of the cycle.

31. Apparatus for use with a subject who is undergoing respiration, the apparatus comprising:

a motion sensor configured to sense motion of a subject;

a control unit comprising:

a breathing pattern analysis unit that is configured to analyze components of the sensed motion that result from the subject's respiration, the breathing pattern analysis unit comprising:

double-movement-respiration-cycle-pattern-identification functionality that is configured to designate respiration cycles as being double-movement-respiration-cycles by determining that the cycles define two subcycles; and double-movement-respiration-cycle-event-identification functionality configured to identify a double-movement-respiration-cycle event by detecting that the subject has undergone a plurality of double-movement-respiration-cycles; and output-generation functionality configured to generate an output that is indicative of an onset of an episode of respiratory distress, in response to the double-movement-respiration-cycle event; and a user interface configured to display the output, wherein double-movement-respiration-cycle-pattern-identification functionality is configured to determine that a cycle defines two subcycles at least partially in response to a frequency of the cycle.

32. Apparatus for use with a subject who is undergoing respiration, the apparatus comprising:

a motion sensor configured to sense motion of a subject;

a control unit comprising:

a breathing pattern analysis unit that is configured to analyze components of the sensed motion that result from the subject's respiration, the breathing pattern analysis unit comprising:

double-movement-respiration-cycle-pattern-identification functionality that is configured to designate respiration cycles as being double-movement-respiration-cycles by determining that the cycles define two subcycles; and double-movement-respiration-cycle-event-identification functionality configured to identify a double-movement-respiration-cycle event by detecting that the subject has undergone a plurality of double-movement-respiration-cycles; and output-generation functionality configured to generate an output that is indicative of an onset of an episode of respiratory distress, in response to the double-movement-respiration-cycle event; and a user interface configured to display the output, wherein the double-movement-respiration-cycle-pattern-identification functionality is configured to determine that a cycle defines two subcycles by identifying two adjacent peak and trough sets of a respiration motion signal of the subject that are substantially asymmetrical with respect to one another, and, in response thereto, designating the adjacent peak and trough sets as being two subcycles of a single respiration cycle.

33. Apparatus for use with a subject who is undergoing respiration, the apparatus comprising:

a motion sensor configured to sense motion of a subject;

a control unit comprising:

a breathing pattern analysis unit that is configured to analyze components of the sensed motion that result from the subject's respiration, the breathing pattern analysis unit comprising:

double-movement-respiration-cycle-pattern-identification functionality that is configured to designate respiration cycles as being double-movement-respiration-cycles by determining that the cycles define two subcycles; and double-movement-respiration-cycle-event-identification functionality configured to identify a double-movement-respiration-cycle event by detecting that the subject has undergone a plurality of double-movement-respiration-cycles; and output-generation functionality configured to generate an output that is indicative of an onset of an episode of respiratory distress, in response to the double-movement-respiration-cycle event; and a user interface configured to display the output, wherein the double-movement-respiration-cycle-event-identification functionality is configured to identify the double-movement-respiration-cycle event by detecting that at least 30% of respiration cycles of the subject over a period of time of at least one minute define two subcycles.

34. The apparatus according to claim 33, wherein the double-movement-respiration-cycle-event-identification functionality is configured to identify the double-movement-respiration-cycle event by detecting that at least 60% of respiration cycles of the subject over the period of time of at least one minute define two subcycles.

35. The apparatus according to claim 33, wherein the double-movement-respiration-cycle-event-identification functionality is configured to identify the double-movement-respiration-cycle event by detecting that at least 30% of respiration cycles of the subject over a period of time of at least ten minutes define two subcycles.

36. The apparatus according to claim 35, wherein the double-movement-respiration-cycle-event-identification functionality is configured to identify the double-movement-respiration-cycle event by detecting that at least 30% of respiration cycles of the subject over a period of time of at least 30 minutes define two subcycles.

37. The apparatus according to claim 36, wherein the double-movement-respiration-cycle-event-identification functionality is configured to identify the double-movement-respiration-cycle event by detecting that at least 30% of respiration cycles of the subject over a period of time of at least 60 minutes define two subcycles.

* * * * *